United States Patent
Mizrahi et al.

(10) Patent No.: US 10,174,343 B2
(45) Date of Patent: *Jan. 8, 2019

(54) LACTIC ACID BACTERIA FOR THE PRODUCTION OF ETHANOL FROM BIOMASS MATERIAL

(71) Applicants: The State of Israel, Ministry of Agriculture & Rural Development, Agricultural Research Organization (ARO) (Volcani Center), Rishon-LeZion (IL); Yeda Research and Development Co. Ltd., Rehovot (IL); Ramot at Tel-Aviv University Ltd., Tel-Aviv (IL)

(72) Inventors: Itzhak Mizrahi, Tel-Aviv (IL); Naama Shterzer, Tel-Aviv (IL); Raphael Lamed, Yavne (IL); Inna Rozman Grinberg, RaAnana (IL); Edward A. Bayer, Ramot-HaShavim (IL); Sarah Morais, Ashdod (IL); Etai Landou, Rehovot (IL)

(73) Assignees: The State of Israel, Ministry of Agriculture & Rural Development, Agricultural Research Organization (ARD) (Volcani Center), Rishon-LeZion (IL); Yeda Research and Development Co. Ltd., Rehovot (IL); Ramot at Tel-Aviv University Ltd., Tel-Aviv (IL)

( * ) Notice: Subject to any disclaimer, the term of this patent is extended or adjusted under 35 U.S.C. 154(b) by 0 days.

This patent is subject to a terminal disclaimer.

(21) Appl. No.: 15/108,389

(22) PCT Filed: Dec. 26, 2013

(86) PCT No.: PCT/IL2013/051074
§ 371 (c)(1),
(2) Date: Jun. 27, 2016

(87) PCT Pub. No.: WO2015/097686
PCT Pub. Date: Jul. 2, 2015

(65) Prior Publication Data
US 2016/0326550 A1 Nov. 10, 2016

(51) Int. Cl.
| | |
|---|---|
| *C12P 19/14* | (2006.01) |
| *C12P 7/14* | (2006.01) |
| *C12N 1/22* | (2006.01) |
| *C12P 39/00* | (2006.01) |
| *C12N 9/42* | (2006.01) |
| *C12N 9/24* | (2006.01) |
| *C12P 7/06* | (2006.01) |
| *C12N 9/04* | (2006.01) |
| *C12N 9/88* | (2006.01) |
| *C12P 7/10* | (2006.01) |
| *C12Q 1/6888* | (2018.01) |

(52) U.S. Cl.
CPC .......... *C12P 7/14* (2013.01); *C12N 1/22* (2013.01); *C12N 9/0006* (2013.01); *C12N 9/248* (2013.01); *C12N 9/2437* (2013.01); *C12N 9/2482* (2013.01); *C12N 9/88* (2013.01); *C12P 7/065* (2013.01); *C12P 7/10* (2013.01); *C12P 39/00* (2013.01); *C12Q 1/6888* (2013.01); *C12Y 101/01001* (2013.01); *C12Y 302/01004* (2013.01); *C12Y 302/01008* (2013.01); *C12Y 302/01091* (2013.01); *C12Y 401/01001* (2013.01); *Y02E 50/16* (2013.01); *Y02E 50/17* (2013.01)

(58) Field of Classification Search
CPC ......... C12P 19/14; Y02E 50/16; C12N 9/243; C12N 9/248
See application file for complete search history.

(56) References Cited

U.S. PATENT DOCUMENTS

| | | | |
|---|---|---|---|
| 2010/0129885 A1 | 5/2010 | Khramtsov et al. | |
| 2011/0230682 A1 | 9/2011 | Schmalisch et al. | |
| 2012/0190090 A1 | 7/2012 | Bokinsky et al. | |
| 2016/0326485 A1 | 11/2016 | Mizrahi et al. | |

FOREIGN PATENT DOCUMENTS

| | | |
|---|---|---|
| WO | WO 89/01970 | 3/1989 |
| WO | WO 2011/116358 | 9/2011 |
| WO | WO 2015/097685 | 7/2015 |
| WO | WO 2015/097686 | 7/2015 |

OTHER PUBLICATIONS

Supplementary European Search Report and the European Search Opinion dated Apr. 19, 2017 From the European Patent Office Re. Application No. 13900046.7. (10 pages).
Baek et al. "Cellulosic Ethanol Production by Combination of Cellulase-Displaying Yeast Cells", Enzyme and Microbial Technology, XP055361736, 51(6-7): 366-372, Dec. 2012. Abstract.
Mazzoli et al. "Towards Lactic Acid Bacteria-Based Biorefineries", Biotechnology Advances, XP055361666, 32(7): 1216-1236, Available Online Aug. 1, 2014. Abstract, p. 1224, col. 2-p. 1225, col. 2.
Morais et al. "Contribution of a Xylan-Binding Module to the Degradation of a Complex Cellulosic Substrate by Designer Cellulosomes", Applied and Environmental Microbiology, XP055361743, 76(12): 3787-3796, Jun. 15, 2010. Abstract.
Tabka et al. "Enzymatic Saccafification of Wheat Straw for Bioethanol Production by a Combined Cellulase Xylanase and Femloyl Esterase Treatment", Enzyme and Microbial Technology, XP002511088, 39(4): 897-902, Aug. 2006. Abstract, Fig.2.

(Continued)

*Primary Examiner* — Karen Cochrane Carlson

(57) ABSTRACT

Lactic acid bacterial cultures, cell populations and articles of manufacture comprising same are disclosed for generating ethanol from lignocellulose.

21 Claims, 6 Drawing Sheets
Specification includes a Sequence Listing.

(56) References Cited

OTHER PUBLICATIONS

International Preliminary Report on Patentability dated Jul. 7, 2016 From the International Bureau of WIPO Re. Application No. PCT/IL2013/051074.
International Preliminary Report on Patentability dated Jul. 7, 2016 From the International Bureau of WIPO Re. Application No. PCT/IL2013/051071.
International Search Report and the Written Opinion dated Apr. 8, 2014 From the International Searching Authority Re. Application No. PCT/IL2013/051071.
International Search Report and the Written Opinion dated Apr. 9, 2014 From the International Searching Authority Re. Application No. PCT/IL2013/051074.
Bates et al. "Expression of a Clostridium Thermocellum Endoglucanase Gene in Lactobacillus plantarum", Applied and Environmental Microbiology, 55(8): 2095-2097, Aug. 1989.
Caspi et al. "Effect of Linker Length and Dockerin Position on Conversion of a Thermobifida Fusca Endoglucanase to the Cellulosomal Mode", Applied and Enviromental Microbiology, 75(23): 7335-7342, Oct. 9, 2009. Fig.6.
Liu et al. "Coexpression of Rumen Microbial Beta-Glucanase and Xylanase Genes in Lactobacillus reuteri", Applied Microbiology and Biotechnology, 77: 117-124, Published Online: Aug. 11, 2007.
Liu et al. "Metabolic Engineering of a Lactobacillus Plantarum Double Ldh Knockout Strain for Enhanced Ethanol Production", Journal of Industrial Microbiology and Biotechnology, 33(1): 1-7, Sep. 29, 2005. Introduction, Abstract, p. 2, Left col., Para. 2.
Morais et al. "Establishment of a Simple Lactobacillus Plantarum Cell Consortium for Cellulase-Xylanase Synergistic Interactions", Applied and Environmental Microbiology, 79(17): 5242-5249, Jun. 28, 2013. p. 5246, r-h col., First Para, Figs.4-6, Materials and Methods, 'Cloning' Section, Abstract, p. 5248, Left col., 1st Para.
Ozkose et al. "Expression of Fungal Cellulase Gene in Lactococcus lactis to Construct Novel Recombinant Silage Inoculants", Folia Microbiologica, 54(4): 335-342, 2009.
Rossi et al. "Vector-Free Cloning of a Bacterial Endo-1,4-Beta-Glucanase in Lactobacillus Plantarum and Its Effect on the Acidifying Activity in Silage: Use of Recombinant Cellulolytic Lactobacillus Plantarum as Silage Inoculant", Antonie van Leeuwenhoek, 80: 139-147, 2001.
Scheirlinck et al. "Cloning and Expression of Cellulase and Xylanase Genes in Lactobacillus plantarum", Applied Microbiology and Biotechnology, 33: 534-541, Aug. 1, 1990.
Scheirlinck et al. "Integration and Expression of Alpha-Amylase and Endoglucanase Genes in the Lactobacillus plantarum Chromosome", Applied and Envrionmental Microbiology, 55(9): 2130-2137, Sep. 1989.
Solem et al. "Rewiring Lactococcus Lactis for Ethanol Production", Applied and Environemntal Microbiology, 79(8): 2512-2518, Apr. 2013.
Vertes et al. "Conversion of Biomass to Ethanol by Other Organisms", Biomass to Biofuels: Strategies for Global Industries, Chap. 14: 293-310, Jan. 12, 2010. Chap.14, p. 293-310.
Official Action dated Jan. 26, 2018 From the US Patent and Trademark Office Re. U.S. Appl. No. 15/108,410. (23 pages).
Morais et al. "Cellulase-Xylanase Synergy in Designer Cellulosomes for Enhanced Degradation of a Complex Cellulosic Substrate", MBio 1(5): e00285.1-e00285.10, Nov./Dec. 2010.
Shin et al. "*Escherichia coli* Binary Culture Engineered for Direct Fermentation of Hemicellulose to a Biofuel", Applied and Environmental Microbiology 76(24): 8150-8159, Dec. 15, 2010.

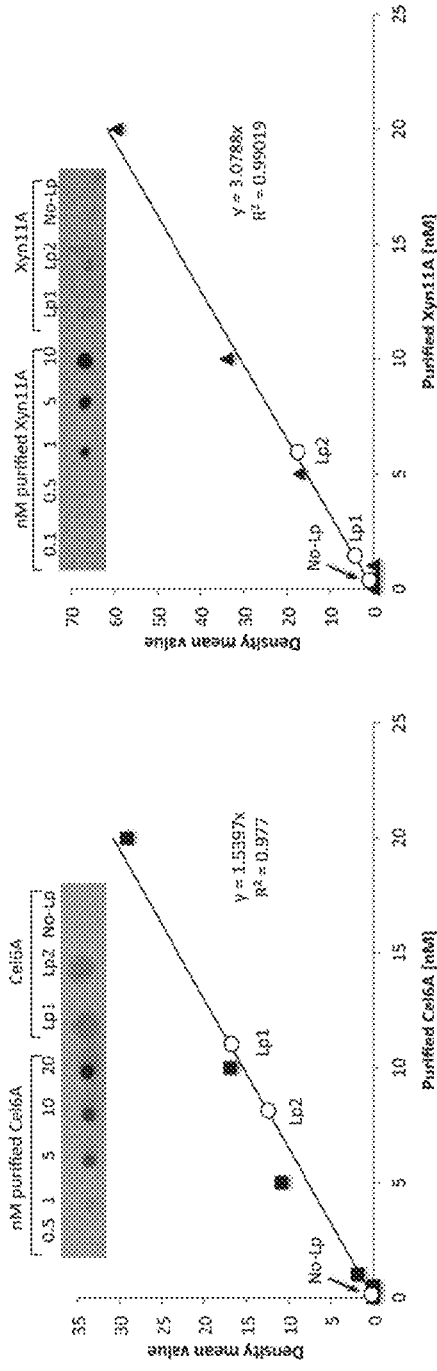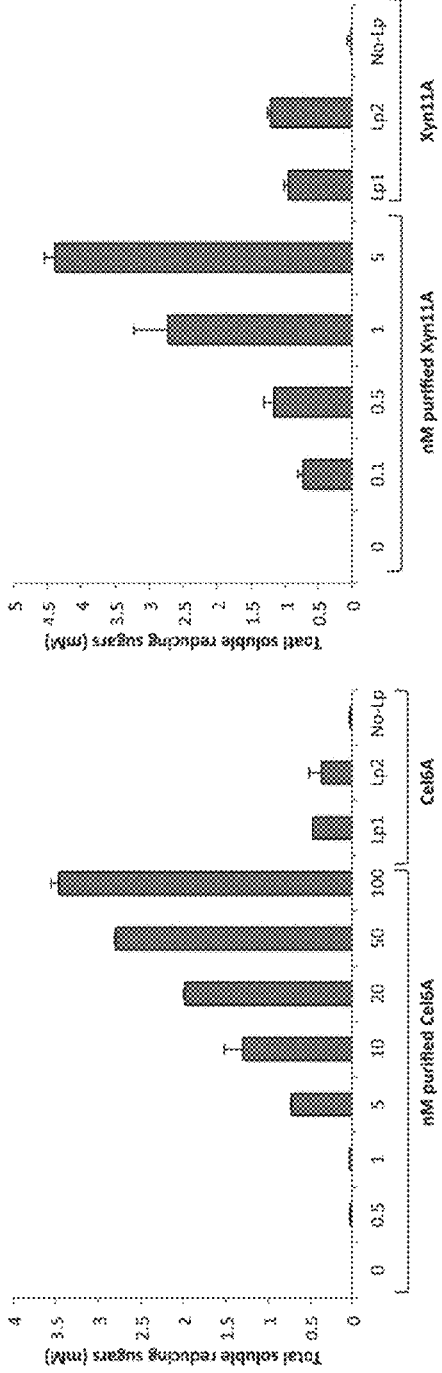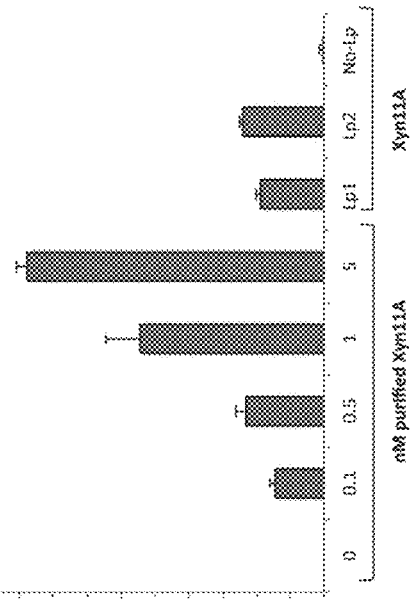

LACTIC ACID BACTERIA FOR THE PRODUCTION OF ETHANOL FROM BIOMASS MATERIAL

RELATED APPLICATION

This application is a National Phase of PCT Patent Application No. PCT/IL2013/051074 having International filing date of Dec. 26, 2013, the contents of which are incorporated by reference as if fully set forth herein in their entirety.

SEQUENCE LISTING STATEMENT

The ASCII file, entitled 66811SequenceListing.txt, created on Jun. 27, 2016 comprising 85,948 bytes, submitted concurrently with the filing of this application is incorporated herein by reference.

FIELD AND BACKGROUND OF THE INVENTION

The present invention, in some embodiments thereof, relates to methods and recombinant lactic acid bacteria for the production of ethanol from biomass material by a consolidated bioprocessing approach.

Ethanol is an established alternative fuel from renewable resources. Today it is mainly produced from sugar or starchy biomass, limiting the environmental benefit and posing a competition for the raw materials with food industry. In the last decade research efforts have mounted to replace this 1st generation ethanol by the 2nd generation ethanol made from lignocellulosic feedstocks, including pretreatment, enzymatic hydrolysis, sugar fermentation and process design. Most of the processes developed toward industrial scale involve addition of enzymes for cellulose and hemicellulose hydrolysis and use of specific yeast strains engineered to utilize C5 and C6 sugars. Both achieving effective biomass hydrolysis and complete sugar conversion are essential for an economical process. Although enzyme producers have made substantial improvements in the recent years, cost of cellulase enzymes are still in the range of $0.5 to $1.0 per gallon of 2nd generation ethanol.

A process strategy that aims to circumvent this critical cost-increasing item is the consolidated bioprocessing approach. In CBP an organism or a mixed culture of organisms produces enzymes for hydrolysis of cellulose and hemicellulose in lignocellulosic biomass and ferments the C5 and C6 sugars into ethanol or other valuable products without addition of cellulolytic or hemicellulolytic enzymes. Several mesophilic and thermophilic cellulolytic as well as non-cellulolytic microorganisms with engineered cellulase activity are under development for the application in CBP [Olson D G, et al., Curr Opin Biotechnol 2011, 23:1-10; La Grange D C Appl Microbiol Biotechnol 2010, 87:1195-1208; Svetlitchnyi et al., Biotechnology for Biofuels 2013, 6:31].

Conversion of lignocellulose to ethanol requires ethanol-tolerant microorganisms capable of degrading lignocellulose to fermentable sugars and fermenting the various sugars (pentoses and hexoses) released due to the hydrolysis of the lignocellulosic biomass.

*Lactobacillus plantarum* is a common lactic acid bacterium used in a variety of industrial and agricultural applications. *L. plantarum* prospers in environments containing lignocellulosic plant biomass. For example, in agriculture, these organisms are employed for conservation of lignocellulosic plant biomass for use in animal feed. In a process called ensilage, they quickly dominate the microbial population and produce lactic and acetic acids, thereby causing a pH drop which suppresses other microbial and fungal species. This bacterium was reported to possess high tolerance to ethanol concentrations in the media (up to 13% (v/v)).

*L. plantarum* is also able to metabolize pentose and hexose sugars derived from the lignocellulosic biomass. These attributes provide the bacterium with distinct advantages over the commonly used ethanol-producing yeast, *Saccharomyces cerevisiae*, which, in its native form, does not metabolize pentose. Another advantage is its acid tolerance which enables production of ethanol at low pH, thus reducing possible contamination by other bacteria and fungi and sparing handling steps due to acidic conditions sometimes imposed by pretreatment procedures. Furthermore, recent developments in the molecular biology of these bacteria include novel protein expression systems and the availability of the *L. plantarum* full genome sequence. Convenient genetic manipulation and robust expression of foreign genes render the genetic manipulations of these bacteria an accomplishable task.

U.S. Patent Application No. 20100129885 teaches microorganisms including *Lactobacillus plantarum* which are genetically modified to express cellulases and enzymes which are part of the butanol biosynthetic pathway.

U.S. Patent Application No. 20120190090 teaches microorganisms genetically modified to express cellulases and enzymes which are part of the butanol biosynthetic pathway.

Solem et al [Appl. Environ. Microbiol. 2013, 79(8):2512] teaches genetic engineering of *Lactococcus lactis* for ethanol production.

Additional background art includes U.S. Patent Application No. 20110230682.

SUMMARY OF THE INVENTION

According to an aspect of some embodiments of the present invention there is provided a bacterial culture comprising a biomass composition and a population of lactic acid bacteria which comprises:

(i) a first population of lactic acid bacteria which has been genetically modified to express a secreted cellulase;

(ii) a second population of lactic acid bacteria which has been genetically modified to express a secreted xylanase, wherein the ratio of the first population:second population is selected such that the specific activity of cellulase:xylanase in the culture is greater than 4:1 or less than 1:4; and (iii) a third population of lactic acid bacteria which has been genetically modified to produce ethanol.

According to an aspect of some embodiments of the present invention there is provided a bacterial culture comprising a biomass composition and a population of lactic acid bacteria which comprises:

(i) a first population of lactic acid bacteria which has been genetically modified to express a secreted cellulase;

(ii) a second population of lactic acid bacteria which has been genetically modified to express a secreted xylanase, wherein the ratio of the first population:second population is selected such that the specific activity of cellulase:xylanase in the culture is greater than 4:1 or less than 1:4, wherein the first and/or the second population of lactic acid bacteria has been further genetically modified to produce ethanol.

According to an aspect of some embodiments of the present invention there is provided an article of manufacture comprising:

(i) a first population of lactic acid bacteria which are genetically modified to express at least one fibrolytic enzyme; and (ii) a second population of lactic acid bacteria which are genetically modified to produce ethanol from C5 or C6 sugars, wherein the first population of lactic acid bacteria and the second population of lactic acid bacteria are packaged in separate packaging.

According to an aspect of some embodiments of the present invention there is provided an isolated cell population comprising:

(i) a first population of lactic acid bacteria which are genetically modified to express at least one fibrolytic enzyme; and (ii) a second population of lactic acid bacteria which are genetically modified to produce ethanol from C5 or C6 sugars.

According to an aspect of some embodiments of the present invention there is provided an isolated cell population of lactic acid bacteria which are genetically modified to express at least one fibrolytic enzyme and to produce ethanol from C5 or C6 sugars.

According to an aspect of some embodiments of the present invention there is provided a bacterial culture comprising the isolated cell population described herein, and a biomass composition.

According to an aspect of some embodiments of the present invention there is provided a method of producing ethanol comprising propagating the culture described herein under conditions that allow generation of the ethanol, thereby producing the ethanol.

According to some embodiments of the invention, the first population of lactic acid bacteria express a cellulase.

According to some embodiments of the invention, the article of further comprises a third population of lactic acid bacteria, which are genetically modified to express a xylanase.

According to some embodiments of the invention, the at least one fibrolytic enzyme is expressed as a fusion protein with dockerin.

According to some embodiments of the invention, the lactic acid bacteria comprise *Lactobacillus plantarum*.

According to some embodiments of the invention, the biomass composition comprises cellulose and/or hemicellulose.

According to some embodiments of the invention, the biomass further comprises lignin.

According to some embodiments of the invention, the biomass is selected from the group consisting of paper, paper products, paper waste, wood, particle board, sawdust, agricultural waste, sewage, silage, grasses, rice hulls, bagasse, jute, hemp, flax, bamboo, sisal, abaca, straw, corn cobs, corn stover, switchgrass, alfalfa, hay, coconut hair, cotton, seaweed, algae, and mixtures thereof.

According to some embodiments of the invention, the ratio of the first population:second population is selected such that the specific activity of cellulase: xylanase in the culture is greater than 10:1 or less than 1:10.

According to some embodiments of the invention, the at least one fibrolytic enzyme comprises a cellulose and/or a xylanase.

According to some embodiments of the invention, the at least one fibrolytic enzyme is cellulase.

According to some embodiments of the invention, the isolated cell population further comprises a third population of lactic acid bacteria which are genetically modified to express a xylanase.

According to some embodiments of the invention, the first population of lactic acid bacteria comprise *Lactobacillus plantarum*.

According to some embodiments of the invention, the second population of lactic acid bacteria comprise *Lactobacillus plantarum*.

According to some embodiments of the invention, the third population of lactic acid bacteria comprise *Lactobacillus plantarum*.

According to some embodiments of the invention, the lactic acid bacteria comprise *Lactobacillus plantarum*.

According to some embodiments of the invention, the cellulase is a *Thermobifida fusca* cellulase.

According to some embodiments of the invention, the xylanase is a *Thermobifida fusca* xylanase.

According to some embodiments of the invention, the cellulase is a mesophilic bacteria cellulase.

According to some embodiments of the invention, the xylanase is a mesophilic bacteria xylanase.

According to some embodiments of the invention, the mesophilic bacteria is a *Ruminococcus flavefaciens* or *Ruminococcus albus*.

According to some embodiments of the invention, the first population and the second population comprise identical strains of bacteria.

According to some embodiments of the invention, the first population and the second population comprise non-identical strains of bacteria.

According to some embodiments of the invention, the second population of lactic acid bacteria are genetically modified to express alcohol dehydrogenase and pyruvate decarboxylase.

According to some embodiments of the invention, the third population of lactic acid bacteria are genetically modified to express alcohol dehydrogenase and pyruvate decarboxylase.

According to some embodiments of the invention, the first population of lactic acid bacteria and/or the second population of lactic acid bacteria are genetically modified to express alcohol dehydrogenase and pyruvate decarboxylase.

According to some embodiments of the invention, the isolated cell population is genetically modified to express alcohol dehydrogenase and pyruvate decarboxylase.

According to some embodiments of the invention, the alcohol dehydrogenase is a *Zymomonas mobilis* alcohol dehydrogenase.

According to some embodiments of the invention, the pyruvate decarboxylase is a *Zymomonas mobilis* pyruvate decarboxylase.

According to some embodiments of the invention, the pyruvate decarboxylase is a *Sarcina ventriculi* pyruvate decarboxylase.

According to some embodiments of the invention, the second population of lactic acid bacteria do not express at least one L-lactate dehydrogenase.

According to some embodiments of the invention, the isolated cell population is genetically modified so as not to express at least one L-lactate dehydrogenase.

According to some embodiments of the invention, the third population of lactic acid bacteria do not express at least one L-lactate dehydrogenase.

According to some embodiments of the invention, the first and/or the second population of lactic acid bacteria do not express at least one L-lactate dehydrogenase.

According to some embodiments of the invention, the at least one L-lactate dehydrogenase is selected from the group consisting of L-lactate dehydrogenase 1 (Ldh-L1), L-lactate dehydrogenase 2 (Ldh-L2) and D-lactate dehydrogenase (Ldh-D).

According to some embodiments of the invention, the second population of lactic acid bacteria do not produce butanol.

According to some embodiments of the invention, does not produce butanol.

According to some embodiments of the invention, the third population of lactic acid bacteria does not produce butanol.

According to some embodiments of the invention, the method further comprises isolating the ethanol following the generating.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 3A-D are bar graphs illustrating quantification of the secreted enzymes. A. Dot blot analysis of increasing concentrations of purified Ce16A in nM and 2 μL of concentrated culture supernatant fluids. The graph shows the mean intensity of each spot for the calibration curve in black and the white circles represent the intensity of the spot for Ce16A cultures (No-Lp, Lp1 and Lp2). B. Dot blot analysis of increasing concentrations of purified Xyn11A in nM and 2 μL of dialyzed culture supernatant fluids. The irrelevant spots between the samples of Lp2 and No-Lp were cropped in the panel. C. Enzymatic activity on PASC. Reactions were conducted with increasing concentrations of purified Ce16A and with 30 μL concentrated culture supernatant fluids. Enzymatic activity is defined as mM soluble reducing sugars released following an 18-h reaction period. Each reaction was performed in triplicate, and standard deviations are indicated. D. Enzymatic activity on xylan. Reactions were conducted with increasing concentrations of purified Xyn11A and with 30 μL dialyzed culture supernatant fluids. Enzymatic activity is defined as mM soluble reducing sugars following a 2-h reaction period. Each reaction was performed in triplicate, and standard deviations for xylan hydrolysis are indicated.

The concentration of pretreated wheat straw (dry matter) in the reactions was 3.5 g/l. Assuming that all detected reducing ends belong to dimers the highest detected product concentration (1:500 ratio) represents 27.6% polysaccharide conversion. Enzymatic activity is defined as mM soluble reducing sugars following a 24-h reaction period at 37° C. and pH 5. Each reaction was performed in triplicate, and standard deviations are indicated. The theoretical additive effect is defined as the sum of the activities of the individual Ce16A- and Xyn11A-secreting cultures (see Materials and Methods section for a detailed explanation), and synergism was calculated as the ratio between the measured activity and the theoretical activity assuming additivity.

Figure 6:
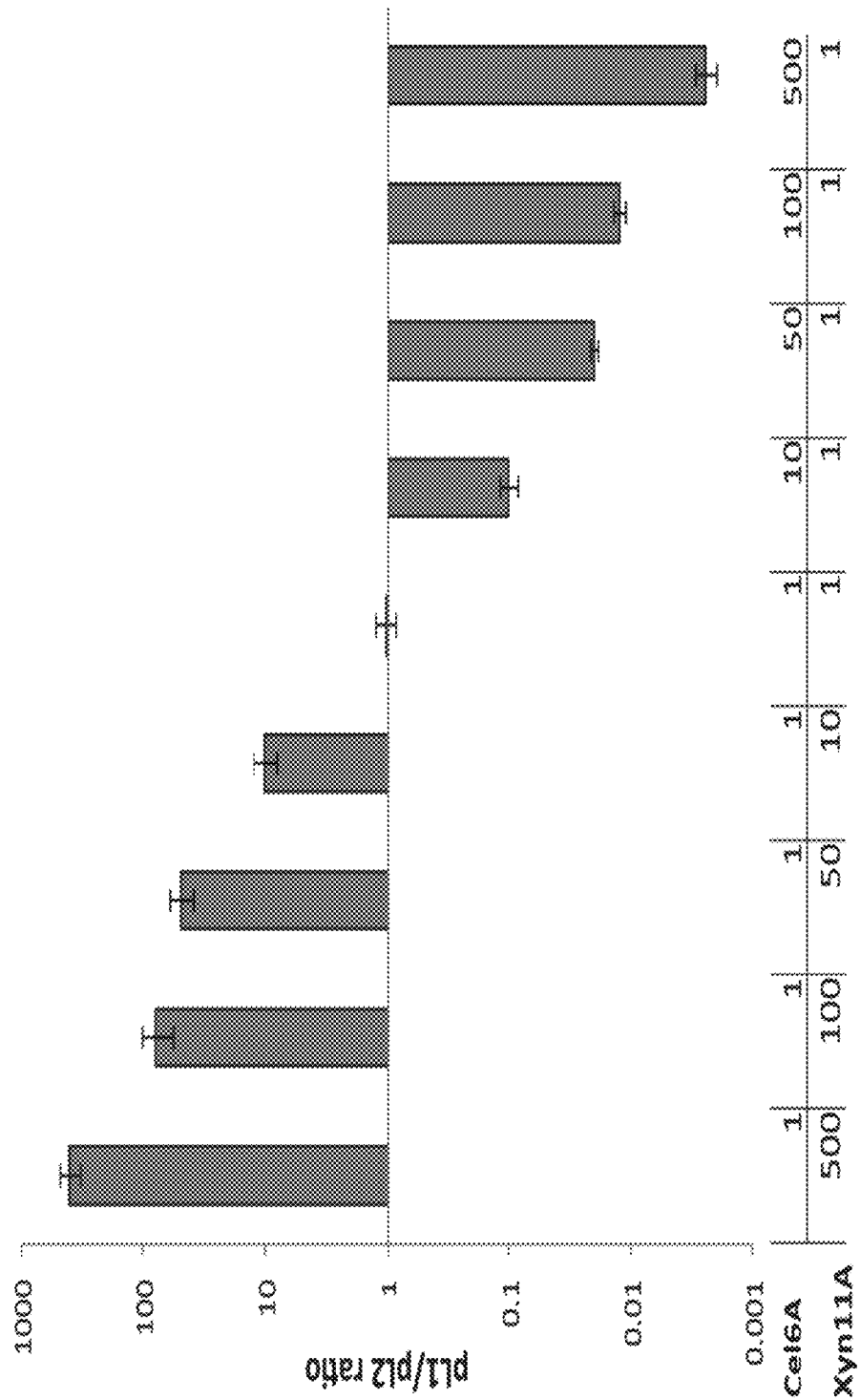

FIG. 6 is a bar graph illustrating the ratios between Lp1-Ce16A and Lp2-Xyn11A in cocultures after the growth period, as determined by RT-PCR. Cultures were inoculated using various ratios (Ce16A/Xyn11A): 1/500, 1/100, 1/50, 1/10, 1/1, 10/1, 50/1, 100/1 and 500/1. Total copy numbers of each plasmid were determined for each coculture, and ratios were calculated.

DESCRIPTION OF SPECIFIC EMBODIMENTS OF THE INVENTION

The present invention, in some embodiments thereof, relates to methods and recombinant lactic acid bacteria for the production of ethanol from biomass material by a consolidated bioprocessing approach.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Lignocellulose biomass is a significant renewable resource for the generation of sugars. Fermentation of these sugars can yield commercially valuable end-products, including biofuels and chemicals that are currently derived from petroleum. While the fermentation of simple sugars to ethanol is relatively straightforward, the efficient conversion of cellulosic biomass to fermentable sugars is challenging. Typically, yeast is used as the major production organism. However, there are drawbacks to yeast including its slow rate of growth and fermentation, its capability of naturally fermenting only a few sugars and its poor tolerance to high temperatures. In addition, lignocellulose pretreatment releases compounds such as acetate that are inhibitory to the yeast cells.

Lactic acid bacteria (LAB) naturally ferment both hexoses and pentoses, tolerate high concentrations of organic acids, and tolerate harsh conditions. In addition, LAB have an innate high tolerance to ethanol and are frequently found in bioethanol plants as contaminants. They are able to grow at low pH, and some also thrive at elevated temperatures, both properties that are important for avoiding contamination and in addition they meet the requirements for simultaneous saccharification and fermentation (SSF).

The present inventors propose generation of genetically modified lactic acid bacteria that are capable of digesting the cellulose and hemicellulose component of lignocellulose and then using the released pentose and hexose sugars to synthesize ethanol without the addition of cellulolytic or hemicellulolytic enzymes.

Figure 4:
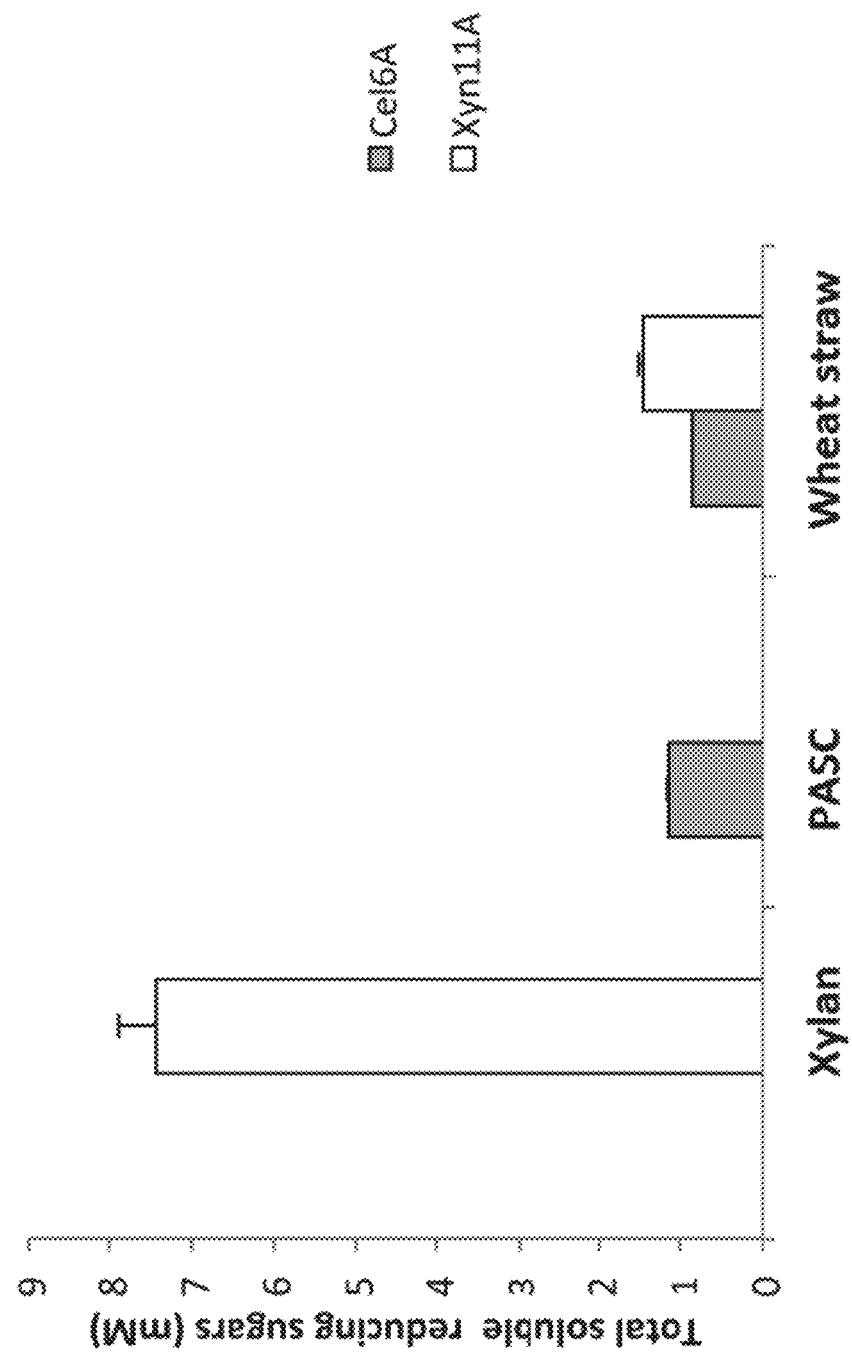
FIG. 4 is a bar graph illustrating activity of secreted enzymes on various substrates. Comparative enzymatic activity of supernatants derived from cultures producing either the cellulase (grey bars) or the xylanase (white bars). The substrates, PASC, xylan or pretreated wheat straw, were incubated with 30 μl of supernatant fluids (concentrated to approximately 16.5 nM of enzyme). The enzymatic activity of Ce16A is represented by grey bars and Xyn11A by white bars. Enzymatic activity is defined as mM soluble reducing sugars following a 2-h reaction period for xylan, 18-h incubation for PASC or 24-h incubation for wheat straw at pH 5 and 37° C. Each reaction was performed in triplicate, and standard deviations are indicated.
Figure 5:
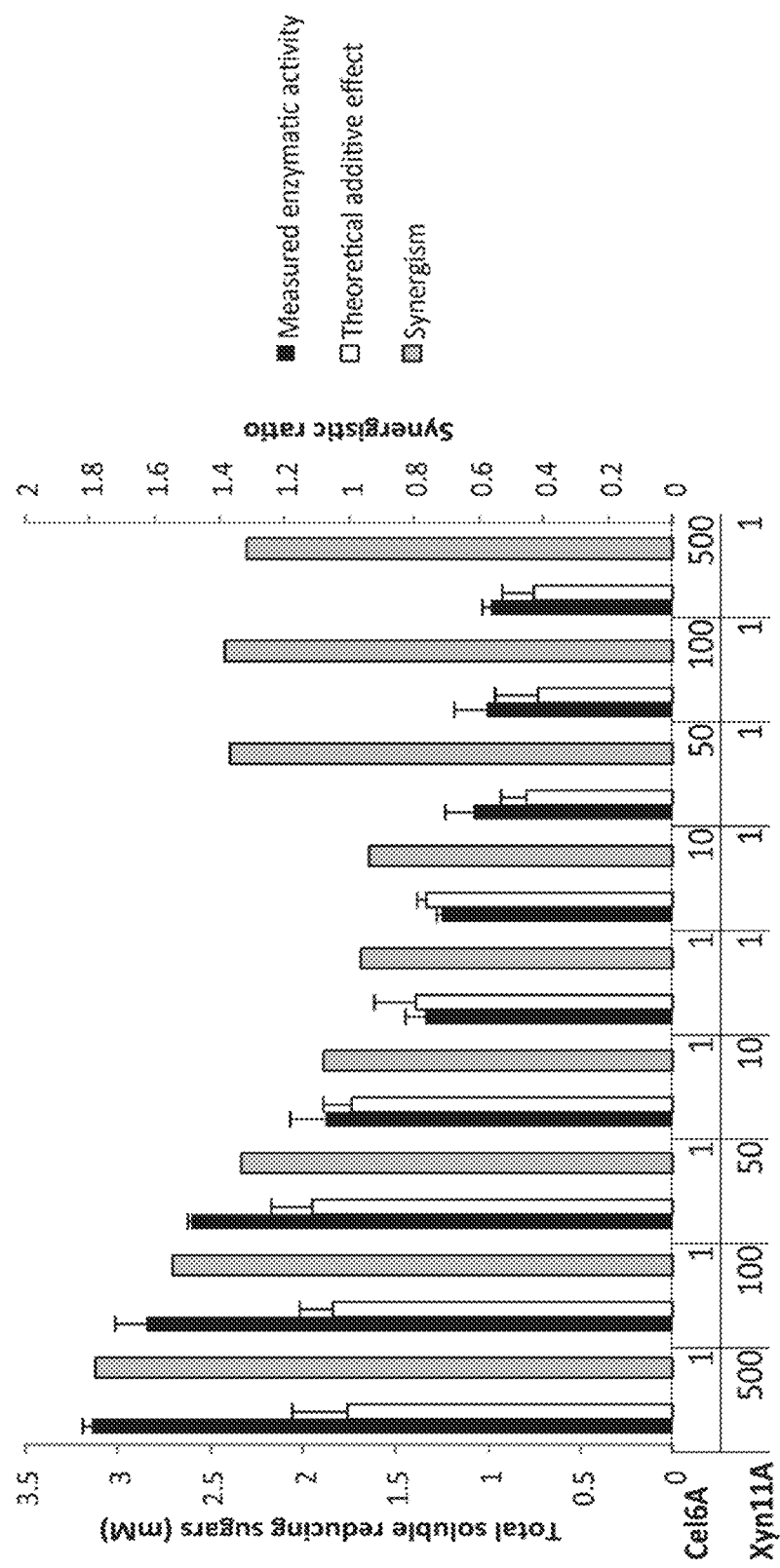
FIG. 5 is a bar graph illustrating enzymatic activity in supernatants of cocultures producing the cellulase and the xylanase. The substrate was pretreated wheat straw and the measured activities are compared with the corresponding theoretical additive effect. Cells were inoculated using various ratios (Ce16A/Xyn11A): 1/500, 1/100, 1/50, 1/10, 1/1, 10/1, 50/1, 100/1 and 500/1 (where the 10/1 cell ratio corresponds to an approximate 1:1 molar ratio of the secreted enzymes, since cellulase production is approximately 10-fold lower; see text and FIGS. 3A-D).

Whilst reducing the present invention to practice the present inventors generated two individual populations of lactic acid bacteria, the first being genetically engineered to express cellulase and the second being genetically engineered to express xylanase. The enzymatic activity of each individual population was confirmed on cellulose and xylan respectively (FIG. 4). When mixed together to form a two-strain cell-based consortium secreting both cellulase and xylanase, they exhibited synergistic activity in the overall release of soluble sugar from wheat straw (FIG. 5). Synergistic activities (>1) were observed for molar ratios of 1/5 and greater, in favor of bacteria secreting either enzyme. The highest overall activities and the largest synergistic effect were observed in reactions with a strong dominance of the Xyn11A-secreting strain, reaching a synergy factor of 1.8, and yielded up to 27.6% of available sugars.

The present inventors propose building on the backbone of the above described two-strain cell-based consortium by adding a third population of cells to generate a three-strain cell-based consortium, whereby the third strain is genetically modified to express enzymes of the ethanol pathway.

The present inventors further contemplate additional permutations of lactic acid bacterial populations which are capable of both breaking down lignocelluloses material and using the end-products of this reaction to generate ethanol therefrom.

Thus, according to one aspect of the present invention there is provided an article of manufacture comprising:

(i) a first population of lactic acid bacteria which are genetically modified to express at least one fibrolytic enzyme; and (ii) a second population of lactic acid bacteria which are genetically modified to produce ethanol from C5 or C6 sugars, wherein the first population of lactic acid bacteria and the second population of lactic acid bacteria are packaged in separate packaging.

Examples of lactic acid bacteria contemplated for use in the present invention include, but are not limited to *Lactobacillus plantarum, Lactococcus lactis, Leuconostoc mesenteroides, Streptococcus thermophilus, Pediococcus pentosaceus* and *Lactobacillus acidophilus*.

According to a particular embodiment, the lactic acid bacteria comprise *Lactobacillus plantarum*.

It will be appreciated that the isolated populations of the present invention are not necessarily pure populations and may comprise contaminating amounts of species or strains of additional bacteria.

Further, when a consortium of bacteria is described, (i.e. wherein the first population of bacteria is genetically modified in a different way to the second population of bacteria and optionally third population of bacteria), it will be appreciated that each of the populations may comprise an identical strain and/or species of bacteria or alternatively, the first and second (and optionally third) population may comprise different species/strains of bacteria.

As mentioned, the first population of bacteria is genetically modified to express a fibrolytic enzyme.

As used herein, the term "fibrolytic enzyme" refers to the class of enzyme that includes both cellulases and xylanases.

The term "cellulase" refers to both endoglucanases and exoglucanases. Endoglucanases randomly cleave cellulose chains into smaller units. Exoglucanases include cellobiohydrolases, which liberate glucose dimers (cellobiose) from the ends of cellulose chains; glucanhydrolases, which liberate glucose monomers from the ends of cellulose chains; and, beta-glucosidases, which liberate D-glucose from cellobiose dimers and soluble cellodextrins.

The term "exoglucanase", "exo-cellobiohydrolase" or "CBH" refers to a group of cellulase enzymes classified as E.C. 3.2.1.91. These enzymes hydrolyze cellobiose from the reducing or non-reducing end of cellulose. Exo-cellobiohydrolases include, but are not limited to, enzymes classified in the GH5, GH6, GH7, GH9, and GH48 GH families.

The term "endoglucanase" or "EG" refers to a group of cellulase enzymes classified as E.C. 3.2.1.4. These enzymes hydrolyze internal beta-1,4 glucosidic bonds of cellulose. Endoglucanases include, but are not limited to, enzymes classified in the GH5, GH6, GH7, GH8, GH9, GH12, GH44, GH45, GH48, GH51, GH61, and GH74 GH families.

The term "xylanase" refers to the class of enzymes which degrade the linear polysaccharide beta-1,4-xylan into xylose, thus breaking down hemicellulose, one of the major components of plant cell walls. Xylanases include those enzymes that correspond to Enzyme Commission Number 3.2.1.8. Xylanases include, but are not limited to, enzymes classified in the GH5, GH8, GH10, GH11 and GH43 GH families.

It will be appreciated that the first population of bacteria may comprise two sub-populations, the first sub-population being genetically modified to express a cellulase and the second sub-population being genetically modified to express a xylanase.

Alternatively, the first population of bacteria may be genetically modified to express at least two fibrolytic enzymes, the first being a cellulase and the second being a xylanase.

Some examples of suitable cellulase enzymes include, but are not limited to, those from the thermophilic bacteria *Thermobifida fusca* (DNA: SEQ ID NO:12, protein: SEQ ID NO:13), *Acidothermus cellulolyticus* (protein: SEQ ID NO:28), *Thermobispora bispora* (DNA: SEQ ID NO:29, protein: SEQ ID NO:30) and *Themomonospora curvata* (DNA: SEQ ID NO:31, protein: SEQ ID NO:32).

Some examples of suitable xylanase enzymes include, but are not limited to, those from the thermophilic bacteria

*Thermobifida fusca* (DNA: SEQ ID NO:14, protein: SEQ ID NO:15), *Clostridium clariflavum* (DNA: SEQ ID NO:18, protein: SEQ ID NO:19), *Clostridium thermocellum* (DNA: SEQ ID NO:20, protein: SEQ ID NO:21) *Thermobifida halotolerans* (DNA: SEQ ID NO:22, protein: SEQ ID NO:23) *Thermobispora bispora* (DNA: SEQ ID NO:24, protein: SEQ ID NO:25), *Thermopolyspora flexuosa* (DNA: SEQ ID NO:26, protein: SEQ ID NO:27).

The present invention further contemplates cellulases and xylanases from fiber-degrading bacteria that are the inhabitants of a ruminant's gut ecosystem. Such bacteria include *Ruminococcus flavefaciens* or *Ruminococcus albus*, the genome of strains of each of these species have already been sequenced and partially characterized [Rincon et al, 2010, PLoS ONE 5, e12476].

Alternative sources of appropriate enzymes from other mesophilic environmental (but non-ruminant) sources are also contemplated. These include enzymes from the following cellulosome-producing bacteria: *Acetivibrio cellulolyticus, Bacteroides cellulosolvens, Clostridium papyrosolvens* and *Clostridium cellulolyticum*.

As mentioned, the second population of bacteria is genetically modified to produce ethanol from C5 or C6 sugars.

In order to produce ethanol from C5 of C6 sugars the bacterial population of this aspect of the present invention may be genetically modified to express alcohol dehydrogenase and pyruvate decarboxylase.

The term "pyruvate decarboxylase" (pdc) refers to the enzyme that serves to direct the flow of pyruvate into acetaldehyde during fermentation. An exemplary pdc sequence is the *Z. mobilis* pdc described by Conway et al. (J. Bacteriol. 169 (3), 949-954 (1987)) and set forth as GenBank accession number AAA27696.

The term "alcohol dehydrogenase" refers to at least one of alcohol dehydrogenase A (adhA) alcohol dehydrogenase B (adhB) and alcohol dehydrogenase E (adhE) and refers to the enzymes that convert acetaldehyde to ethanol under fermentative conditions. An exemplary adhA sequence is the *Z. mobilis* adhA described by Keshav et al. (J. Bacteriol. 172 (5), 2491-2497 (1990)) and set forth as GenBank accession number AAA27682. An exemplary adhB sequence is the *Z. mobilis* adhB described by Conway et al. (J. Bacteriol. 169 (6), 2591-2597 (1987)) and set forth as GenBank accession number AAA27683. An exemplary adhE sequence is the *E. coli* adhE described by Fischer et al. (J. Bacteriol. 175 (21), 6959-6969 (1993)) and set forth as GenBank accession number CAA51344.

Thus, an example of a suitable alcohol dehydrogenase is from the *Zymomonas mobilis* (DNA: SEQ ID NO:33, protein: SEQ ID NO:34.

Another example of a DNA sequence encoding an optimized alcohol dehydrogenase is set forth in SEQ ID NO: 39.

An example of a suitable pyruvate decarboxylase is from the *Zymomonas mobilis* (DNA: SEQ ID NO:35, protein: SEQ ID NO:36) or from the *Sarcina ventriculi* (DNA: SEQ ID NO:37, protein: SEQ ID NO:38).

Another example of a DNA sequence encoding an optimized pyruvate decarboxylase is set forth in SEQ ID NO: 40.

The skilled person will appreciate that enzymes having sequences identical to those from a variety of additional sources may be used in the present invention.

Further, it will be appreciated that the sequences of the enzymes which are expressed in the lactic acid bacteria of the present invention do not necessarily have to be 100% homologous to the sequences from their source organisms.

Thus, enzymes which are expressed in the lactic acid bacteria of the present invention may be homologs and other modifications including additions or deletions of specific amino acids to the sequence (e.g., polypeptides which are at least 50%, at least 55%, at least 60%, at least 65%, at least 70%, at least 75%, at least 80%, at least 85%, at least 87%, at least 89%, at least 91%, at least 93%, at least 95% or more say 100% homologous to the native amino acid sequences of the source organisms, as determined using BlastP software of the National Center of Biotechnology Information (NCBI) using default parameters). The homolog may also refer to an ortholog, a deletion, insertion, or substitution variant, including an amino acid substitution, thereof and biologically active polypeptide fragments thereof.

Because the enzymes described herein are well known, and because of the prevalence of genomic sequencing, suitable enzymes (such as cellulases, xylanases alcohol dehydrogenases, pyruvate decarboxylases etc.) may be readily identified by one skilled in the art on the basis of sequence similarity using bioinformatics approaches.

It is well understood by one skilled in the art that many levels of sequence identity are useful in identifying polypeptides, from other species, wherein such polypeptides have the same or similar function or activity. Useful examples of percent identities include, but are not limited to: 24%, 30%, 35%, 40%, 45%, 50%, 55%, 60%, 65%, 70%, 75%, 80%, 85%, 90%, or 95%, or any integer percentage from 24% to 100% may be useful in describing the present invention, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%.

Bioinformatic approaches typically comprise the use of sequence analysis software which may be commercially available or independently developed. Typical sequence analysis software will include, but is not limited to: 1.) the GCG suite of programs (Wisconsin Package Version 9.0, Genetics Computer Group (GCG), Madison, Wis.); 2.) BLASTP, BLASTN, BLASTX (Altschul et al., J. Mol. Biol., 215:403-410 (1990)); 3.) DNASTAR (DNASTAR, Inc. Madison, Wis.); 4.) Sequencher (Gene Codes Corporation, Ann Arbor, Mish.); and 5.) the FASTA program incorporating the Smith-Waterman algorithm (W. R. Pearson, Comput. Methods Genome Res., [Proc. Int. Symp.] (1994), Meeting Date 1992, 111-20. Editor(s): Suhai, Sandor. Plenum: New York, N.Y.). Within the context of this application it will be understood that where sequence analysis software is used for analysis, that the results of the analysis will be based on the "default values" of the program referenced, unless otherwise specified. As used herein "default values" will mean any set of values or parameters that originally load with the software when first initialized.

Typically BLAST (described above) searching of publicly available databases with known cellulase/xylanase/alcohol dehydrogenase/pyruvate decarboxylase amino acid sequences, such as those provided herein, is used to identify the enzymes, and their encoding sequences, that may be used in the present strains.

Expression of heterologous enzymes such as cellulase, xylanase, alcohol dehydrogenase and pyruvate decarboxylase may be achieved by transforming suitable host cells with a polynucleotide sequence encoding the enzyme. Typically the coding sequence is part of a chimeric gene used for transformation, which includes a promoter operably linked to the coding sequence as well as a ribosome binding site and a termination control region. A chimeric gene is heterologous even if it includes the coding sequence for the enzyme from the host cell for transformation, if the coding sequence is combined with regulatory sequences that are not native to the natural gene encoding the enzyme.

As used herein the term "polynucleotide" refers to a single or double stranded nucleic acid sequence which is isolated and provided in the form of an RNA sequence, a complementary polynucleotide sequence (cDNA), a genomic polynucleotide sequence and/or a composite polynucleotide sequences (e.g., a combination of the above).

The term "isolated" refers to at least partially separated from the natural environment e.g., from a bacterial cell.

As used herein the term "transformation" refers to the transfer of a nucleic acid fragment into a host organism, resulting in genetically stable inheritance. Host organisms containing the transformed nucleic acid fragments are referred to as "transgenic" or "recombinant" or "transformed" organisms.

The term "promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

Codon degeneracy refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

Thus, codons may be optimized for expression based on codon usage in the selected host, as is known to one skilled in the art.

The term "codon-optimized" as it refers to genes or coding regions of nucleic acid molecules for transformation of various hosts, refers to the alteration of codons in the gene or coding regions of the nucleic acid molecules to reflect the typical codon usage of the host organism without altering the polypeptide encoded by the DNA.

Vectors useful for the transformation of a variety of host cells are common and described in the literature. Typically the vector contains a selectable marker and sequences allowing autonomous replication or chromosomal integration in the desired host. In addition, suitable vectors may comprise a promoter region which harbors transcriptional initiation controls and a transcriptional termination control region, between which a coding region DNA fragment may be inserted, to provide expression of the inserted coding region. Both control regions may be derived from genes homologous to the transformed host cell, although it is to be understood that such control regions may also be derived from genes that are not native to the specific species chosen as a production host.

The terms "plasmid" and "vector" as used herein, refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

Initiation control regions or promoters, which are useful to drive expression of a cellulase or xylanase coding region in ethanol are familiar to those skilled in the art. Some examples include the amy, apr, and npr promoters; nisA promoter (useful for expression Gram-positive bacteria (Eichenbaum et al. Appl. Environ. Microbiol. 64(8):2763-2769 (1998)); and the synthetic P11 promoter (useful for expression in *Lactobacillus plantarum*, Rud et al., Microbiology 152:1011-1019 (2006)). In addition, the ldhL1 and fabZ1 promoters of *L. plantarum* are useful for expression of chimeric genes in LAB. The fabZ1 promoter directs transcription of an operon with the first gene, fabZ1, encoding (3R)-hydroxymyristoyl-[acyl carrier protein] dehydratase.

Termination control regions may also be derived from various genes, typically from genes native to the preferred hosts. Optionally, a termination site may be unnecessary.

Vectors useful in lactic acid bacteria include vectors having two origins of replication and two selectable markers which allow for replication and selection in both *Escherichia coli* and lactic acid bacteria. An example is pFP996, which is useful in *L. plantarum* and other lactic acid bacteria (LAB). Many plasmids and vectors used in the transformation of *Bacillus subtilis* and *Streptococcus* may be used generally for lactic acid bacteria. Non-limiting examples of suitable vectors include pAM beta1 and derivatives thereof (Renault et al., Gene 183:175-182 (1996); and O'Sullivan et al., Gene 137:227-231 (1993)); pMBB1 and pHW800, a derivative of pMBB1 (Wyckoff et al. Appl. Environ. Microbiol. 62:1481-1486 (1996)); pMG1, a conjugative plasmid (Tanimoto et al., J. Bacteriol. 184:5800-5804 (2002)); pNZ9520 (Kleerebezem et al., Appl. Environ. Microbiol. 63:4581-4584 (1997)); pAM401 (Fujimoto et al., Appl. Environ. Microbiol. 67:1262-1267 (2001)); and pAT392 (Arthur et al., Antimicrob. Agents Chemother. 38:1899-1903 (1994)). Several plasmids from *Lactobacillus plantarum* have also been reported (e.g., van Kranenburg R, Golic N, Bongers R, Leer R J, de Vos W M, Siezen R J, Kleerebezem M. Appl. Environ. Microbiol. 2005 March; 71(3): 1223-1230).

Standard recombinant DNA and molecular cloning techniques used in the generation of vectors suitable for use in the present invention are well known in the art and are described by Sambrook, J., Fritsch, E. F. and Maniatis, T., Molecular Cloning: A Laboratory Manual, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., Experiments with Gene Fusions, Cold Spring Harbor Laboratory Press, Cold Spring Harbor, N.Y. (1984); and by Ausubel, F. M. et al., Current Protocols in Molecular Biology, published by Greene Publishing Assoc. and Wiley-Interscience (1987).

According to one embodiment, the fibrolytic enzymes expressed in the lactic acid bacteria are anchored to the cell wall.

According to still another embodiment, the fibrolytic enzymes expressed in the lactic acid bacteria are expressed as a secreted fusion protein together with a dockerin molecule. In this way, cellulosomes may be generated which comprise cell-anchored cellulase and xylanase.

The cellulosome complex is characterized by a strong bi-modular protein-protein interaction between "cohesin" and "dockerin" modules that integrates the various enzymes into the complex. The cohesin modules are part of "scaffoldin" subunits (non-enzymatic protein components), which incorporate the enzymes into the complex via their resident dockerins. The primary scaffoldin subunit also includes a carbohydrate (e.g., cellulose)-binding module (CBM) through which the complex recognizes and binds to the cellulosic substrate.

For details how to prepare such cellulosomes see for example Alber et al., 2009, Protein Sci 77, 699-709; Bayer et al., 2009, Biotechnology of lignocellulose degradation and biomass utilization (Sakka, K., Karita, S., Kimura, T., Sakka, M., Matsui, H., Miyake, H. & Tanaka, A., eds.), pp. 183-205. Ito Print Publishing Division, ISBN 978-4-9903-219-6-3 C-3845; Berg et al., 2009, PLoS ONE 4, e6650 and Maki et al., 2009, Int J Biol Sci. 2009; 5(5): 500-516.

Since the present invention contemplates that the cellulase and xylanase, that are expressed in the bacteria are secreted, typically the polynucleotides encoding the enzymes encode a pre-protein form of the enzymes.

According to a particular embodiment, the vector used for expressing the cellulase and the xylanase is based on the pSIP system which are further described in Sorvig et al., 2005, Microbiology 151:2439-2449; and Mathiesen G et al., Journal of applied microbiology 105:215-226. The present inventors further contemplate use of the pSIP system to express the alcohol synthesis enzymes as well.

The term "pre-protein" refers to a secreted protein with an amino-terminal signal peptide region attached. The signal peptide is cleaved from the pre-protein by a signal peptidase prior to secretion to result in the "mature" or "secreted" protein. The signal peptide may or may not be heterologous to the particular enzyme sequence.

Exemplary signal peptides include those that are derived from the *L. plantarum* WCFS1 proteins pLp_2145 s (SEQ ID NO: 16) and pLp_3050 s (SEQ ID NO: 17).

Vectors may be introduced into a host cell using methods known in the art, such as electroporation (Cruz-Rodz et al. Molecular Genetics and Genomics 224:1252-154 (1990), Bringel, et al. Appl. Microbiol. Biotechnol. 33: 664-670 (1990), Alegre et al., FEMS Microbiology letters 241:73-77 (2004)), and conjugation (Shrago et al., Appl. Environ. Microbiol. 52:574-576 (1986)). A chimeric gene can also be integrated into the chromosome of lactic acid bacteria using integration vectors (Hols et al., Appl. Environ. Microbiol. 60:1401-1403 (1990), Jang et al., Micro. Lett. 24:191-195 (2003)).

It will be appreciated that the method further comprises inactivating one or more genes encoding polypeptides that interfere with or otherwise reduce the amount of ethanol produced by the ethanol production genes. In accordance with the invention, such genes are inactivated by any of a number of means, well known to those of skill in the art, by which a gene is prevented from encoding its intended polypeptide or from encoding an active form of its intended polypeptide. Accordingly, such genes are inactivated by, for example, mutation, deletion, insertion, duplication, missense, frameshift, repeat, nonsense mutation, or other alteration or modification such that gene activity (i.e., transcription) is blocked or transcription results in functionally inactive polypeptides. In accordance with advantageous embodiments of the invention, genes are inactivated by deletion.

Thus, the recombinant bacteria may have a reduced, knocked-out, or no expression of additional enzymes including but not limited to pyruvate oxidase (EC 1.2.2.2), D-lactate dehydrogenase (EC 1.1.1.28; see, e.g., U.S. 20110230682, incorporated herein by reference), L-lactate dehydrogenase (EC 1.1.1.27), acetate kinase (EC 2.7.2.1), phosphate acetyltransferase (EC 2.3.1.8), citrate synthase (EC 2.3.3.1), phosphoenolpyruvate carboxylase (EC 4.1.1.31). The extent to which these manipulations are necessary is determined by the observed byproducts found in the bioreactor or shake-flask. For instance, observation of acetate would suggest deletion of pyruvate oxidase, acetate kinase, and/or phosphotransacetylase enzyme activities. In another example, observation of D-lactate would suggest deletion of D-lactate dehydrogenase enzyme activities, whereas observation of succinate, malate, fumarate, oxaloacetate, or citrate would suggest deletion of citrate synthase and/or PEP carboxylase enzyme activities.

In one embodiment, the present invention contemplates the use of combinations of populations of lactic acid bacteria, each population being genetically modified to express a different enzyme or set of enzymes. The different populations in a particular system may comprise identical strains of lactic acid bacteria. Thus, for example the first population of bacteria may comprise *L. plantarum* genetically modified to express a cellulase, a second population of bacteria may comprise *L. plantarum* genetically modified to express a xylanase and a third population of bacteria may comprise *L. plantarum* genetically modified to express enzymes of the ethanol biosynthesis pathway.

It will be appreciated also, that the different bacterial cell populations may or may not be pure populations (i.e. comprise a single strain of bacteria) but may be a mixed population of two or more strains of bacteria.

The particular cell populations may be provided in a single article of manufacture, each population being individually packaged.

In another embodiment of the present invention there is provided a population of lactic acid bacteria which have been genetically modified to secrete at least one fibrolytic enzyme (as described herein above) and in addition have been genetically modified to express enzymes of the ethanol biosynthesis pathway (as described herein above).

Cultures of the individual bacterial cell populations comprise a biomass composition and optionally a fermentation media.

As used herein, the term "biomass composition" refers to biological material which comprise cellulose and xylan (or other polymers that may be degraded to produce cellulose or xylan).

According to one embodiment, the biomass composition comprises cellulose and hemicellulose.

Cellulose is the most abundant polymer of the plant cell wall, constituting 30-40% of its content. Second are the hemicelluloses constituting 20-25%. Cellulose polymers are composed of D-glucose subunits attached in linear fashion by 13-(1-4) glycosidic bonds. The repeating dimers of glucose are named cellobiose and are considered as the basic cellulose subunits. Hemicellulose is composed of a versatile array of branched sugar polymers, among which xylan is the most abundant. Two units of D-xylose monomers attached by a β-(1-4) glycosidic bond constitute the basic subunit of xylan named xylobiose. In addition to these basic units, xlyan usually contains various sugar side chains attached to it. Together these two polymers make up most of the plant cell wall.

The biological material may be living or dead. The biomass composition may further include lignocelluloses, hemicellulose, lignin, mannan, and other materials commonly found in biomass. Non-limiting examples of sources of a biomass composition include grasses (e.g., switchgrass, *Miscanthus*), rice hulls, bagasse, cotton, jute, eucalyptus, hemp, flax, bamboo, sisal, abaca, straw, leaves, grass clippings, corn stover, corn cobs, distillers grains, legume plants, sorghum, sugar cane, sugar beet pulp, wood chips, sawdust, and biomass crops (e.g., *Crambe*). Sources of a biomass polymer may be an unrefined plant feedstock (e.g., ionic liquid-treated plant biomass) or a refined biomass polymer (e.g., beechwood xylan or phosphoric acid swollen cellulose). Additional sources of biomass composition include paper, paper products, paper waste, wood, particle board, sawdust, agricultural waste, sewage, silage, grasses, rice hulls, bagasse, jute, hemp, flax, bamboo, sisal, abaca, straw, corn cobs, corn stover, switchgrass, alfalfa, hay, coconut hair, cotton, seaweed, algae, and mixtures thereof.

In addition to the biomass material, the fermentation media may contain suitable minerals, salts, cofactors, buffers and other components, known to those skilled in the art, suitable for the growth of the cultures. Typically cells are grown at a temperature in the range of about 25° C. to about 40° C. in an appropriate medium. Suitable media for growing lactic acid bacteria are known in the art. Selection of a medium for growth of a particular bacterial strain will be known by one skilled in the art of microbiology or fermentation science. The use of agents known to modulate catabolite repression directly or indirectly, e.g., cyclic adenosine 2':3'-monophosphate, may also be incorporated into the fermentation medium.

An exemplary medium which may be used for propagating the genetically modified bacteria may comprise at least 10, at least 20, at least 30, at least 40, at least 50 or all of the components listed in Table 1 herein below—see for example Wegkamp et al, Letters in Applied Microbiology, 50 (2010) 57-64. Table 1 also provides exemplary concentrations of the components.

TABLE 1

| Medium component | g/l |
|---|---|
| $K_2HPO_4$ | 21.68 |
| $KH_2PO_4$ | 12.93 |
| Glucose | 11 |
| Sodium acetate (*3H$_2$O) | 1.0 (1.65) |
| Ammonium citrate | 0.6 |
| Ascorbic acid | 0.5 |
| Alanine | 0.24 |
| Arginine | 0.125 |
| Aspartic acid | 0.42 |
| Cysteine | 0.13 |
| Glutamate | 0.5 |
| Glycine | 0.175 |
| Histidine | 0.15 |
| Isoleucine | 0.21 |
| Leucine | 0.475 |
| Lysine | 0.44 |
| Methionine | 0.125 |
| Phenylalanine | 0.275 |
| Proline | 0.675 |

TABLE 1-continued

| Medium component | g/l |
|---|---|
| Serine | 0.34 |
| Threonine | 0.225 |
| Tryptophane | 0.05 |
| Tyrosine | 0.25 |
| Valine | 0.325 |
| 6,8-thiotic acid (α-lipoic acid) | 0.001 |
| Biotin | 0.0025 |
| Nicotinic acid | 0.001 |
| Panthothenic acid (Ca-pantothenate) | 0.001 |
| Para-aminobenzoic acid | 0.01 |
| Pyridoxamine | 0.005 |
| Pyridoxine | 0.002 |
| Riboflavin | 0.001 |
| Thiamine | 0.001 |
| Vitamin B12 | 0.001 |
| Adenine | 0.01 |
| Guanine | 0.01 |
| Inosine | 0.005 |
| Xanthine | 0.01 |
| Orotic acid | 0.005 |
| Thymidine | 0.005 |
| Uracil | 0.01 |
| $MgCl_2$ (*6H$_2$O) | 0.02 (0.426) |
| $CaCl_2$ (*2H$_2$O) | 0.05 (0.066) |
| $MnCl_2$ (*2H$_2$O) | 0.016 (0.02) |
| $FeCl_3$ (*6H$_2$O) | 0.003 (0.005) |
| $FeCl_2$ (*4H$_2$O) | 0.005 (0.0078) |
| $ZnSO_4$ | 0.005 |
| $CoSO_4$ ($CoCl_2$*6H$_2$O) | 0.0025 (0.003) |
| $CuSO_4$ | 0.0025 |
| $(NH_4)_6Mo_7O_{24}$ (*4H$_2$O) | 0.0025 (0.0026) |

Suitable pH ranges for the fermentation are between pH 4.5 to pH 7.0, where pH 5.0 to pH 6.0 is preferred as the initial condition.

Fermentations may be performed under aerobic or anaerobic conditions, where anaerobic or microaerobic conditions are preferred.

The relative ratio of each of the populations in the culture is selected such that the specific activity of cellulase:xylanase in the culture is greater than 4:1 or less than 1:4.

According to a specific embodiment, the specific activity of cellulase:xylanase in the culture is greater than 4:1.

According to a specific embodiment, the specific activity of cellulase:xylanase in the culture is greater than 5:1.

According to a specific embodiment, the specific activity of cellulase:xylanase in the culture is greater than 6:1.

According to a specific embodiment, the specific activity of cellulase:xylanase in the culture is greater than 7:1.

According to a specific embodiment, the specific activity of cellulase:xylanase in the culture is greater than 8:1.

According to a specific embodiment, the specific activity of cellulase:xylanase in the culture is greater than 9:1.

According to a specific embodiment, the specific activity of cellulase:xylanase in the culture is greater than 10:1.

According to a specific embodiment, the specific activity of cellulase:xylanase in the culture is greater than 20:1.

According to a specific embodiment, the specific activity of cellulase:xylanase in the culture is greater than 30:1.

According to a specific embodiment, the specific activity of cellulase:xylanase in the culture is greater than 40:1.

According to a specific embodiment, the specific activity of cellulase:xylanase in the culture is greater than 50:1.

According to a specific embodiment, the specific activity of xylanase:cellulase in the culture is greater than 4:1.

According to a specific embodiment, the specific activity of xylanase:cellulase in the culture is greater than 5:1.

According to a specific embodiment, the specific activity of xylanase:cellulase in the culture is greater than 6:1.

According to a specific embodiment, the specific activity of xylanase:cellulase in the culture is greater than 7:1.

According to a specific embodiment, the specific activity of xylanase:cellulase in the culture is greater than 8:1.

According to a specific embodiment, the specific activity of xylanase:cellulase in the culture is greater than 9:1.

According to a specific embodiment, the specific activity of xylanase:cellulase in the culture is greater than 10:1.

According to a specific embodiment, the specific activity of xylanase:cellulase in the culture is greater than 20:1.

According to a specific embodiment, the specific activity of xylanase:cellulase in the culture is greater than 30:1.

According to a specific embodiment, the specific activity of xylanase:cellulase in the culture is greater than 40:1.

According to a specific embodiment, the specific activity of xylanase:cellulase in the culture is greater than 50:1.

The term "specific activity" as used herein refers to the amount of substrate consumed and/or product produced in a given time period and per defined amount of protein at a defined temperature.

The culture of the present invention may also comprise enzymes capable of degrading lignin. Such enzymes include phenol oxidases such as lignin peroxidases (LiP), manganese peroxidases (MnP) and laccases which may be comprised in white-rot fungi such as *P. chrysosporium, Pleurotus ostreatus* and *Trametes versicolor*. Laccase has broad substrate specificity and oxidises phenols and lignin substructures with the formation of oxygen radicals. Other enzymes that participate in the lignin degradation processes are $H_2O_2$-producing enzymes and oxido-reductases, which can be located either intra- or extracellularly. Bacterial and fungal feruloyl and p-coumaroyl esterases are relatively novel enzymes capable of releasing feruloyl and p-coumaroyl and play an important role in biodegradation of recalcitrant cell walls in grasses.

Cells of the invention may have a specific xylose degradation rate of at least about 200, about 250, about 300, about 346, about 350, about 400, about 500, about 600, about 750, or about 1000 mg xylose/g cells/h.

According to one embodiment, the cells may have a xylose conversion yield of at least 1 to 29%.

Cells of the invention may have a specific cellulose degradation rate of at least about 200, about 250, about 300, about 346, about 350, about 400, about 500, about 600, about 750, or about 1000 mg cellulose/g cells/h.

According to one embodiment, the cells may have a cellulose conversion yield of at least 1 to 8%.

The cell of the invention may have a yield of ethanol on lignocellulose (or its composing sugars) that is at least about 40, about 50, about 55, about 60, about 70, about 80, about 85, about 90, about 95 about 98 or about 99% of the host cell's yield of ethanol.

The cultures of the present invention may be used in a fermentation process for generating ethanol.

The fermentation process may be an aerobic or an anaerobic fermentation process. An anaerobic fermentation process is herein defined as a fermentation process run in the absence of oxygen or in which substantially no oxygen is consumed, preferably less than about 5, about 2.5 or about 1 mmol/L/h, more preferably 0 mmol/L/h is consumed (i.e. oxygen consumption is not detectable), and wherein organic molecules serve as both electron donor and electron acceptors. In the absence of oxygen, NADH produced in glycolysis and biomass formation, cannot be oxidised by oxidative phosphorylation. To solve this problem many microorganisms use pyruvate or one of its derivatives as an electron and hydrogen acceptor thereby regenerating $NAD^+$.

A preferred process is a process for the production of an ethanol, whereby the process comprises the steps of: (a) fermenting a medium containing a source of cellulose and/or hemicellulose with a modified host cell as defined above, whereby the host cell ferments cellulose and/or hemicellulose to ethanol; and optionally, (b) recovery of the ethanol. The fermentation medium may also comprise a source of glucose that is also fermented to ethanol. In the process the volumetric ethanol productivity is preferably at least about 0.5, about 1.0, about 1.5, about 2.0, about 2.5, about 3.0, about 5.0 or about 10.0 g ethanol per liter per hour. The ethanol yield on cellulose and/or hemicellulose in the process preferably is at least about 50, about 60, about 70, about 80, about 90, about 95 or about 98%. The ethanol yield is herein defined as a percentage of the theoretical maximum yield.

A process of the invention may also comprise recovery (i.e. isolation) of the ethanol.

Confirmation of the production of ethanol may be performed using a high-performance liquid chromatography (HPLC) system. Thus for example, metabolites may be separated on a column (e.g. Phenomenex) under isocratic temperature (e.g. 65° C.) and flow (0.8 ml/min) conditions in 2.5 mM $H_2SO_4$ and then passed through a refractive index (RI) detector. Identification may be performed by comparison of retention times with standards.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Material and Methods

Cloning:

Wild-type enzymes Ce16A and Xyn11A were cloned from *Thermobifida fusca* genomic DNA as described previously (21, 22). The enzyme constructs in pET28a were designed to contain a His-tag for subsequent purification.

For expression and secretion in *L. plantarum*, the glycoside hydrolases were cloned in the modular secretion plasmids pLp_2145 sAmy and pLp_3050 sAmy (15) by replacing the amylase gene in these plasmids by an appropriately amplified gene fragment, using either SalI or XhoI (SalI is compatible with XhoI) and HindIII restriction sites. For this purpose the Ce16A-encoding gene was amplified using the forward primer 5'-tcttCTCGAGatggcatccccagacctct-3' (SEQ ID NO: 1) and reverse primer 5'-aatAAGCTTtcagctg-gcggcgcaggtaag-3'(SEQ ID NO: 2) (XhoI and HindIII sites in capital letters). The Xyn11A-encoding gene amplified cloned using 5'-tcttGTCGACatggccgtgacctccaacgag-3' (SEQ ID NO: 3) and 5'-aatAAGCTTctagttggcgctgcaggaca-3' (SEQ ID NO: 4) primers (SalI and HindIII sites in capital letters). The pLp_2145 s constructs are referred to as Lp1, whereas the pLP_3050 s containing constructs are referred to as Lp2.

pLp_2145 sAmy and pLp_3050 sAmy are part of the pSIP400 series (13). As a control the two enzymes were also cloned into pSIP407 (referred to as No-Lp), which contains the same replicon and promoter as Lp1 and Lp2 but lacks a leader peptide (13). To make these constructs, the pepN gene present in pSIP407 was replaced by an NcoI-XbaI fragment containing the ce16A gene or a BspHI-XbaI fragment containing the xyn11A gene, which leads to the gene being translationally fused to the promoter (BspHI is compatible with NcoI). For this purpose the Ce16A-encoding gene was amplified using the forward primer 5'-atatatCCATGGatg-gcatccccagacctcttcgc-3'(SEQ ID NO: 5) and reverse primer 5'-atatatTCTAGAtcactccaggctggcggcgcagg-3' (SEQ ID NO: 6; NcoI and XbaI sites in capital letters). The Xyn11A-encoding gene amplified cloned using 5'-tcagtcTCAT-GAatggccgtgacctccaacgagaccgg-3' (SEQ ID NO: 7) and 5'-agcgtaTCTAGActagttggcgctgcaggacacc-3' primers (SEQ ID NO: 8; BspHI and XbaI sites in capital letters).

For generation of empty pLP_2145 s and pLP_3050 s, the Amy gene was excised using SalI and EcoRI restriction enzymes. The linearized plasmid was purified and blunted using Quick Blunting Kit (NEB, MA, USA). Blunt fragments were self-ligated to create the empty plasmids.

PCR reactions were performed using Phusion High Fidelity DNA polymerase F530-S(New England Biolabs, Inc), and DNA samples were purified using a HiYield™ Gel/PCR Fragments Extraction Kit (Real Biotech Corporation, RBC, Taiwan). Restrictions enzymes were purchased from New England Biolabs (Beverly, Mass.) and the T4 DNA ligase from Fermentas (Vilnius, Lithuania). *L. plantarum* plasmids were sub-cloned in *E. coli* TG1 competent cells (Lucigen Corporation, WI, USA). *L. plantarum* strain WCFS1 was transformed according to the protocol of Aukrust et al (23). Antibiotics used for positive clone selection and added in media were 10 µg/ml and 200 µg/ml erythromycin for *L. plantarum* and *E. coli*, respectively.

Protein Expression in *E. coli*, and Purification:

The plasmids pCe16A and pXyn11A were expressed in *E. coli* BL21 (lDE3) pLysS cells and the His-tagged enzymes were purified on a Ni-NTA column (Qiagen), as reported earlier (24). Purity of the recombinant proteins was tested by SDS-PAGE on 10% acrylamide gels, and fractions containing the pure recombinant protein were pooled and concentrated using Amicon centrifugal filters (Millipore, France). Protein concentrations were determined by measuring absorbance at 280 nm, using theoretical extinction coefficients calculated with the Protparam tool. Proteins were stored in 50% (v/v) glycerol at −20° C.

Activity Assay for the Pure Enzymes:

The activity of purified recombinant Ce16A and Xyn11A were tested in reactions containing 0.5 µM of enzyme and 7.5 g/l phosphoric acid-swollen cellulose (PASC, prepared as described by Lamed et al (25)) or 2% oat spelt xylan (Sigma Chem. Co, St. Louis Mo.) in 50 mM citrate buffer pH 5 or 6. Samples were incubated 30 min at 37 or 50° C., cooled to 0° C. by placing on ice, and then centrifuged 5 min at 14000 rpm at 4° C. The amount of soluble reducing sugars in the supernatants was determined by the DNS method as described below.

Protein Expression in *L. plantarum*:

Freshly inoculated cultures of *L. plantarum* WCFS1 harboring a pSIP-derived expression plasmid was grown at 37° C. in MRS broth (BD Difco™, Franklin Lakes, N.J., USA) containing 10 µg/ml erythromycin). Gene expression was induced at an $OD_{600}$ of 0.3 by adding the inducing peptide for sakacin P production (Casio Laboratory, Denmark) (26) to a final concentration of 25 ng/ml and incubated for another 3 h at 37° C. For co-culture experiments, strains producing either the cellulase or the xylanase, respectively, were mixed at equal ODs or at various ratios and then grown and induced in the same manner.

Western-Blot:

Proteins from the culture supernatants were separated on SDS-PAGE gels (10% acrylamide) and transferred to a nitrocellulose membrane using Trans-Blot® Cell Mini (Bio-Rad Laboratories Ltd, Israel). Non-specific protein interactions were blocked by incubating the membrane for 1 h with 5% BSA (prepared in Tris Buffer Saline-Tween 20, TBS-T). The membrane was then rinsed twice (1 min) with TBS-T. Rabbit antibody against each enzyme (prepared by Sigma, Israel) was incubated with the appropriate membrane for 1 h in TBS-T, containing 1% BSA. The membrane was again rinsed twice (1 min) with TBS-T and then incubated for 1-h with secondary antibody, mouse anti-rabbit horseradish peroxidase (HRP), at a dilution of 1:10000. The membrane was rinsed as described above and then rinsed twice (30 min) with TBS+1% Triton X-100. Blots were developed by incubating the membrane 1 min with equal amounts of solution A & B of ECL (Ornat, Israel). Chemiluminescence was quantified using a luminescent image analyser, ImageQuant LAS 4000 Mini (Danyel Biotech, Israel).

Dot-Blot:

A volume of 50 ml cultures at $OD_{600}$=1, expressing the Ce16A enzyme (Lp1, Lp2 or No-Lp) was concentrated 50 times using Amicon centrifugal filters (Millipore, France). For the Xyn11A enzyme, 1 ml of each culture at $OD_{600}$=1 (Lp1, Lp2 or No-Lp) was dialyzed in TBS to remove MRS media. Purified enzymes were blotted in concentrations ranging from 0.5-20 nM for the cellulase or 0.1-10 nM for the xylanase by applying 2 µl of an appropriate solution (in TBS) to a nitrocellulose membrane (Whatman). Concentrated and/or dialyzed culture supernatants were blotted by applying 2 µl of cultures. The above-described protocol for the Western blot was then followed.

Congo-Red Assay:

The protocol of Anbar was followed with modifications (27). Oat spelt xylan (0.3%) was used instead of carboxymethyl cellulose (CMC) for xylanase activity detection. Transformed *L. plantarum* cells were spread onto MRS plates containing erythromycin (10 µg/mL) and incubated overnight at 37° C. The plates were overlaid with 20 ml soft agar containing 0.3% (w/v) CMC or oat spelt xylan (for cellulase or xylanase activity detection), 0.7% agar and 200 µl of 0.1 µg/ml pSIP induction peptide in citrate buffer (25 mM, pH 5.0). The plates were incubated for 2 h at 37° C. to induce enzyme expression and activity. The plates were then stained for 10 min with fresh Congo red solution (0.25%) and destained in 1 M NaCl. Formation of halos around the colonies indicated production of endoglucanase or endoxylanase activity.

Activity Assay:

PASC degradation was assayed by mixing pure recombinant Ce16A varying from 0 to 100 nM (final concentration) or a volume of 30 µl of concentrated supernatants of the cultures (as described above) with 150 µl of 7.5 g/l phosphoric acid swollen cellulose PASC) in a final volume of 200 µl 50 mM acetate buffer pH 5.0. Samples were incubated at 37° C. for 18 h, and the reactions were terminated by immersing the sample tubes in ice water. The samples were then centrifuged 2 min at 14000 rpm to remove the substrate.

The xylanase assay mixture consisted of 100 µl buffer (50 mM citrate buffer pH 6.0) with purified Xyn11A enzyme (0-5 nM) or a volume of 30 µl of dialyzed supernatants of the cultures in 50 mM of the same buffer. The reaction was commenced by adding 100 µl of 2% oat spelt xylan, and continued for 2 hours at 37° C. The reaction was stopped by transferring the tubes to an ice-water bath followed by centrifugation for 2 min at 14000 rpm.

Wheat straw (0.2-0.8 mm) provided by Valagro (Poitiers, France) was washed as described previously (28, 29). The material was then subjected to sodium hypochlorite (12%) pretreatment at room temperature for 1 h (30). The degradation assay was conducted in 200 µl 50 mM acetate/citrate buffer pH 5-6.0 containing 3.5 g/l of pretreated wheat straw and 30 µl of concentrated or dialyzed culture supernatants. In the case of supernatants from co-cultures (50 ml at $OD_{600}$=1) of strains secreting the Ce16A and Xyn11A enzymes, were concentrated 50 times using Amicon centrifugal filters (Millipore, France). Reactions were incubated for 24 h at 37° C.

All assays were performed in triplicate. Enzymatic activity was determined quantitatively by measuring the soluble reducing sugars released from the polysaccharide substrates by the dinitrosalicyclic acid (DNS) method (31, 32). DNS solution (150 µl) was added to 100 µl of sample, and after boiling the reaction mixture for 10 min, absorbance at 540 nm was measured. Sugar concentrations were determined using a glucose standard curve.

Evaluation of Synergism:

For determination of theoretical enzymatic activity in co-cultures (additive effect), enzymatic activities were calculated from two different assays. In each assay, a coculture of one of the enzyme-secreting strains together with the respective empty plasmid-bearing control strain was grown (and induced as described above), and its supernatant was analyzed for enzymatic activity. The theoretical additive activity was calculated by computing the sum of activities for each of the individually measured enzymes. For example, for the 1/500 ratio, one volume of the Ce16A-secreting strain (Lp1) and 500 volumes of the empty pLp_3050 s plasmid-bearing strain (as a replacement for the Xyn11A-secreting strain (Lp2)) were cocultured. In parallel, one volume of the empty pLp_2145 s plasmid-bearing strain (as a replacement for the Ce16A-secreting strain (Lp1)) and 500 volumes of the Xyn11A-secreting strain (Lp2) were cocultured. The enzymatic activities on wheat straw substrate of 30 µl of concentrated supernatants (as described above for the coculture experiments) from each of the cocultures were determined individually, added together and defined as the theoretical additive effect. These values were then compared with those of the corresponding combined cocultures of the cellulase- and xylanase-secreting strains.

Plasmid Extraction:

Cocultures of cellulase- and xylanase-secreting strains were grown as described above. At $OD_{600}$=1, cells were pelleted from 5 ml of culture by centrifugation at 5000 g for 10 min at 4° C. and resuspended in 200 µl of PD1 buffer of a High-Speed Plasmid Mini Kit (Geneaid, New Taipei City, TW). Lysozyme was added to the suspensions to a final concentration of 3 mg/ml. Suspensions were incubated at 37° C. for 15 min and then subjected to five freeze-thaw cycles as follows: the samples were submerged in liquid nitrogen for 3 min, transferred to 70° C. water bath for an additional 3 min and then mixed gently but thoroughly. Following this step, the protocol was carried out according to the manufacturer's instructions.

Real-Time PCR:

Quantitative real-time PCR analysis was performed to verify the ratios between the cellulase- and xylanase-secreting strains in the bacterial consortium. A specific fragment of each plasmid (140 and 124 bp for pLP_2145 s and pLP_3050 s respectively) was amplified using the forward primer 5'-ATTTAGCTGGCTGGCGTAAAGTATG-3' (SEQ ID NO: 9) for both plasmids, and the reverse primers 5'-TCATTTCAGGATTGATCATTGTTGC-3' (SEQ ID NO: 10) for pLP_2145 s (Lp1) and 5'-GACGACCCCGAAGA-CACAACTAG-3' (SEQ ID NO: 11) for pLP_3050 s (Lp2). Individual standard curves suitable for the quantification of each plasmid were generated by amplifying serial 10-fold dilutions of quantified gel-extracted PCR products obtained by the amplification of each fragment. The standard curves were obtained using four dilution points and were calculated using Rotorgene 6000 series software (Qiagen, Hilden, Germany). Subsequent quantifications were calculated with the same program using the standard curves generated. As positive control, one purified product with known concentration that was used for the standard curve was added to each quantification reaction. This also served to assess the reproducibility of the reactions and to fit the results to the standard curve. Two negative controls were performed; the first contained the purified product of one of the plasmids and the primers of the other. This was done in order to eliminate the possibility of primers cross-reactivity. The second control did not contain any DNA template. All obtained standard curves met the required standards of efficiency ($R^2$>0.99, 90%<E<115%). The number of copies of each plasmid in the cultures was assessed and the ratio between the plasmids was determined. Real-time PCR was performed in a 10 µl reaction mixture containing 5 µl Absolute Blue SYBR Green Master Mix (Thermo Scientific, MA, USA), 0.5 µl of each primer (10 µM working concentration), 2 µl nuclease-free water and 2 µl of 10 ng/µl DNA template. Amplification involved one hold cycle at 95° C. for 15 min for initial denaturation and activation of the hot-start polymerase system, and then 30 cycles at 95° C. for 10 s followed by annealing for 20 s at 53.3° C. and extension at 72° C. for 20 s. To determine the specificity of amplification, a melting curve of PCR products was monitored by slow heating with fluorescence collection at 1° C. increments from 45 to 99° C.

Results

Choice of Lignocellulolytic Enzymes.

The selected enzymes for *L. plantarum* transformation originate from the very well-characterized cellulolytic bacterium *Thermobifida fusca*. This bacterium produces a set of only six cellulases and four xylanases. These moderately thermophilic enzymes are known to have a broad temperature-activity and pH-activity (37), which might be compatible with the conditions expected during a *Lactobacillus* fermentation.

Figure 1A:
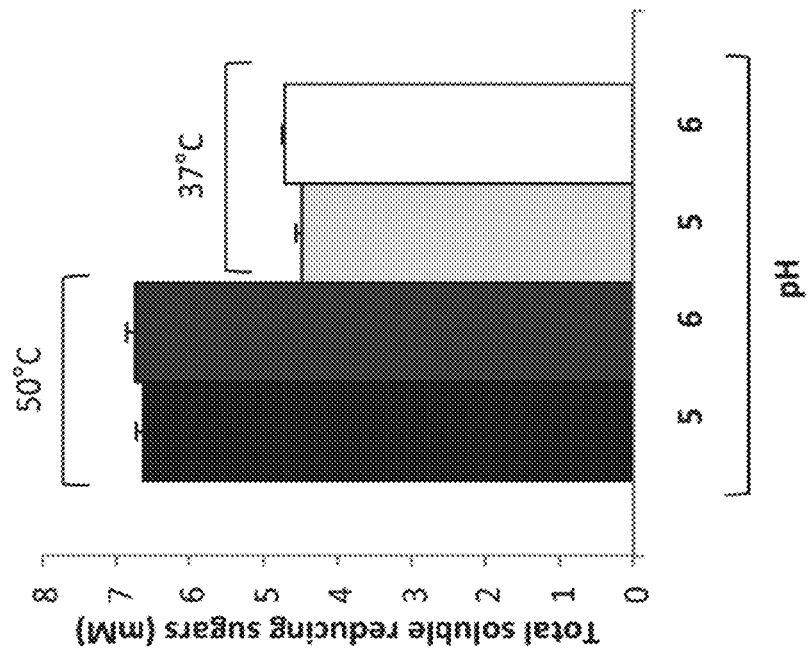
FIGS. 1A-B are bar graphs illustrating the comparative enzymatic activity of purified recombinant Ce16A (A) and Xyn11A (B) enzymes on PASC or xylan, at 37° C. or 50° C. and at pH 5 or 6. Enzymatic activity is defined as mM total reducing sugars following a 30-min reaction period. Each reaction was performed in triplicate, and standard deviations are indicated.
Figure 1B:
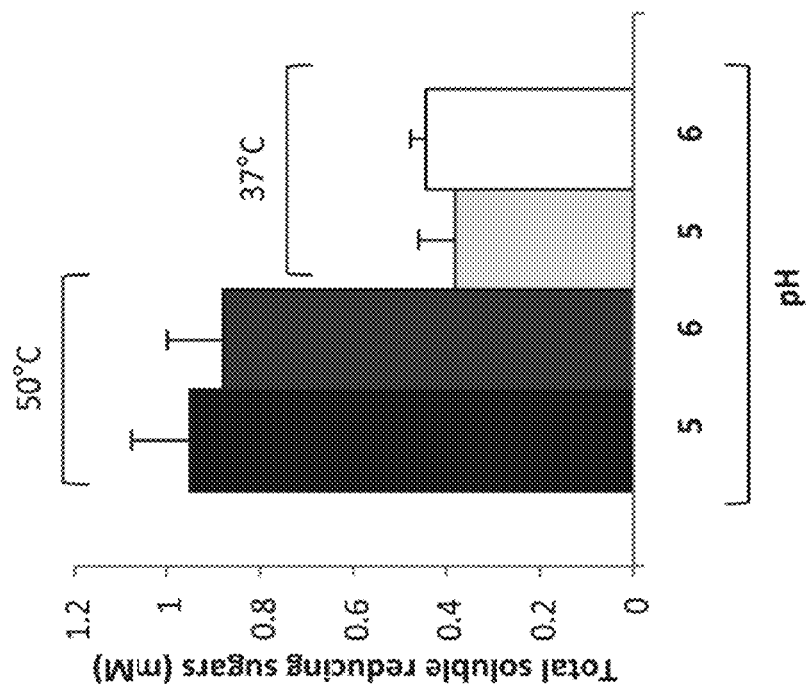

For initial studies, we focused on the *T. fusca* endoglucanase Ce16A, which is highly induced by cellobiose (38), and endoxylanase Xyn11A, which is the most abundant xylanase produced during growth on xylan (39). In addition to their catalytic modules, Ce16A has a C-terminal family 2 CBM which binds selectively to cellulose, and Xyn11A contains a C-terminal family 2 CBM that binds both cellulose and xylan. The molecular masses of the enzymes are 46,980 Da and 33,168 Da for Ce16A and Xyn11A, respectively. The selection of Ce16A and Xyn11A was also based on their simple modular architecture and their considerable residual activity under acidic conditions (activity at pH 5.0 is >90% of that at pH 6) and at 37° C. (~40% and ~70% of the activity at 50° C., for Ce16A and Xyn11A, respectively) (FIGS. 1A-B) consistent with normal growth of *L. plantarum*.

Enzyme Secretion by *L. plantarum*.

Figures 2A, 2B:
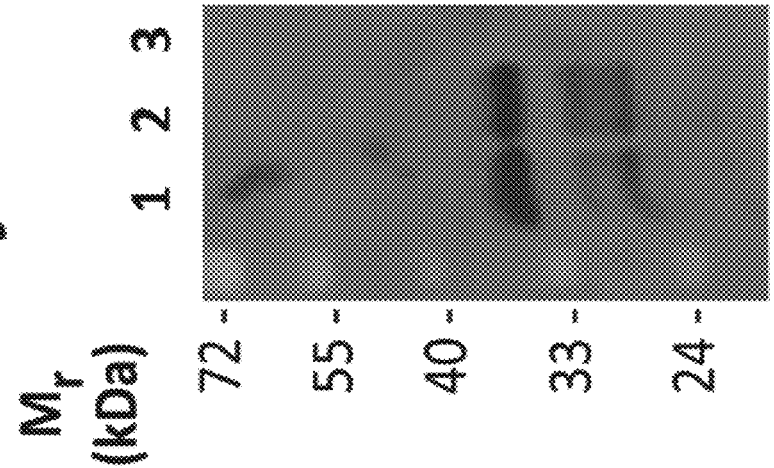
FIGS. 2A-B are photographs of Western-blot analysis of culture supernatants from transformed lactobacilli. A. Lanes 1 to 3: Ce16A expressed with the Lp1, Lp2 and No-Lp plasmids, respectively. B. Lanes 1 to 3: Xyn11A expressed with the Lp1, Lp2 and No-Lp plasmids, respectively. The calculated masses of secreted Ce16A and Xyn11A are 46.9 kDa and 33.2 kDa, respectively. The lane of the prestained molecular weight markers in Panel A was manually inserted as a reference onto the chemiluminescent image of the blot.

The presence of secreted enzymes in the culture medium was observed by Western Blotting using specific antibodies against each enzyme (FIGS. 2A-B). The enzymes were visible in the extracellular fraction of the strains carrying the Lp1 and Lp2 secretion plasmids, and the observed bands corresponded well to their theoretical masses. Degradation products, i.e. smaller bands, were also observed. No extracellular enzymes were detected in the supernatants of strains carrying the expression plasmid lacking the secretion peptide (FIGS. 2A-B, lane 3).

Extracellular cellulase and xylanase activities in transformed colonies were detected by the Congo-Red method (data not shown) and by activity assays of culture supernatants (FIGS. 3A-D; see below). Control cultures with intracellular expression of the respective enzymes did not exhibit any activity using the Congo-Red assay and their supernatants did not show hydrolytic activity on xylan or PASC.

The concentrations of the secreted enzymes in the different cultures were calculated by comparing the extracellular fraction to serial dilutions of purified enzymes, either by dot blot analysis or by measuring reducing sugar formation on PASC or xylan substrates. The cellulase concentrations at $OD_{600}$=1 were estimated at 0.33 nM and 0.27 nM for the Lp1 and Lp2 secretion plasmids, respectively. For the xylanase these values were estimated 2.7 nM and 3.3 nM, respectively (FIG. 3C, D). The concentrations, calculated either by the dot-blot quantification or enzymatic activity method, were similar for both enzymes, suggesting that the major portion of the secreted enzymes is functional and that the expression and secretion processes do not substantially affect their activity. The culture supernatants retained full cellulase/xylanase activity after storage for several days at 4° C. without added protease inhibitors.

The fact that culture supernatants from strains with intracellular expression did not exhibit enzymatic activity (FIGS.

3 C and D), indicates that the detected activities for the Lp1 and Lp2 constructs reflect properly secreted enzymes and do not originate from cell lysis.

Wheat Straw Degradation:

Prior to enzymatic degradation, wheat straw was subjected to chemical pretreatment with sodium hypochlorite that served to reduce the lignin content while preserving the cellulose/hemicellulose fractions in order to promote enzymatic degradation. The chemical composition of the pretreated wheat straw was 63% cellulose, 31% hemicellulose and 3% lignin (30). Both the secreted cellulase and the secreted xylanase exhibited enzymatic activity on the pretreated wheat straw (FIG. 4).

Supernatants of cocultures of a Ce16A-secreting strain (Lp1) and a Xyn11A-secreting strain (Lp2) exhibited activity when incubated on wheat straw (FIG. 5). Synergistic activities (>1) were observed for ratios of 1/50 and greater, in favor of bacteria secreting either enzyme. The highest overall activities and the largest synergistic effect were observed in reactions with a strong dominance of the Xyn11A-secreting strain and yielded up to 27.6% of available sugars (FIG. 5), suggesting that xylan degradation by Xyn11A is a faster process than cellulose degradation by Ce16A. This observation further suggests that xylan degradation is more beneficial for cellulose accessibility than cellulose degradation is for xylan accessibility. RT-PCR of the different plasmids at the end of the growth period revealed that the ratios of the bacterial strains remained similar to the inoculation ratios (FIG. 6), thus indicating that expression and secretion of the two proteins did not have a differential effect on the growth rates of the bacteria.

Discussion

In this Example, the successful production and secretion of a cellulase and a xylanase by *Lactobacillus plantarum* is disclosed. Despite using identical cloning strategies, the enzymes were produced at different levels. An optimized cell consortium comprising two of the resulting strains was established using the efficiency of wheat straw degradation as the output parameter. These results provide a proof of principle for the engineering of lactobacilli for advanced biomass conversions. The *T. fusca* enzymes exhibit temperature optima ranging from 50-60° C., but were nevertheless selected to their considerable residual activities at 37° C. and pH 5 (FIGS. 1A-B), i.e conditions that are common in *L. plantarum* cultures.

As a first step towards more complex biotransformations, the present inventors studied co-cultures of recombinant bacteria secreting the two enzymes. This approach was possible because the expression of the heterologous enzymes did not affect the bacterial growth, meaning that strain ratios remained rather stable during the growth period.

An advantage of using cocultures is that a cell consortium can easily be optimized by adjusting the ratio of each cell type during inoculation. In a recent publication, a mixture of *S. cerevisiae* cells with an optimized endoglucanase:exoglucanase:β-glucosidase ratio produced 1.3 fold more ethanol than cells composed of an equal amount of each cell type, suggesting the usefulness of a consortium of bacteria for lignocellulose bioprocessing (44). Such an approach can also be used to balance production levels, which may differ, as observed for Ce16A and Xyn11A in the present study.

The transformed *L. plantarum* cells were able to degrade either xylan or cellulose and wheat straw. Interestingly, co-culturing revealed clear synergistic effects with the synergy factor reaching 1.8 for combinations with a large excess of the xylanase. These results suggest that the action of the xylanase in deconstructing the substrate renders the cellulose accessible to the cellulase, as described in previous studies (45-47).

Several studies on other bacteria illustrate that *L. plantarum* producing these lignocellulolytic enzymes could have attractive applications. For example, integration of a cellulase from *Bacillus* sp. ATCC 21833 into the genome of *L. plantarum* led to increased efficiency in alfalfa silage fermentation (48). A similar result was reported for *L. lactis* strains transformed with a *Neocallimastix* sp. cellulase (49). The expression of genes coding for fibrolytic enzymes in lactobacilli is also of interest for the development of intestinal probiotic strains (50-52). Recently, co-expression of a β-glucanase and a xylanase in *L. reuteri* has been reported (52), and the transformed strain exhibited enzymatic activity on soluble β-glucan and xylan.

Providing *L. plantarum* cells with highly secreted lignocellulolytic enzymes is a step towards metabolically engineered bacteria that may be used for production of industrial products such as polylactic acid or ethanol directly from plant biomass. The concept of engineering *L. plantarum* to produce ethanol from plant biomass is very tempting as this bacterium possesses high tolerance to ethanol (up to 13% (v/v)), under conditions of low pH (in the range 3.2-4) (6). These traits, along with the ability to utilize hexose and pentose sugars, may render this bacterium a competitive alternative to other types of microbial systems (e.g., *Clostridium thermocellum*, *Saccharomyces cerevisiae* or *Escherichia coli*), engineered for this purpose (53-55).

The development of a novel bioprocessing system in *L. plantarum* for converting biomass to biofuels could thus be of major importance to the field of green energy, which will have tremendous impact on global economic and environmental concerns.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

1. Bayer E A, Lamed R, White B A, Flint H J. 2008. From cellulosomes to cellulosomics. Chem Rec 8:364-377.
2. Teusink B, Wiersma A, Molenaar D, Francke C, de Vos W M, Siezen R J, Smid E J. 2006. Analysis of growth of *Lactobacillus plantarum* WCFS1 on a complex medium using a genome-scale metabolic model. The Journal of biological chemistry 281:40041-40048.
3. Klocke M, Mundt K, Idler C, McEniry J, O'Kiely P, Barth S. 2006. Monitoring *Lactobacillus plantarum* in grass silages with the aid of 16S rDNA-based quantitative real-time PCR assays. Systematic and applied microbiology 29:49-58.

4. Roach D R, Khatibi P A, Bischoff K M, Hughes S R, Donovan D M. 2013. Bacteriophage-encoded lytic enzymes control growth of contaminating *Lactobacillus* found in fuel ethanol fermentations. Biotechnology for biofuels 6:20.
5. Limayem A, Hanning I B, Muthaiyan A, Illeghems K, Kim J W, Crandall P G, O'Bryan C A, Ricke S C. 2011. Alternative antimicrobial compounds to control potential *Lactobacillus* contamination in bioethanol fermentations. Journal of environmental science and health. Part. B, Pesticides, food contaminants, and agricultural wastes 46:709-714.
6. Alegria E G, Lopez I, Ruiz J I, Saenz J, Fernandez E, Zarazaga M, Dizy M, Torres C, Ruiz-Larrea F. 2004. High tolerance of wild *Lactobacillus plantarum* and *Oenococcus oeni* strains to lyophilisation and stress environmental conditions of acid pH and ethanol. FEMS Microbiol Lett 230:53-61.
7. Nichols N N, Dien B S, Bothast R J. 2003. Engineering lactic acid bacteria with pyruvate decarboxylase and alcohol dehydrogenase genes for ethanol production from *Zymomonas mobilis*. Journal of industrial microbiology & biotechnology 30:315-321.
8. Domagk G F, Horecker B L. 1958. Pentose fermentation by *Lactobacillus plantarum*. V. Fermentation of 2-deoxy-D-ribose. The Journal of biological chemistry 233:283-286.
9. Kleerebezem M, Boekhorst J, van Kranenburg R, Molenaar D, Kuipers O P, Leer R, Tarchini R, Peters S A, Sandbrink H M, Fiers M W, Stiekema W, Lankhorst R M, Bron P A, Hoffer S M, Groot M N, Kerkhoven R, de Vries M, Ursing B, de Vos W M, Siezen R J. 2003. Complete genome sequence of *Lactobacillus plantarum* WCFS1. Proceedings of the National Academy of Sciences of the United States of America 100:1990-1995.
10. Ganzle M G, Vermeulen N, Vogel R F. 2007. Carbohydrate, peptide and lipid metabolism of lactic acid bacteria in sourdough. Food microbiology 24:128-138.
11. Okano K, Yoshida S, Yamada R, Tanaka T, Ogino C, Fukuda H, Kondo A. 2009 Improved production of homo-D-lactic acid via xylose fermentation by introduction of xylose assimilation genes and redirection of the phosphoketolase pathway to the pentose phosphate pathway in L-Lactate dehydrogenase gene-deficient *Lactobacillus plantarum*. Appl Environ Microbiol 75:7858-7861.
12. Cantarel B L, Coutinho P M, Rancurel C, Bernard T, Lombard V, Henrissat B. 2009. The Carbohydrate-Active EnZymes database (CAZy): an expert resource for Glycogenomics. Nucleic Acids Res 37:D233-238.
13. Sorvig E, Mathiesen G, Naterstad K, Eijsink V G H, Axelsson L. 2005. High-level, inducible gene expression in *Lactobacillus sakei* and *Lactobacillus plantarum* using versatile expression vectors. Microbiology 151:2439-2449.
14. Sorvig E, Gronqvist S, Naterstad K, Mathiesen G, Eijsink V G H, Axelsson L. 2003. Construction of vectors for inducible gene expression in *Lactobacillus sakei* and *L. plantarum*. FEMS Microbiol Lett 229:119-126.
15. Mathiesen G, Sveen A, Brurberg M B, Fredriksen L, Axelsson L, Eijsink V G H. 2009. Genome-wide analysis of signal peptide functionality in *Lactobacillus plantarum* WCFS1. BMC genomics 10:425.
16. Mierau I, Kleerebezem M. 2005. 10 years of the nisin-controlled gene expression system (NICE) in *Lactococcus lactis*. Applied microbiology and biotechnology 68:705-717.
17. Kleerebezem M, Beerthuyzen M M, Vaughan E E, de Vos W M, Kuipers O P. 1997. Controlled gene expression systems for lactic acid bacteria: transferable nisin-inducible expression cassettes for *Lactococcus, Leuconostoc*, and *Lactobacillus* spp. Appl Environ Microbiol 63:4581-4584.
18. Pavan S, Hols P, Delcour J, Geoffroy M C, Grangette C, Kleerebezem M, Mercenier A. 2000. Adaptation of the nisin-controlled expression system in *Lactobacillus plantarum*: a tool to study in vivo biological effects. Appl Environ Microbiol 66:4427-4432.
19. Bohmer N, Lutz-Wahl S, Fischer L. 2012. Recombinant production of hyperthermostable CelB from *Pyrococcus furiosus* in *Lactobacillus* sp. Applied microbiology and biotechnology 96:903-912.
20. Mathiesen G, Sveen A, Piard J C, Axelsson L, Eijsink V G H. 2008. Heterologous protein secretion by *Lactobacillus plantarum* using homologous signal peptides. Journal of applied microbiology 105:215-226.
21. Moraïs S, Barak Y, Caspi J, Hadar Y, Lamed R, Shoham Y, Wilson D B, Bayer E A. 2010. Contribution of a xylan-binding module to the degradation of a complex cellulosic substrate by designer cellulosomes. Applied and Environmental Microbiology 76:3787-3796.
22. Ghangas G S, Wilson D B. 1988. Cloning of the *Thermomonospora fusca* Endoglucanase *E2* Gene in *Streptomyces lividans*: Affinity Purification and Functional Domains of the Cloned Gene Product. Appl Environ Microbiol 54:2521-2526.
23. Aukrust T, Blom H. 1992. Transformation of *Lactobacillus* strains used in meat and vegetable fermentations. Food Res. Int. 25:253-261.
24. Caspi J, Irwin D, Lamed R, Shoham Y, Fierobe H-P, Wilson D B, Bayer E A. 2006. *Thermobifida fusca* family-6 cellulases as potential designer cellulosome components. Biocatalysis and Biotransformation 24:3-12.
25. Lamed R, Kenig R, Setter E, Bayer E A. 1985. Major characteristics of the cellulolytic system of *Clostridium thermocellum* coincide with those of the purified cellulosome. Enzyme Microb. Technol. 7:37-41.
26. Eijsink V G H, Brurberg M B, Middelhoven P H, Nes I F. 1996. Induction of bacteriocin production in *Lactobacillus sakei* by a secreted peptide. Journal of bacteriology 178:2232-2237.
27. Anbar M, Lamed R, Bayer E A. 2010. Thermostability enhancement of *Clostridium thermocellum* cellulosomal endoglucanase Cel8A by a single glycine substitution. Chem Cat Chem 2:997-1003.
28. Fierobe H-P, Mingardon F, Mechaly A, Belaich A, Rincon M T, Lamed R, Tardif C, Belaich J-P, Bayer E A. 2005. Action of designer cellulosomes on homogeneous versus complex substrates: Controlled incorporation of three distinct enzymes into a defined tri-functional scaffoldin. Journal of Biological Chemistry 280:16325-16334.
29. Tabka M G, Herpoel-Gimbert I, Monod F, Asther M, Sigoillot J C. 2006. Enzymatic saccharification of wheat straw for bioethanol production by a combined cellulase xylanase and feruloyl esterase treatment. Enzyme and Microbial Technology 39:897-902.
30. Morais S, Morag E, Barak Y, Goldman D, Hadar Y, Lamed R, Shoham Y, Wilson D B, Bayer E A. 2012. Deconstruction of lignocellulose into soluble sugars by native and designer cellulosomes. mBio 3.
31. Miller G L. 1959. Use of dinitrosalicylic acid reagent for determination of reducing sugar. Analytical Biochemistry 31:426-428.

32. Ghose T K. 1987. Measurements of cellulase activity. Pure. Appl. Chem 59:257-268.
33. Moraïs S, Barak Y, Caspi J, Hadar Y, Lamed R, Shoham Y, Wilson D B, Bayer E A. 2010. Cellulase-xylanase synergy in designer cellulosomes for enhanced degradation of a complex cellulosic substrate. mBio 1:e00285-00210.
34. Morais S, Morag E, Barak Y, Goldman D, Hadar Y, Lamed R, Shoham Y, Wilson D B, Bayer E A. 2013. Deconstruction of lignocellulose into soluble sugars by native and designer cellulosomes. mBio 3:e00508-00512.
35. Caspi J, Barak Y, Haimovitz R, Irwin D, Lamed R, Wilson D B, Bayer E A. 2009. Effect of linker length and dockerin position on conversion of a *Thermobifida fusca* endoglucanase to the cellulosomal mode. Applied and Environmental Microbiology 75:7335-7342.
36. Caspi J, Irwin D, Lamed R, Fierobe H-P, Wilson D B, Bayer E A. 2008. Conversion of noncellulosomal *Thermobifida fusca* free exoglucanases into cellulosomal components: Comparative impact on cellulose-degrading activity. Journal of Biotechnology 135:351-357.
37. Wilson D B. 2004. Studies of *Thermobifida fusca* plant cell wall degrading enzymes. Chem Rec 4:72-82.
38. Chen S, Wilson D B. 2007. Proteomic and transcriptomic analysis of extracellular proteins and mRNA levels in *Thermobifida fusca* grown on cellobiose and glucose. Journal of bacteriology 189:6260-6265.
39. Kim J H, Irwin D, Wilson D B. 2004. Purification and characterization of Thermobifida *fusca* xylanase 10B. Canadian Journal of Microbiology 50:835-843.
40. Nguyen T T, Nguyen T H, Maischberger T, Schmelzer P, Mathiesen G, Eijsink V G, Haltrich D, Peterbauer C K. 2011. Quantitative transcript analysis of the inducible expression system pSIP: comparison of the overexpression of *Lactobacillus* spp. beta-galactosidases in *Lactobacillus plantarum*. Microbial cell factories 10:46.
41. Irwin D, Jung E D, Wilson D B. 1994. Characterization and sequence of a *Thermomonospora fusca* xylanase. Applied and Environmental Microbiology 60:763-770.
42. McDonald L C, Fleming H P, Hassan H M. 1990. Acid Tolerance of *Leuconostoc mesenteroides* and *Lactobacillus plantarum*. Appl Environ Microbiol 56:2120-2124.
43. Mathiesen G, Huehne K, Kroeckel L, Axelsson L, Eijsink V G H. 2005. Characterization of a new bacteriocin operon in sakacin P-producing *Lactobacillus sakei*, showing strong translational coupling between the bacteriocin and immunity genes. Appl Environ Microbiol 71:3565-3574.
44. Baek S H, Kim S, Lee K, Lee J K, Hahn J S. 2012. Cellulosic ethanol production by combination of cellulase-displaying yeast cells. Enzyme Microb Technol 51:366-372.
45. Hu J, Arantes V, Saddler J N. 2011. The enhancement of enzymatic hydrolysis of lignocellulosic substrates by the addition of accessory enzymes such as xylanase: is it an additive or synergistic effect? Biotechnology for biofuels 4:36.
46. Qing Q, Wyman C E. 2011. Supplementation with xylanase and beta-xylosidase to reduce xylo-oligomer and xylan inhibition of enzymatic hydrolysis of cellulose and pretreated corn stover. Biotechnology for biofuels 4:18.
47. Zhang J, Tuomainen P, Siika-Aho M, Viikari L. 2011. Comparison of the synergistic action of two thermostable xylanases from GH families 10 and 11 with thermostable cellulases in lignocellulose hydrolysis. Bioresour Technol 102:9090-9095.
48. Rossi F, Rudella A, Marzotto M, Dellaglio F. 2001. Vector-free cloning of a bacterial endo-1,4-beta-glucanase in *Lactobacillus plantarum* and its effect on the acidifying activity in silage: use of recombinant cellulolytic *Lactobacillus plantarum* as silage inoculant. Antonie van Leeuwenhoek 80:139-147.
49. Ozkose E, Akyol I, Kar B, Comlekcioglu U, Ekinci M S. 2009. Expression of fungal cellulase gene in *Lactococcus lactis* to construct novel recombinant silage inoculants. Folia microbiologica 54:335-342.
50. Cho J S, Choi Y J, Chung D K. 2000. Expression of *Clostridium thermocellum* endoglucanase gene in *Lactobacillus gasseri* and *Lactobacillus johnsonii* and characterization of the genetically modified probiotic lactobacilli. Current microbiology 40:257-263.
51. Liu J R, Yu B, Liu F H, Cheng K J, Zhao X. 2005. Expression of rumen microbial fibrolytic enzyme genes in probiotic *Lactobacillus reuteri*. Appl Environ Microbiol 71:6769-6775.
52. Liu J R, Yu B, Zhao X, Cheng K J. 2007. Coexpression of rumen microbial beta-glucanase and xylanase genes in *Lactobacillus reuteri*. Applied microbiology and biotechnology 77:117-124.
53. Wood B E, Beall D S, Ingram L O. 1997. Production of recombinant bacterial endoglucanase as a co-product with ethanol during fermentation using derivatives of *Escherichia coli* KO11. Biotechnology and bioengineering 55:547-555.
54. Balusu R, Paduru R M, Seenayya G, Reddy G. 2004. Production of ethanol from cellulosic biomass by *Clostridium thermocellum* SS19 in submerged fermentation: screening of nutrients using Plackett-Burman design. Applied biochemistry and biotechnology 117:133-141.
55. Tsai S L, Oh J, Singh S, Chen R, Chen W. 2009. Functional assembly of minicellulosomes on the *Saccharomyces cerevisiae* cell surface for cellulose hydrolysis and ethanol production. Appl Environ Microbiol 75:6087-6093.

What is claimed is:

1. A bacterial culture comprising a biomass composition and a population of lactic acid bacteria which comprises:
    (i) a first population of lactic acid bacteria which has been genetically modified to express a secreted cellulase;
    (ii) a second population of lactic acid bacteria which has been genetically modified to express a secreted xylanase, wherein the ratio of the first population: second population is selected such that the specific activity of cellulase: xylanase in the culture is greater than 4:1 or less than 1:4; and
    (iii) a third population of lactic acid bacteria which has been genetically modified to produce ethanol.

2. The culture of claim 1, wherein said lactic acid bacteria comprise *Lactobacillus plantarum*.

3. The culture of claim 1, wherein the ratio of the first population: second population is selected such that the specific activity of cellulase: xylanase in the culture is greater than 10:1 or less than 1:10.

4. The culture claim 1, wherein said first population and said second population comprise identical strains of bacteria.

5. The culture of claim 1, wherein said first population and said second population comprise non-identical strains of bacteria.

6. The culture of claim 1, wherein said third population of lactic acid bacteria are genetically modified to express alcohol dehydrogenase and pyruvate decarboxylase.

7. The culture of claim 1, wherein said third population of lactic acid bacteria do not express at least one L-lactate dehydrogenase.

8. A method of producing ethanol comprising propagating the culture of claim 1 under conditions that allow generation of the ethanol, thereby producing the ethanol.

9. The method of claim 8, further comprising isolating the ethanol following the generating.

10. A bacterial culture comprising a biomass composition and a population of lactic acid bacteria which comprises:
    (i) a first population of lactic acid bacteria which has been genetically modified to express a secreted cellulase;
    (ii) a second population of lactic acid bacteria which has been genetically modified to express a secreted xylanase, wherein the ratio of the first population: second population is selected such that the specific activity of cellulase: xylanase in the culture is greater than 4:1 or less than 1:4, wherein said first and/or said second population of lactic acid bacteria has been further genetically modified to produce ethanol.

11. The culture of claim 10, wherein said first population of lactic acid bacteria and/or said second population of lactic acid bacteria are genetically modified to express alcohol dehydrogenase and pyruvate decarboxylase.

12. The culture of claim 10, wherein said first and/or said second population of lactic acid bacteria do not express at least one L-lactate dehydrogenase.

13. An article of manufacture comprising:
    (i) a first population of lactic acid bacteria which are genetically modified to express at least one fibrolytic enzyme; and
    (ii) a second population of lactic acid bacteria which are genetically modified to produce ethanol from C5 or C6 sugars.

14. The article of manufacture of claim 13, wherein said first population of lactic acid bacteria express a cellulase.

15. The article of manufacture of claim 14, further comprising a third population of lactic acid bacteria, which are genetically modified to express a xylanase.

16. The article of manufacture of claim 13, wherein said at least one fibrolytic enzyme is expressed as a fusion protein with dockerin.

17. The article of manufacture of claim 13, wherein said at least one fibrolytic enzyme comprises a cellulose and/or a xylanase.

18. The article of manufacture of claim 13, wherein said second population of lactic acid bacteria are genetically modified to express alcohol dehydrogenase and pyruvate decarboxylase.

19. The article of manufacture of claim 13, wherein said first population of lactic acid bacteria and said second population of lactic acid bacteria are packaged in separate packaging.

20. An isolated cell population of lactic acid bacteria which are genetically modified to express at least one fibrolytic enzyme and to produce ethanol from C5 or C6 sugars.

21. The isolated cell population of claim 20, being genetically modified to express alcohol dehydrogenase and pyruvate decarboxylase.

* * * * *

SEQUENCE LISTING

```
<160> NUMBER OF SEQ ID NOS: 40

<210> SEQ ID NO 1
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 1
tcttctcgag atggcatccc ccagacctct                                        30
```

<210> SEQ ID NO 2
<211> LENGTH: 30
<212> TYPE: DNA
<213> ORGANISM: Artificial Sequence
<220> FEATURE:
<223> OTHER INFORMATION: Single strand DNA oligonucleotide

<400> SEQUENCE: 2
aataagcttt cagctggcgg cgcaggtaag                             30

<210> SEQ ID NO 3
<211> LENGTH: 31
<212> TYPE: DNA
<213> ORGANISM: Artificial Sequence
<220> FEATURE:
<223> OTHER INFORMATION: Single strand DNA oligonucleotide

<400> SEQUENCE: 3
tcttgtcgac atggccgtga cctccaacga g                           31

<210> SEQ ID NO 4
<211> LENGTH: 29
<212> TYPE: DNA
<213> ORGANISM: Artificial Sequence
<220> FEATURE:
<223> OTHER INFORMATION: Single strand DNA oligonucleotide

<400> SEQUENCE: 4
aataagcttc tagttggcgc tgcaggaca                              29

<210> SEQ ID NO 5
<211> LENGTH: 36
<212> TYPE: DNA
<213> ORGANISM: Artificial Sequence
<220> FEATURE:
<223> OTHER INFORMATION: Single strand DNA oligonucleotide

<400> SEQUENCE: 5
atatatccat ggatggcatc ccccagacct cttcgc                      36

<210> SEQ ID NO 6
<211> LENGTH: 35
<212> TYPE: DNA
<213> ORGANISM: Artificial Sequence
<220> FEATURE:
<223> OTHER INFORMATION: Single strand DNA oligonucleotide

<400> SEQUENCE: 6
atatattcta gatcactcca ggctggcggc gcagg                       35

<210> SEQ ID NO 7
<211> LENGTH: 38
<212> TYPE: DNA
<213> ORGANISM: Artificial Sequence
<220> FEATURE:
<223> OTHER INFORMATION: Single strand DNA oligonucleotide

<400> SEQUENCE: 7
tcagtctcat gaatggccgt gacctccaac gagaccgg                    38

<210> SEQ ID NO 8
<211> LENGTH: 34
<212> TYPE: DNA
<213> ORGANISM: Artificial Sequence
<220> FEATURE:

<223> OTHER INFORMATION: Single strand DNA oligonucleotide

<400> SEQUENCE: 8
agcgtatcta gactagttgg cgctgcagga cacc                              34

<210> SEQ ID NO 9
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 9
atttagctgg ctggcgtaaa gtatg                                        25

<210> SEQ ID NO 10
<211> LENGTH: 25
<212> TYPE: DNA
<213> ORGANISM: Artificial Sequence
<220> FEATURE:
<223> OTHER INFORMATION: Single strand DNA oligonucleotide

<400> SEQUENCE: 10
tcatttcagg attgatcatt gttgc                                        25

<210> SEQ ID NO 11
<211> LENGTH: 23
<212> TYPE: DNA
<213> ORGANISM: Artificial Sequence
<220> FEATURE:
<223> OTHER INFORMATION: Single strand DNA oligonucleotide

<400> SEQUENCE: 11
gacgaccccg aagacacaac tag                                          23

<210> SEQ ID NO 12
<211> LENGTH: 1332
<212> TYPE: DNA
<213> ORGANISM: Thermobifida fusca

<400> SEQUENCE: 12
atggcatccc ccagacctct tcgcgctctt ctgggcgccg cggcggcggc cttggtcagc    60
gcggctgctc tggccttccc gtcgcaagcg gcggccaatg attctccgtt ctacgtcaac   120
cccaacatgt cctccgccga atgggtgcgg aacaacccca cgacccgcg taccccggta    180 atccgcgacc ggatcgccag cgtgccgcag ggcacctggt cgcccacca caaccccggg   240 cagatcaccg gccaggtcga cgcgctcatg agcgccgccc aggccgccgg caagatcccg   300
atcctggtcg tgtacaacgc cccggccgc gactgcggca ccacagcag cggcggcgcc    360 cccagtcaca gcgcctaccg gtcctggatc gacgaattcg ctgccggact gaagaaccgt   420
cccgcctaca tcatcgtcga accggacctg atctcgctga tgtcgagctg catgcagcac   480
gtccagcagg aagtcctgga gacgatggcg tacgcgggca aggccctcaa ggccgggtcc   540
tcgcaggcgc ggatctactt cgacgccggc cactccgcgt ggcactcgcc cgcacagatg   600
gcttcctggc tccagcaggc cgacatctcc aacagcgcgc acgtatcgc caccaacacc   660 tccaactacc ggtggaccgc tgacgaggtc gcctacgcca aggcggtgct ctcggccatc   720
ggcaacccgt ccctgcgcgc ggtcatcgac accagccgca acggcaacgg ccccgccggt   780
aacgagtggt gcgaccccag cggacgcgcc atcggcacgc ccagcaccac caacaccggc   840
gacccgatga tcgacgcctt cctgtggatc aagctgccgg gtgaggccga cggctgcatc   900

```
gccggcgccg gccagttcgt cccgcaggcg gcctacgaga tggcgatcgc cgcgggcggc    960
accaacccca acccgaaccc caacccgacg cccaccccca ctccgacccc cacgccgcct   1020
cccggctcct cggggcgtg cacggcgacg tacacgatcg ccaacgagtg gaacgacggc   1080
ttccaggcga ccgtgacggt caccgcgaac cagaacatca ccggctggac cgtgacgtgg   1140
accttcaccg acggccagac catcaccaac gcctggaacg ccgacgtgtc caccagcggc   1200
tcctcggtga ccgcgcggaa cgtcggccac aacggaacgc tctcccaggg agcctccaca   1260
gagttcggct tcgtcggctc taagggcaac tccaactctg ttccgaccct tacctgcgcc   1320
gccagcctcg ag                                                      1332
```

<210> SEQ ID NO 13
<211> LENGTH: 444
<212> TYPE: PRT
<213> ORGANISM: Thermobifida fusca

<400> SEQUENCE: 13

```
Met Ala Ser Pro Arg Pro Leu Arg Ala Leu Leu Gly Ala Ala Ala Ala
1               5                   10                  15

Ala Leu Val Ser Ala Ala Ala Leu Ala Phe Pro Ser Gln Ala Ala Ala
            20                  25                  30

Asn Asp Ser Pro Phe Tyr Val Asn Pro Asn Met Ser Ser Ala Glu Trp
        35                  40                  45

Val Arg Asn Asn Pro Asn Asp Pro Arg Thr Pro Val Ile Arg Asp Arg
    50                  55                  60

Ile Ala Ser Val Pro Gln Gly Thr Trp Phe Ala His His Asn Pro Gly
65                  70                  75                  80

Gln Ile Thr Gly Gln Val Asp Ala Leu Met Ser Ala Ala Gln Ala Ala
                85                  90                  95

Gly Lys Ile Pro Ile Leu Val Val Tyr Asn Ala Pro Gly Arg Asp Cys
            100                 105                 110

Gly Asn His Ser Ser Gly Gly Ala Pro Ser His Ser Ala Tyr Arg Ser
        115                 120                 125

Trp Ile Asp Glu Phe Ala Ala Gly Leu Lys Asn Arg Pro Ala Tyr Ile
    130                 135                 140

Ile Val Glu Pro Asp Leu Ile Ser Leu Met Ser Ser Cys Met Gln His
145                 150                 155                 160

Val Gln Gln Glu Val Leu Glu Thr Met Ala Tyr Ala Gly Lys Ala Leu
                165                 170                 175

Lys Ala Gly Ser Ser Gln Ala Arg Ile Tyr Phe Asp Ala Gly His Ser
            180                 185                 190

Ala Trp His Ser Pro Ala Gln Met Ala Ser Trp Leu Gln Gln Ala Asp
        195                 200                 205

Ile Ser Asn Ser Ala His Gly Ile Ala Thr Asn Thr Ser Asn Tyr Arg
    210                 215                 220

Trp Thr Ala Asp Glu Val Ala Tyr Ala Lys Ala Val Leu Ser Ala Ile
225                 230                 235                 240

Gly Asn Pro Ser Leu Arg Ala Val Ile Asp Thr Ser Arg Asn Gly Asn
                245                 250                 255

Gly Pro Ala Gly Asn Glu Trp Cys Asp Pro Ser Gly Arg Ala Ile Gly
            260                 265                 270

Thr Pro Ser Thr Thr Asn Thr Gly Asp Pro Met Ile Asp Ala Phe Leu
        275                 280                 285
```

```
Trp Ile Lys Leu Pro Gly Glu Ala Asp Gly Cys Ile Ala Gly Ala Gly
        290                 295                 300

Gln Phe Val Pro Gln Ala Ala Tyr Glu Met Ala Ile Ala Ala Gly Gly
305                 310                 315                 320

Thr Asn Pro Asn Pro Asn Pro Asn Pro Thr Pro Thr Pro Thr Pro Thr
                325                 330                 335

Pro Thr Pro Pro Pro Gly Ser Ser Gly Ala Cys Thr Ala Thr Tyr Thr
                340                 345                 350

Ile Ala Asn Glu Trp Asn Asp Gly Phe Gln Ala Thr Val Thr Val Thr
                355                 360                 365

Ala Asn Gln Asn Ile Thr Gly Trp Thr Val Trp Thr Phe Thr Asp
370                 375                 380

Gly Gln Thr Ile Thr Asn Ala Trp Asn Ala Asp Val Ser Thr Ser Gly
385                 390                 395                 400

Ser Ser Val Thr Ala Arg Asn Val Gly His Asn Gly Thr Leu Ser Gln
                405                 410                 415

Gly Ala Ser Thr Glu Phe Gly Phe Val Gly Ser Lys Gly Asn Ser Asn
                420                 425                 430

Ser Val Pro Thr Leu Thr Cys Ala Ala Ser Leu Glu
                435                 440
```

<210> SEQ ID NO 14
<211> LENGTH: 891
<212> TYPE: DNA
<213> ORGANISM: Thermobifida fusca

<400> SEQUENCE: 14

```
gccgtgacct ccaacgagac cgggtaccac gacgggtact tctactcgtt ctggaccgac        60
gcgcctggaa cggtctccat ggagctgggc cctggcggaa actacagcac ctcctggcgg       120
aacaccggga acttcgtcgc cggtaaggga tgggccaccg gtggccgccg gaccgtgacc       180
tactccgcca gcttcaaccc gtcgggtaac gcctacctga ccctctacgg gtggacgcgg       240
aacccgctcg tggagtacta catcgtcgaa agctggggca cctaccggcc caccggtacc       300
tacatgggca cggtgaccac cgacggtggt acctacgaca tctacaagac cacgcggtac       360
aacgcgccct ccatcgaagg cacccggacc ttcgaccagt actggagcgt ccgccagtcc       420
aagcggacca cgggtaccat caccgcgggg aaccacttcg acgcgtgggc cgccacggt       480
atgcacctcg aacccacga ctacatgatc atggcgaccg agggctacca gagcagcgga       540
tcctccaacg tgacgttggg caccagcggc ggtggaaacc ccggtggggg caacccccc       600
ggtggcggca accccccggg tgcggtggc tgcacggcga cgctgtccgc gggccagcag       660
tggaacgacc gctacaacct caacgtcaac gtcagcggct ccaacaactg gaccgtgacc       720
gtgaacgttc cgtggccggc gaggatcatc gccacctgga acatccacgc cagctacccg       780
gactcccaga ccttggttgc ccggcctaac ggcaacggca caactggggg catgacgatc       840
atgcacaacg gcaactggac gtggcccacg gtgtcctgca gcgccaacta g                891
```

<210> SEQ ID NO 15
<211> LENGTH: 296
<212> TYPE: PRT
<213> ORGANISM: Thermobifida fusca

<400> SEQUENCE: 15

```
Ala Val Thr Ser Asn Glu Thr Gly Tyr His Asp Gly Tyr Phe Tyr Ser
1               5                   10                  15
```

```
Phe Trp Thr Asp Ala Pro Gly Thr Val Ser Met Glu Leu Gly Pro Gly
             20                  25                  30

Gly Asn Tyr Ser Thr Ser Trp Arg Asn Thr Gly Asn Phe Val Ala Gly
         35                  40                  45

Lys Gly Trp Ala Thr Gly Gly Arg Arg Thr Val Thr Tyr Ser Ala Ser
 50                  55                  60

Phe Asn Pro Ser Gly Asn Ala Tyr Leu Thr Leu Tyr Gly Trp Thr Arg
 65                  70                  75                  80

Asn Pro Leu Val Glu Tyr Ile Val Glu Ser Trp Gly Thr Tyr Arg
                 85                  90                  95

Pro Thr Gly Thr Tyr Met Gly Thr Val Thr Thr Asp Gly Gly Thr Tyr
             100                 105                 110

Asp Ile Tyr Lys Thr Thr Arg Tyr Asn Ala Pro Ser Ile Glu Gly Thr
             115                 120                 125

Arg Thr Phe Asp Gln Tyr Trp Ser Val Arg Gln Ser Lys Arg Thr Ser
130                 135                 140

Gly Thr Ile Thr Ala Gly Asn His Phe Asp Ala Trp Ala Arg His Gly
145                 150                 155                 160

Met His Leu Gly Thr His Asp Tyr Met Ile Met Ala Thr Glu Gly Tyr
                 165                 170                 175

Gln Ser Ser Gly Ser Ser Asn Val Thr Leu Gly Thr Ser Gly Gly Gly
             180                 185                 190

Asn Pro Gly Gly Gly Asn Pro Gly Gly Gly Asn Pro Gly Gly
             195                 200                 205

Gly Gly Cys Thr Ala Thr Leu Ser Ala Gly Gln Gln Trp Asn Asp Arg
210                 215                 220

Tyr Asn Leu Asn Val Asn Val Ser Gly Ser Asn Asn Trp Thr Val Thr
225                 230                 235                 240

Val Asn Val Pro Trp Pro Ala Arg Ile Ile Ala Thr Trp Asn Ile His
                 245                 250                 255

Ala Ser Tyr Pro Asp Ser Gln Thr Leu Val Ala Arg Pro Asn Gly Asn
                 260                 265                 270

Gly Asn Asn Trp Gly Met Thr Ile Met His Asn Gly Asn Trp Thr Trp
             275                 280                 285

Pro Thr Val Ser Cys Ser Ala Asn
    290                 295

<210> SEQ ID NO 16
<211> LENGTH: 106
<212> TYPE: DNA
<213> ORGANISM: Lactobacillus plantarum

<400> SEQUENCE: 16
tatgaaaaaa attaataagt tgatgatctt aggcatgctc gttttgggg taacggggc      60 aacaatgatc aatcctgaaa tgacgaccgc agcgcatgct agcgcc                  106

<210> SEQ ID NO 17
<211> LENGTH: 124
<212> TYPE: DNA
<213> ORGANISM: Lactobacillus plantarum

<400> SEQUENCE: 17
tatgaaaaaa tttaacttta aaccatgtt gctattagtt ttggctagtt gtgtcttcgg     60
ggtcgtcgtt aacgtgacta ctagtcttgg accacaaacc gcaatcaccg cccaggcctc   120
caag                                                                124
```

<210> SEQ ID NO 18
<211> LENGTH: 2094
<212> TYPE: DNA
<213> ORGANISM: Clostridium clariflavum

<400> SEQUENCE: 18

| | | | | | |
|---|---|---|---|---|---|
| atgaaacata | aacttatggg | aaaattttcg | attttaatga | gtcttacact | tttgttatca | 60 |
| ctgttgccgt | taaatgtgca | ggcaaaaacc | gttacctcta | atgagaccgg | tactcatggg | 120 |
| ggctataact | atgaatactg | gaaagacagc | ggcaacggaa | caatggttct | caaggatggc | 180 |
| ggagctttca | gctgcgaatg | gaataatatt | aacaatattt | tattccgcaa | gggtcttaaa | 240 |
| tttgatgaga | caaagaccca | ccagcaaatt | ggctatatga | cactgactta | ttcgtgtgat | 300 |
| tatcaaccta | acggtaattc | atatctggct | gtctatggat | ggacaagtga | ccctcttgta | 360 |
| gaatattacg | ttatcgagag | ctggggaacc | tggaagccgc | caggaaatgt | gcaatcaaaa | 420 |
| ggtactatta | ccgttgacgg | tggagtatac | gacatatttg | aaacaaccag | atacaatcag | 480 |
| ccttccataa | aaggtaatgc | aacattccag | caatattgga | gtgttcgcca | gcagaaacgt | 540 |
| acaagcggaa | cagtatctgt | tactgaacac | tttaaagctt | gggaagctaa | aggaatgaag | 600 |
| atgggaaaat | tctatgaaat | ttcccttgtt | gtagaaggat | atcaaagcag | cggtaaagcc | 660 |
| gatgtaacca | tgatgtcaat | taatattggc | ggaaattcag | caaatcctac | cggtaccact | 720 |
| gttgtgccaa | ctcctgcatc | gggttccggg | aaaagtgctt | tttcaactat | agaagccgaa | 780 |
| gactttgaca | atgcttacgg | ttcaagcata | agatccattg | gtatgggtgt | aggttacata | 840 |
| gaaaacggta | actacctggt | atataacaat | atcaattttg | gtgacggagc | aagtgctttt | 900 |
| agtgccaaag | ttgctaacgg | taatactact | gcaacaacta | ttcaattaag | attaggcagc | 960 |
| ccgagcggta | ctctgatagg | ttcttttaagt | gtgccctcaa | ccggtggctg | aacaattat | 1020 |
| gaagaattat | ccactaccgt | aagcggagca | tccggaacaa | aagacctgta | cctctgcttt | 1080 |
| aacggacctg | taaatattga | ttgtttctcc | tttgcgaaag | gaaattccaa | tacaaatcct | 1140 |
| ataaatccgg | gctacatatt | gcttggtgac | gttgaccaga | acggtactat | aaattctttg | 1200 |
| gattatgcca | atacaaaat | gtatttgctt | ggaatgataa | gttctcttcc | tgaggaaggg | 1260 |
| gatataaaca | gagacggcga | catgaactca | attgactatg | caatgctgaa | acagcatctt | 1320 |
| ttgggtataa | ttaatttgga | agagctttca | ggacctaaaa | caacacctac | accggttgtg | 1380 |
| attgttacac | cgactcctac | aaaaacgcca | tctgaaggta | cattccactg | cttcttgctg | 1440 |
| cttggtcagt | cgaatatggc | aggatgggcc | agggctcaag | attctgacaa | gatacctaat | 1500 |
| ccgcgcatac | ttgcactggg | ctatgacaat | aatcagtggg | gtgtagctgt | accgccgttg | 1560 |
| catgaagcat | ttcaaggcgc | tataggtcct | ggtgactggt | tgctaaaac | aataattgaa | 1620 |
| agacttcctg | aaaatgatac | tataggattg | ataccgtgtg | ctataagcgg | tgaaaagatc | 1680 |
| gaaaccttca | tgaaaaatgg | aggatcaaaa | tataattgga | ttgtcagccg | tgcaagaatg | 1740 |
| gcacagcaaa | gaggaggagt | tatttgaaggt | atcctcttcc | accagggtga | gtccaacaac | 1800 |
| ggtcagcaag | attggcctaa | taagtaagt | acactgattt | cagacctcaa | aaaagactta | 1860 |
| gggcttggag | atattcctgt | tctggtggga | gaattgctct | ataccggtag | ctgtgcaggg | 1920 |
| cataatactt | tggtaaacag | actgccgtca | atgattccga | attgttatgt | tatttctgca | 1980 |
| caaggtttat | ccggtgaccc | ggcagatttc | tggggactcc | atttcaatca | tgattctact | 2040 |
| gttgaattcg | gtaagagata | tgcgaaaaaa | atgattgaag | tacttggatg | gtaa | 2094 |

<210> SEQ ID NO 19
<211> LENGTH: 697
<212> TYPE: PRT
<213> ORGANISM: Clostridium clariflavum

<400> SEQUENCE: 19

```
Met Lys His Lys Leu Met Gly Lys Phe Ser Ile Leu Met Ser Leu Thr
1               5                   10                  15

Leu Leu Leu Ser Leu Leu Pro Leu Asn Val Gln Ala Lys Thr Val Thr
            20                  25                  30

Ser Asn Glu Thr Gly Thr His Gly Gly Tyr Asn Tyr Glu Tyr Trp Lys
        35                  40                  45

Asp Ser Gly Asn Gly Thr Met Val Leu Lys Asp Gly Gly Ala Phe Ser
    50                  55                  60

Cys Glu Trp Asn Asn Ile Asn Asn Ile Leu Phe Arg Lys Gly Leu Lys
65                  70                  75                  80

Phe Asp Glu Thr Lys Thr His Gln Gln Ile Gly Tyr Met Thr Leu Thr
                85                  90                  95

Tyr Ser Cys Asp Tyr Gln Pro Asn Gly Asn Ser Tyr Leu Ala Val Tyr
            100                 105                 110

Gly Trp Thr Ser Asp Pro Leu Val Glu Tyr Tyr Val Ile Glu Ser Trp
        115                 120                 125

Gly Thr Trp Lys Pro Pro Gly Asn Val Gln Ser Lys Gly Thr Ile Thr
    130                 135                 140

Val Asp Gly Gly Val Tyr Asp Ile Phe Glu Thr Thr Arg Tyr Asn Gln
145                 150                 155                 160

Pro Ser Ile Lys Gly Asn Ala Thr Phe Gln Gln Tyr Trp Ser Val Arg
                165                 170                 175

Gln Gln Lys Arg Thr Ser Gly Thr Val Ser Val Thr Glu His Phe Lys
            180                 185                 190

Ala Trp Glu Ala Lys Gly Met Lys Met Gly Lys Phe Tyr Glu Ile Ser
        195                 200                 205

Leu Val Val Glu Gly Tyr Gln Ser Ser Gly Lys Ala Asp Val Thr Met
    210                 215                 220

Met Ser Ile Asn Ile Gly Gly Asn Ser Ala Asn Pro Thr Gly Thr Thr
225                 230                 235                 240

Val Val Pro Thr Pro Ala Ser Gly Ser Gly Lys Ser Ala Phe Ser Thr
                245                 250                 255

Ile Glu Ala Glu Asp Phe Asp Asn Ala Tyr Gly Ser Ser Ile Arg Ser
            260                 265                 270

Ile Gly Met Gly Val Gly Tyr Ile Glu Asn Gly Asn Tyr Leu Val Tyr
        275                 280                 285

Asn Asn Ile Asn Phe Gly Asp Gly Ala Ser Ala Phe Ser Ala Lys Val
    290                 295                 300

Ala Asn Gly Asn Thr Thr Ala Thr Thr Ile Gln Leu Arg Leu Gly Ser
305                 310                 315                 320

Pro Ser Gly Thr Leu Ile Gly Ser Leu Ser Val Pro Ser Thr Gly Gly
                325                 330                 335

Trp Asn Asn Tyr Glu Glu Leu Ser Thr Thr Val Ser Gly Ala Ser Gly
            340                 345                 350

Thr Lys Asp Leu Tyr Leu Cys Phe Asn Gly Pro Val Asn Ile Asp Cys
        355                 360                 365

Phe Ser Phe Ala Lys Gly Asn Ser Asn Thr Asn Pro Ile Asn Pro Gly
    370                 375                 380
```

Tyr Ile Leu Leu Gly Asp Val Asp Gln Asn Gly Thr Ile Asn Ser Leu
385                 390                 395                 400

Asp Tyr Ala Lys Tyr Lys Met Tyr Leu Leu Gly Met Ile Ser Ser Leu
            405                 410                 415

Pro Glu Glu Gly Asp Ile Asn Arg Asp Gly Asp Met Asn Ser Ile Asp
        420                 425                 430

Tyr Ala Met Leu Lys Gln His Leu Leu Gly Ile Ile Asn Leu Glu Glu
            435                 440                 445

Leu Ser Gly Pro Lys Thr Thr Pro Thr Pro Val Val Ile Val Thr Pro
450                 455                 460

Thr Pro Thr Lys Thr Pro Ser Glu Gly Thr Phe His Cys Phe Leu Leu
465                 470                 475                 480

Leu Gly Gln Ser Asn Met Ala Gly Trp Ala Arg Ala Gln Asp Ser Asp
            485                 490                 495

Lys Ile Pro Asn Pro Arg Ile Leu Ala Leu Gly Tyr Asp Asn Asn Gln
        500                 505                 510

Trp Gly Val Ala Val Pro Pro Leu His Glu Ala Phe Gln Gly Ala Ile
            515                 520                 525

Gly Pro Gly Asp Trp Phe Ala Lys Thr Ile Glu Arg Leu Pro Glu
530                 535                 540

Asn Asp Thr Ile Gly Leu Ile Pro Cys Ala Ile Ser Gly Glu Lys Ile
545                 550                 555                 560

Glu Thr Phe Met Lys Asn Gly Gly Ser Lys Tyr Asn Trp Ile Val Ser
            565                 570                 575

Arg Ala Arg Met Ala Gln Gln Arg Gly Gly Val Ile Glu Gly Ile Leu
            580                 585                 590

Phe His Gln Gly Glu Ser Asn Asn Gly Gln Gln Asp Trp Pro Asn Lys
        595                 600                 605

Val Ser Thr Leu Ile Ser Asp Leu Lys Lys Asp Leu Gly Leu Gly Asp
610                 615                 620

Ile Pro Val Leu Val Gly Glu Leu Leu Tyr Thr Gly Ser Cys Ala Gly
625                 630                 635                 640

His Asn Thr Leu Val Asn Arg Leu Pro Ser Met Ile Pro Asn Cys Tyr
            645                 650                 655

Val Ile Ser Ala Gln Gly Leu Ser Gly Asp Pro Ala Asp Phe Trp Gly
            660                 665                 670

Leu His Phe Asn His Asp Ser Thr Val Glu Phe Gly Lys Arg Tyr Ala
        675                 680                 685

Lys Lys Met Ile Glu Val Leu Gly Trp
    690                 695

<210> SEQ ID NO 20
<211> LENGTH: 1374
<212> TYPE: DNA
<213> ORGANISM: Clostridium thermocellum

<400> SEQUENCE: 20
atgaaacaaa aattactggt aactttcctg attttaatta cttttaccgt ttcgctgact      60
ttgtttccgg taaatgtacg cgctgatgtg gtaattacgt caaaccagac gggtactcac     120
ggcgggtaca actttgagta ctggaaagac accggaaacg gaaccatggt cctcaaagac     180
ggtggtgcgt tcagctgcga atggagcaat atcaacaata ttcttttccg taaaggtttc     240
aaatacgatg aaacaaagac acatgatcaa cttggataca taacggtaac ttattcctgc     300

-continued

```
aactatcagc caaacggaaa ctcttatctg ggagtctacg gatggaccag caatccgctt    360
gtagagtatt acatcatcga gagctgggga acctggagac caccgggagc aacaccaaag    420
ggcactatta ccgttgacgg tggtacatac gagatatacg agaccaccag agttaaccag    480
ccttccatca aggtacagc tactttccag caatactgga gtgtacgtac atcaaaacgt     540
acaagcggaa ccatatccgt aaccgaacac tttaaagcct gggaacgtct gggtatgaaa    600
atgggaaaaa tgtatgaggt tgctttggtt gtagaaggat accagagcag cggaaaagcc    660
gacgtaacca gcatgacaat tactgttggc aacgcaccgt caacatcatc accaccgggt    720
ccgacacctg aaccgactcc aagaagtgct ttttcaaaaa tcgaagctga ggagtacaac    780
tccctcaagt catcaaccat tcagaccata ggcacttccg acgaggaag cggtataggt     840
tatattgaaa gcggtgacta tctggtattt aacaaaataa actttggaaa cggtgcaaac    900
tctttcaagg caagggttgc atccggtgcg acacaccca ccaatatcca gttaagactc     960
ggaagcccga ccggtactct ataggaact cttacggtgg cttccacagg cggttggaac    1020
aattacgagg aaaaatcctg cagcataacc aacactacag acagcacga cttatatctg    1080
gtattctcag gtcctgttaa cattgactac ttcatattcg actcgaaagg tgtaaatcct   1140
acacctacac ctacttctcc gcctcaacaa gaccaggttt tgggtgactt gaacggagac   1200
aaacaagtaa attaacaga ctatacagca ctgaagagac atttgctcaa tataaccaga    1260
ctttcaggaa ccgctcttgc caatgccgat gtaaaccgcg acggcaaagt tgattccact   1320
gatcttatga tgttgcacag ataccttctt cgtataatct ccaaacttgg atga         1374
```

```
<210> SEQ ID NO 21
<211> LENGTH: 457
<212> TYPE: PRT
<213> ORGANISM: Clostridium thermocellum

<400> SEQUENCE: 21

Met Lys Gln Lys Leu Leu Val Thr Phe Leu Ile Leu Ile Thr Phe Thr
1               5                   10                  15

Val Ser Leu Thr Leu Phe Pro Val Asn Val Arg Ala Asp Val Val Ile
            20                  25                  30

Thr Ser Asn Gln Thr Gly Thr His Gly Gly Tyr Asn Phe Glu Tyr Trp
        35                  40                  45

Lys Asp Thr Gly Asn Gly Thr Met Val Leu Lys Asp Gly Gly Ala Phe
    50                  55                  60

Ser Cys Glu Trp Ser Asn Ile Asn Asn Ile Leu Phe Arg Lys Gly Phe
65                  70                  75                  80

Lys Tyr Asp Glu Thr Lys Thr His Asp Gln Leu Gly Tyr Ile Thr Val
                85                  90                  95

Thr Tyr Ser Cys Asn Tyr Gln Pro Asn Gly Asn Ser Tyr Leu Gly Val
            100                 105                 110

Tyr Gly Trp Thr Ser Asn Pro Leu Val Glu Tyr Tyr Ile Ile Glu Ser
        115                 120                 125

Trp Gly Thr Trp Arg Pro Pro Gly Ala Thr Pro Lys Gly Thr Ile Thr
    130                 135                 140

Val Asp Gly Gly Thr Tyr Glu Ile Tyr Glu Thr Thr Arg Val Asn Gln
145                 150                 155                 160

Pro Ser Ile Lys Gly Thr Ala Thr Phe Gln Gln Tyr Trp Ser Val Arg
                165                 170                 175

Thr Ser Lys Arg Thr Ser Gly Thr Ile Ser Val Thr Glu His Phe Lys
            180                 185                 190
```

```
Ala Trp Glu Arg Leu Gly Met Lys Met Gly Lys Met Tyr Glu Val Ala
            195                 200                 205
Leu Val Val Glu Gly Tyr Gln Ser Ser Gly Lys Ala Asp Val Thr Ser
210                 215                 220
Met Thr Ile Thr Val Gly Asn Ala Pro Ser Ser Ser Pro Pro Gly
225                 230                 235                 240
Pro Thr Pro Glu Pro Thr Pro Arg Ser Ala Phe Ser Lys Ile Glu Ala
            245                 250                 255
Glu Glu Tyr Asn Ser Leu Lys Ser Ser Thr Ile Gln Thr Ile Gly Thr
            260                 265                 270
Ser Asp Gly Gly Ser Gly Ile Gly Tyr Ile Glu Ser Gly Asp Tyr Leu
            275                 280                 285
Val Phe Asn Lys Ile Asn Phe Gly Asn Gly Ala Asn Ser Phe Lys Ala
            290                 295                 300
Arg Val Ala Ser Gly Ala Asp Thr Pro Thr Asn Ile Gln Leu Arg Leu
305                 310                 315                 320
Gly Ser Pro Thr Gly Thr Leu Ile Gly Thr Leu Thr Val Ala Ser Thr
            325                 330                 335
Gly Gly Trp Asn Asn Tyr Glu Glu Lys Ser Cys Ser Ile Thr Asn Thr
            340                 345                 350
Thr Gly Gln His Asp Leu Tyr Leu Val Phe Ser Gly Pro Val Asn Ile
            355                 360                 365
Asp Tyr Phe Ile Phe Asp Ser Lys Gly Val Asn Pro Thr Pro Thr Pro
            370                 375                 380
Thr Ser Pro Pro Gln Gln Asp Gln Val Leu Gly Asp Leu Asn Gly Asp
385                 390                 395                 400
Lys Gln Val Asn Ser Thr Asp Tyr Thr Ala Leu Lys Arg His Leu Leu
            405                 410                 415
Asn Ile Thr Arg Leu Ser Gly Thr Ala Leu Ala Asn Ala Asp Val Asn
            420                 425                 430
Arg Asp Gly Lys Val Asp Ser Thr Asp Leu Met Met Leu His Arg Tyr
            435                 440                 445
Leu Leu Arg Ile Ile Ser Lys Leu Gly
            450                 455

<210> SEQ ID NO 22
<211> LENGTH: 1008
<212> TYPE: DNA
<213> ORGANISM: Thermobifida halotolerans

<400> SEQUENCE: 22
atgaacgacg cccccgccca cccaaagagc cgcagacacg ccgcatcag   actgttcgtc    60 ggccgtgtct gcaccgccct ggtggcgctg gtcacggcca cgacgatgct gcccggcgtc   120
gccaacgcgg ccgtgacctc caaccagacg ggcacccatg acggctattt ctactcgttc   180
tggaccgaca gccccggaac ggtctccatg gagctgggcc ccgagggcaa ctacagcacc   240
tcgtggagca acaccgggaa cttcgttgtc ggtaagggct ggagcaccgg cggacgcagg   300
accgtgacct actccggtag cttcaacccg tccggtaacg cgtacctgac tctctacggg   360
tggacgagaa acccgctcgt ggagtactac atcgtcgaca actggggcac ctaccggccc   420
acgggaacgt acaagggcac ggtcaccagc gacggcggca cgtacgacat ctacgagacg   480
acgcgcacca cgcccccctc catcgagggc accgcaacct tcaagcagta ctggagcgtc   540
cggcagtcga ggagaacggg cggaaccata accgctggaa accacttcga cgcatgggcc   600
```

```
cgccacggaa tgaacctggg cagccatgac tacatgatca tggcgacgga gggataccag    660
agcagcggga gctccaacat aacggtgggc ggctccggcg gcggcaatcc tggcggaaac    720
cccggcggca accccggtgg cggtggctgc accgcgaccc tgtccgcggg gcagcagtgg    780
agtgaccggt acaacctcgg cgtctcggtc agcggctcca gcaactggac cgtgacgatg    840
aacgtgccgt cccggcgaa gatcatcgcc acgtggaaca tcagcgccag ctaccccaac    900
gcccagacgc tgaccgccag gcccaacggc aacggcaaca ctggggtgt gacgatccag    960 cacaacggca actggacctg ccgacggtc tcctgcagcg cgaactga               1008
```

<210> SEQ ID NO 23
<211> LENGTH: 335
<212> TYPE: PRT
<213> ORGANISM: Thermobifida halotolerans

<400> SEQUENCE: 23

```
Met Asn Asp Ala Pro Ala His Pro Lys Ser Arg Arg His Gly Arg Ile
1               5                  10                  15

Arg Leu Phe Val Gly Arg Val Cys Thr Ala Leu Val Ala Leu Val Thr
            20                  25                  30

Ala Thr Thr Met Leu Pro Gly Val Ala Asn Ala Ala Val Thr Ser Asn
        35                  40                  45

Gln Thr Gly Thr His Asp Gly Tyr Phe Tyr Ser Phe Trp Thr Asp Ser
    50                  55                  60

Pro Gly Thr Val Ser Met Glu Leu Gly Pro Gly Gly Asn Tyr Ser Thr
65                  70                  75                  80

Ser Trp Ser Asn Thr Gly Asn Phe Val Val Gly Lys Gly Trp Ser Thr
                85                  90                  95

Gly Gly Arg Arg Thr Val Thr Tyr Ser Gly Ser Phe Asn Pro Ser Gly
            100                 105                 110

Asn Ala Tyr Leu Thr Leu Tyr Gly Trp Thr Arg Asn Pro Leu Val Glu
        115                 120                 125

Tyr Tyr Ile Val Asp Asn Trp Gly Thr Tyr Arg Pro Thr Gly Thr Tyr
    130                 135                 140

Lys Gly Thr Val Thr Ser Asp Gly Gly Thr Tyr Asp Ile Tyr Glu Thr
145                 150                 155                 160

Thr Arg Thr Asn Ala Pro Ser Ile Glu Gly Thr Ala Thr Phe Lys Gln
                165                 170                 175

Tyr Trp Ser Val Arg Gln Ser Arg Arg Thr Gly Gly Thr Ile Thr Ala
            180                 185                 190

Gly Asn His Phe Asp Ala Trp Ala Arg His Gly Met Asn Leu Gly Ser
        195                 200                 205

His Asp Tyr Met Ile Met Ala Thr Glu Gly Tyr Gln Ser Ser Gly Ser
    210                 215                 220

Ser Asn Ile Thr Val Gly Gly Ser Gly Gly Asn Pro Gly Gly Asn
225                 230                 235                 240

Pro Gly Gly Asn Pro Gly Gly Gly Cys Thr Ala Thr Leu Ser Ala
                245                 250                 255

Gly Gln Gln Trp Ser Asp Arg Tyr Asn Leu Gly Val Ser Val Ser Gly
            260                 265                 270

Ser Ser Asn Trp Thr Val Thr Met Asn Val Pro Ser Pro Ala Lys Ile
        275                 280                 285

Ile Ala Thr Trp Asn Ile Ser Ala Ser Tyr Pro Asn Ala Gln Thr Leu
    290                 295                 300
```

Thr Ala Arg Pro Asn Gly Asn Gly Asn Asn Trp Gly Val Thr Ile Gln
305                 310                 315                 320

His Asn Gly Asn Trp Thr Trp Pro Thr Val Ser Cys Ser Ala Asn
                325                 330                 335

<210> SEQ ID NO 24
<211> LENGTH: 1005
<212> TYPE: DNA
<213> ORGANISM: Thermobispora bispora

<400> SEQUENCE: 24

```
atgttcaggt ccccgagagg ccacgggcgc ggccgtaggt tcatcggccg gatctgcgcc      60
ttagccgtgg cggtgatcac cgggctgacg atgtcggtcg gcaccgccca cgcccagacg     120
atcagctcga accagaccgg ctaccacgac ggctacttct actccttctg gaccgatgcc     180
cccggcacgg tctcgatgac cctcggatcg ggcgggaact acagcacctc gtggtggaac     240
accgggaact tcgtcgcggg taagggctgg gccaccggcg gccgccggac ggtgacctac     300
tcggccagct tcaacccgtc cggcaacgcc tacctggcgc tgtacgggtg gacccgtaac     360
ccgctcgtcg agtactacat cgtcgagagc tggggcaccct accggccgac gggcacctac     420
aagggcaccg tcaccaccga cggcggcacc tacgacatct acgagacgac ccggtacaac     480
gccccctcca tcgagggcac ccggaccttc aagcagttct ggagcgtccg gcagtcgaag     540
cggaccagcg gcaccatcac caccggcaac cacttcgacg cctgggcccg cgcggggatg     600
cagctcggca gcttcgacta catgatcatg gccaccgagg gctaccagag cagcggcaac     660
tccaacgtca ccctgggcac cggcggcggt ggcggcacca cgcctccgcc cggtggcggc     720
ggtggcggtg gcggcggtgg ctgccaggcc acgatcatcc cgggccaggt gtgggccgac     780
cggttcaacc tgtcggtcca ggtcaccggc accgacaact gggtcgtcac ggtcaccgtg     840
accccgccgc agaagatcat cgccacctgg aacggcaatc cgacctggga ttacacaggc     900
aacgtgatga ccatgaggcc caacggcagc gggaacacgt tcggtttcac gatcatgcac     960
aacggcaact ggagctggcc gagcgtgacc tgccgggtgg cctga                    1005
```

<210> SEQ ID NO 25
<211> LENGTH: 334
<212> TYPE: PRT
<213> ORGANISM: Thermobispora bispora

<400> SEQUENCE: 25

Met Phe Arg Ser Pro Arg Gly His Gly Arg Gly Arg Arg Phe Ile Gly
1               5                   10                  15

Arg Ile Cys Ala Leu Ala Val Ala Val Ile Thr Gly Leu Thr Met Ser
                20                  25                  30

Val Gly Thr Ala His Ala Gln Thr Ile Ser Ser Asn Gln Thr Gly Tyr
            35                  40                  45

His Asp Gly Tyr Phe Tyr Ser Phe Trp Thr Asp Ala Pro Gly Thr Val
        50                  55                  60

Ser Met Thr Leu Gly Ser Gly Gly Asn Tyr Ser Thr Ser Trp Trp Asn
65                  70                  75                  80

Thr Gly Asn Phe Val Ala Gly Lys Gly Trp Ala Thr Gly Gly Arg Arg
                85                  90                  95

Thr Val Thr Tyr Ser Ala Ser Phe Asn Pro Ser Gly Asn Ala Tyr Leu
            100                 105                 110

Ala Leu Tyr Gly Trp Thr Arg Asn Pro Leu Val Glu Tyr Tyr Ile Val

```
                   115                 120                 125
Glu Ser Trp Gly Thr Tyr Arg Pro Thr Gly Thr Tyr Lys Gly Thr Val
        130                 135                 140
Thr Thr Asp Gly Gly Thr Tyr Asp Ile Tyr Glu Thr Arg Tyr Asn
145                 150                 155                 160
Ala Pro Ser Ile Glu Gly Thr Arg Thr Phe Lys Gln Phe Trp Ser Val
                165                 170                 175
Arg Gln Ser Lys Arg Thr Ser Gly Thr Ile Thr Thr Gly Asn His Phe
            180                 185                 190
Asp Ala Trp Ala Arg Ala Gly Met Gln Leu Gly Ser Phe Asp Tyr Met
        195                 200                 205
Ile Met Ala Thr Glu Gly Tyr Gln Ser Ser Gly Asn Ser Asn Val Thr
210                 215                 220
Leu Gly Thr Gly Gly Gly Gly Thr Thr Pro Pro Pro Gly Gly Gly
225                 230                 235                 240
Gly Gly Gly Gly Gly Gly Cys Gln Ala Thr Ile Ile Pro Gly Gln
                245                 250                 255
Val Trp Ala Asp Arg Phe Asn Leu Ser Val Gln Val Thr Gly Thr Asp
            260                 265                 270
Asn Trp Val Val Thr Val Thr Val Thr Pro Pro Gln Lys Ile Ile Ala
        275                 280                 285
Thr Trp Asn Gly Asn Pro Thr Trp Asp Tyr Thr Gly Asn Val Met Thr
290                 295                 300
Met Arg Pro Asn Gly Ser Gly Asn Thr Phe Gly Phe Thr Ile Met His
305                 310                 315                 320
Asn Gly Asn Trp Ser Trp Pro Ser Val Thr Cys Arg Val Ala
                325                 330

<210> SEQ ID NO 26
<211> LENGTH: 1035
<212> TYPE: DNA
<213> ORGANISM: Thermopolyspora flexuosa

<400> SEQUENCE: 26
atgaacgaac ccctcaccat cacgcaggcc aggcgccgca cacgcctcgg cctccggcgc      60
atcgtcacca gtgccttcgc cctggcactc gccatcgccg gtgcgctgct gcccggcacg     120
gcccacgccg acaccaccat cacccagaac cagaccgggt acgacaacgg ctacttctac     180
tcgttctgga ccgacgcgcc cgggaccgtc tccatgaccc tccactcggg cggcagctac     240
agcacctcgt ggcggaacac cgggaacttc gtcgccggca agggctggtc caccggcgga     300
cggcggaccg tgacctacaa cgcctccttc aacccgtcgg gtaacgccta cctcacgctc     360
tacggctgga ccaggaaccc gctcgtcgag tactacatcg tcgagagctg gggcacctac     420
cggcccaccg gcacctacaa gggcaccgtc accaccgacg gcggcacgta cgacatctac     480
gagacctggc ggtacaacgc gccgtccatc gagggcaccc ggaccttcca gcagttctgg     540
agcgtccggc agcagaagcg gaccagcggc accatcacca tcggcaacca cttcgacgcc     600
tgggcccgcg ccggcatgaa cctgggcagc cacgactacc agatcatggc gaccgagggc     660
taccagagca gcggtagctc caccgtctcc atcagcgagg tggcaacccc ggcaacccgg     720
ggtaaccccg gcaaccccgg caaccccggt aaccccggta accccggcgg tggctgcgtc     780
gcgaccctct ccgccggcca gcagtggagc gaccgctaca acctcaacgt ctcggtcagc     840
ggctcgaaca actggacggt ccggatggac gtgccctacc cggcccgcat catcgccacc     900
```

-continued

```
tggaacatcc acgcccagtg gcccgagtcc caggtgctca tcgccagacc caacggcaac      960
ggcaacaact gggcgtgac gatccagcac aacggcaact ggacctggcc gacggtcacc      1020
tgtaccgcga actga                                                       1035
```

<210> SEQ ID NO 27
<211> LENGTH: 344
<212> TYPE: PRT
<213> ORGANISM: Thermopolyspora flexuosa

<400> SEQUENCE: 27

```
Met Asn Glu Pro Leu Thr Ile Thr Gln Ala Arg Arg Arg Arg Leu
1               5                   10                  15

Gly Leu Arg Arg Ile Val Thr Ser Ala Phe Ala Leu Ala Leu Ala Ile
            20                  25                  30

Ala Gly Ala Leu Leu Pro Gly Thr Ala His Ala Asp Thr Thr Ile Thr
        35                  40                  45

Gln Asn Gln Thr Gly Tyr Asp Asn Gly Tyr Phe Tyr Ser Phe Trp Thr
    50                  55                  60

Asp Ala Pro Gly Thr Val Ser Met Thr Leu His Ser Gly Gly Ser Tyr
65                  70                  75                  80

Ser Thr Ser Trp Arg Asn Thr Gly Asn Phe Val Ala Gly Lys Gly Trp
                85                  90                  95

Ser Thr Gly Gly Arg Arg Thr Val Thr Tyr Asn Ala Ser Phe Asn Pro
            100                 105                 110

Ser Gly Asn Ala Tyr Leu Thr Leu Tyr Gly Trp Thr Arg Asn Pro Leu
        115                 120                 125

Val Glu Tyr Tyr Ile Val Glu Ser Trp Gly Thr Tyr Arg Pro Thr Gly
    130                 135                 140

Thr Tyr Lys Gly Thr Val Thr Thr Asp Gly Gly Thr Tyr Asp Ile Tyr
145                 150                 155                 160

Glu Thr Trp Arg Tyr Asn Ala Pro Ser Ile Glu Gly Thr Arg Thr Phe
                165                 170                 175

Gln Gln Phe Trp Ser Val Arg Gln Gln Lys Arg Thr Ser Gly Thr Ile
            180                 185                 190

Thr Ile Gly Asn His Phe Asp Ala Trp Ala Arg Ala Gly Met Asn Leu
        195                 200                 205

Gly Ser His Asp Tyr Gln Ile Met Ala Thr Glu Gly Tyr Gln Ser Ser
    210                 215                 220

Gly Ser Ser Thr Val Ser Ile Ser Glu Gly Gly Asn Pro Gly Asn Pro
225                 230                 235                 240

Gly Asn Pro Gly Asn Pro Gly Asn Pro Gly Asn Pro Gly Asn Pro Gly
                245                 250                 255

Gly Gly Cys Val Ala Thr Leu Ser Ala Gly Gln Gln Trp Ser Asp Arg
            260                 265                 270

Tyr Asn Leu Asn Val Ser Val Ser Gly Ser Asn Asn Trp Thr Val Arg
        275                 280                 285

Met Asp Val Pro Tyr Pro Ala Arg Ile Ile Ala Thr Trp Asn Ile His
    290                 295                 300

Ala Gln Trp Pro Glu Ser Gln Val Leu Ile Ala Arg Pro Asn Gly Asn
305                 310                 315                 320

Gly Asn Asn Trp Gly Val Thr Ile Gln His Asn Gly Asn Trp Thr Trp
                325                 330                 335

Pro Thr Val Thr Cys Thr Ala Asn
            340
```

<210> SEQ ID NO 28
<211> LENGTH: 1228
<212> TYPE: PRT
<213> ORGANISM: Acidothermus cellulolyticus

<400> SEQUENCE: 28

```
Met Glu Arg Thr Gln Gln Ser Gly Arg Asn Cys Arg Tyr Gln Arg Gly
1               5                   10                  15

Thr Thr Arg Met Pro Ala Ile Ser Lys Arg Leu Arg Ala Gly Val Leu
            20                  25                  30

Ala Gly Ala Val Ser Ile Ala Ala Ser Ile Val Pro Leu Ala Met Gln
        35                  40                  45

His Pro Ala Ile Ala Ala Thr His Val Asp Asn Pro Tyr Ala Gly Ala
    50                  55                  60

Thr Phe Phe Val Asn Pro Tyr Trp Ala Gln Glu Val Gln Ser Glu Ala
65                  70                  75                  80

Ala Asn Gln Thr Asn Ala Thr Leu Ala Ala Lys Met Arg Val Val Ser
                85                  90                  95

Thr Tyr Ser Thr Ala Val Trp Met Asp Arg Ile Ala Ala Ile Asn Gly
            100                 105                 110

Val Asn Gly Gly Pro Gly Leu Thr Thr Tyr Leu Asp Ala Ala Leu Ser
        115                 120                 125

Gln Gln Gln Gly Thr Thr Pro Glu Val Ile Glu Ile Val Ile Tyr Asp
    130                 135                 140

Leu Pro Gly Arg Asp Cys Ala Ala Leu Ala Ser Asn Gly Glu Leu Pro
145                 150                 155                 160

Ala Thr Ala Ala Gly Leu Gln Thr Tyr Glu Thr Gln Tyr Ile Asp Pro
                165                 170                 175

Ile Ala Ser Ile Leu Ser Asn Pro Lys Tyr Ser Ser Leu Arg Ile Val
            180                 185                 190

Thr Ile Ile Glu Pro Asp Ser Leu Pro Asn Ala Val Thr Asn Met Ser
        195                 200                 205

Ile Gln Ala Cys Ala Thr Ala Val Pro Tyr Tyr Glu Gln Gly Ile Glu
    210                 215                 220

Tyr Ala Leu Thr Lys Leu His Ala Ile Pro Asn Val Tyr Ile Tyr Met
225                 230                 235                 240

Asp Ala Ala His Ser Gly Trp Leu Gly Trp Pro Asn Asn Ala Ser Gly
                245                 250                 255

Tyr Val Gln Glu Val Gln Lys Val Leu Asn Ala Ser Ile Gly Val Asn
            260                 265                 270

Gly Ile Asp Gly Phe Val Thr Asn Thr Ala Asn Tyr Thr Pro Leu Lys
        275                 280                 285

Glu Pro Phe Met Thr Ala Thr Gln Gln Val Gly Gly Gln Pro Val Glu
    290                 295                 300

Ser Ala Asn Phe Tyr Gln Trp Asn Pro Asp Ile Asp Glu Ala Asp Tyr
305                 310                 315                 320

Ala Val Asp Leu Tyr Ser Arg Leu Val Ala Ala Gly Phe Pro Ser Ser
                325                 330                 335

Ile Gly Met Leu Ile Asp Thr Leu Arg Asn Gly Trp Gly Gly Pro Asn
            340                 345                 350

Glu Pro Thr Gly Pro Ser Thr Ala Thr Asp Val Asn Thr Phe Val Asn
        355                 360                 365

Gln Ser Lys Ile Asp Leu Arg Gln His Arg Gly Leu Trp Cys Asn Gln
```

```
              370                 375                 380
Asn Gly Ala Gly Leu Gly Gln Pro Pro Gln Ala Ser Pro Thr Asp Phe
385                 390                 395                 400

Pro Asn Ala His Leu Asp Ala Tyr Val Trp Ile Lys Pro Pro Gly Glu
                405                 410                 415

Ser Asp Gly Thr Ser Ala Ala Ser Asp Pro Thr Thr Gly Lys Lys Ser
                420                 425                 430

Asp Pro Met Cys Asp Pro Thr Tyr Thr Thr Ser Tyr Gly Val Leu Thr
                435                 440                 445

Asn Ala Leu Pro Asn Ser Pro Ile Ala Gly Gln Trp Phe Pro Ala Gln
            450                 455                 460

Phe Asp Gln Leu Val Ala Asn Ala Arg Pro Ala Val Pro Thr Ser Thr
465                 470                 475                 480

Ser Ser Ser Pro Pro Pro Pro Ser Pro Ser Ala Ser Pro Ser
                    485                 490                 495

Pro Ser Pro Ser Pro Ser Pro Ser Ser Ser Pro Ser Pro Ser Pro Ser
                500                 505                 510

Pro Ser Ser Ser Pro Ser Pro Ser Pro Ser Pro Ser Pro Ser Pro Ser
                515                 520                 525

Ser Ser Pro Ser Pro Ser Pro Ser Ser Ser Pro Ser Pro Ser Pro Ser
            530                 535                 540

Pro Ser Pro Ser Pro Ser Ser Ser Pro Ser Pro Ser Pro Ser Ser Ser
545                 550                 555                 560

Pro Ser Pro Ser Pro Ser Pro Ser Pro Ser Ser Ser Pro Ser
                    565                 570                 575

Pro Ser Pro Thr Ser Ser Pro Val Ser Gly Gly Leu Lys Val Gln Tyr
                580                 585                 590

Lys Asn Asn Asp Ser Ala Pro Gly Asp Asn Gln Ile Lys Pro Gly Leu
                595                 600                 605

Gln Leu Val Asn Thr Gly Ser Ser Ser Val Asp Leu Ser Thr Val Thr
                610                 615                 620

Val Arg Tyr Trp Phe Thr Arg Asp Gly Gly Ser Ser Thr Leu Val Tyr
625                 630                 635                 640

Asn Cys Asp Trp Ala Ala Met Gly Cys Gly Asn Ile Arg Ala Ser Phe
                    645                 650                 655

Gly Ser Val Asn Pro Ala Thr Pro Thr Ala Asp Thr Tyr Leu Gln Leu
                660                 665                 670

Ser Phe Thr Gly Gly Thr Leu Ala Ala Gly Gly Ser Thr Gly Glu Ile
                675                 680                 685

Gln Asn Arg Val Asn Lys Ser Asp Trp Ser Asn Phe Thr Glu Thr Asn
            690                 695                 700

Asp Tyr Ser Tyr Gly Thr Asn Thr Thr Phe Gln Asp Trp Thr Lys Val
705                 710                 715                 720

Thr Val Tyr Val Asn Gly Val Leu Val Trp Gly Thr Glu Pro Ser Gly
                    725                 730                 735

Thr Ser Pro Ser Pro Thr Pro Ser Pro Ser Pro Ser Pro Ser Pro Ser
                740                 745                 750

Pro Gly Gly Asp Val Thr Pro Ser Val Pro Thr Gly Leu Val Val
                755                 760                 765

Thr Gly Val Ser Gly Ser Ser Val Ser Leu Ala Trp Asn Ala Ser Thr
            770                 775                 780

Asp Asn Val Gly Val Ala His Tyr Asn Val Tyr Arg Asn Gly Val Leu
785                 790                 795                 800
```

-continued

```
Val Gly Gln Pro Thr Val Thr Ser Phe Thr Asp Thr Gly Leu Ala Ala
            805                 810                 815

Gly Thr Ala Tyr Thr Tyr Val Ala Ala Val Asp Ala Ala Gly Asn
            820                 825                 830

Thr Ser Ala Pro Ser Thr Pro Val Thr Ala Thr Thr Ser Pro Ser
            835                 840                 845

Pro Ser Pro Thr Pro Thr Gly Thr Thr Val Asp Cys Thr Pro Gly
        850                 855                 860

Pro Asn Gln Asn Gly Val Thr Ser Val Gln Gly Asp Glu Tyr Arg Val
865                 870                 875                 880

Gln Thr Asn Glu Trp Asn Ser Ser Ala Gln Gln Cys Leu Thr Ile Asn
                885                 890                 895

Thr Ala Thr Gly Ala Trp Thr Val Ser Thr Ala Asn Phe Ser Gly Gly
                900                 905                 910

Thr Gly Gly Ala Pro Ala Thr Tyr Pro Ser Ile Tyr Lys Gly Cys His
            915                 920                 925

Trp Gly Asn Cys Thr Thr Lys Asn Val Gly Met Pro Ile Gln Ile Ser
        930                 935                 940

Gln Ile Gly Ser Ala Val Thr Ser Trp Ser Thr Thr Gln Val Ser Ser
945                 950                 955                 960

Gly Ala Tyr Asp Val Ala Tyr Asp Ile Trp Thr Asn Ser Thr Pro Thr
                965                 970                 975

Thr Thr Gly Gln Pro Asn Gly Thr Glu Ile Met Ile Trp Leu Asn Ser
            980                 985                 990

Arg Gly Gly Val Gln Pro Phe Gly Ser Gln Thr Ala Thr Gly Val Thr
            995                 1000                1005

Val Ala Gly His Thr Trp Asn Val Trp Gln Gly Gln Gln Thr Ser
        1010                1015                1020

Trp Lys Ile Ile Ser Tyr Val Leu Thr Pro Gly Ala Thr Ser Ile
        1025                1030                1035

Ser Asn Leu Asp Leu Lys Ala Ile Phe Ala Asp Ala Ala Ala Arg
        1040                1045                1050

Gly Ser Leu Asn Thr Ser Asp Tyr Leu Leu Asp Val Glu Ala Gly
        1055                1060                1065

Phe Glu Ile Trp Gln Gly Gly Gln Gly Leu Gly Ser Asn Ser Phe
        1070                1075                1080

Ser Val Ser Val Thr Ser Gly Thr Ser Ser Pro Thr Pro Ser Pro
        1085                1090                1095

Ser Pro Thr Pro Thr Pro Ser Pro Thr Pro Thr Pro Ser Pro Ser
        1100                1105                1110

Pro Thr Pro Ser Pro Ser Pro Thr Ser Ser Pro Ser Ser Ser Gly
        1115                1120                1125

Val Ala Cys Arg Ala Thr Tyr Val Val Asn Ser Asp Trp Gly Ser
        1130                1135                1140

Gly Phe Thr Ala Thr Val Thr Val Thr Asn Thr Gly Ser Arg Ala
        1145                1150                1155

Thr Asn Gly Trp Thr Val Ala Trp Ser Phe Gly Gly Asn Gln Thr
        1160                1165                1170

Val Thr Asn Tyr Trp Asn Thr Ala Leu Thr Gln Ser Gly Ala Ser
        1175                1180                1185

Val Thr Ala Thr Asn Leu Ser Tyr Asn Asn Val Ile Gln Pro Gly
        1190                1195                1200
```

Gln Ser Thr Thr Phe Gly Phe Asn Gly Ser Tyr Ser Gly Thr Asn
    1205                1210                1215

Ala Ala Pro Thr Leu Ser Cys Thr Ala Ser
    1220                1225

<210> SEQ ID NO 29
<211> LENGTH: 1371
<212> TYPE: DNA
<213> ORGANISM: Thermobispora bispora

<400> SEQUENCE: 29

```
atgtctcgaa taaggcgctt tttggccaca gcgctcgccg cggccaccgc cggcgtgggg      60
gcgatcgtca ccgccatcgc ctcggccggc cccgctcacg cctatgactc gcccttctac     120
gtggacccgc agagcaacgc ggccaagtgg gtggcggcca accccaacga cccccggacg     180
ccggtgatcc gggaccggat cgccgcggtg ccgaccggcc gctggttcgc caactacaac     240
ccctcgaccg tgcgcgccga ggtcgacgcg tacgtcggcg ccgcggccgc ggccgggaag     300
atcccgatca tggtcgtgta cgccatgccg aaccgggact cggcgggcc gagcgcgggc      360
ggtgccccca accacaccgc ctaccgcgcc tggatcgatg agatcgccgc cggcctccgc     420
aaccgcccgg ccgtgatcat cctggagccg acgcgctcc cgatcatgac caactgcatg      480
agccccagcg agcaggccga ggtccaggcc tccatggcgt acgcgggcaa gaagttcaag     540
gccgcctcgt cgcaggcgaa ggtctacttc gacgccggcc acgacgcctg gtcccggcg      600
gacgagatgg cctcccgcct caggggcgcc gacatcgcca acagcgcgga cggcatcgcg     660
ctcaacgtct ccaactaccg gtacacctcg ggcctgatct cgtacgccaa gagcgtcctc     720
tcggcgatcg gcgcgtcgca cctgcgcgcg gtcatcgaca ccagccggaa cggcaacggc     780
ccgctcggca gcgagtggtg cgacccgccg ggccgcgcca ccggcacctg gagcaccacg     840
gacaccggcg acccggcgat cgacgccttc ctgtggatca gccgccggg tgaggccgac     900
gggtgcatcg ccacgccggg tgtcttcgtc ccggaccggg cctacgagct cgccatgaac     960
gcggcgccgc ccacgtacag cccgtcgccc acgccgagca gccctcccc ctcgccgtcc     1020
cagagcgacc cgggttcgcc ctcgccgtcg ccgtcccagc cgccggcggg caaggcgtgc    1080
gaggccacgt acgcgctggt caaccagtgg ccggcggct tccaggccga ggtgaccgtg     1140
aagaacaccg ctcctcgcc gatcaacggg tggaccgttc agtggaccct gccgagcggc     1200
cagtccatca cccagctgtg gaacggtgac ctgtccacca gcggctcgaa cgtcaccgtc    1260
cggaacgtga gctggaacgg caacgtgccg gccggcggct ccacctcgtt cggcttcctc    1320
ggctcgggca ccggccagct ctcctcctcc atcacctgct cggcgagctg a             1371
```

<210> SEQ ID NO 30
<211> LENGTH: 456
<212> TYPE: PRT
<213> ORGANISM: Thermobispora bispora

<400> SEQUENCE: 30

Met Ser Arg Ile Arg Arg Phe Leu Ala Thr Ala Leu Ala Ala Ala Thr
1               5                   10                  15

Ala Gly Val Gly Ala Ile Val Thr Ala Ile Ala Ser Ala Gly Pro Ala
            20                  25                  30

His Ala Tyr Asp Ser Pro Phe Tyr Val Asp Pro Gln Ser Asn Ala Ala
        35                  40                  45

Lys Trp Val Ala Ala Asn Pro Asn Asp Pro Arg Thr Pro Val Ile Arg
    50                  55                  60

-continued

```
Asp Arg Ile Ala Ala Val Pro Thr Gly Arg Trp Phe Ala Asn Tyr Asn
 65                  70                  75                  80

Pro Ser Thr Val Arg Ala Glu Val Asp Ala Tyr Val Gly Ala Ala Ala
             85                  90                  95

Ala Ala Gly Lys Ile Pro Ile Met Val Val Tyr Ala Met Pro Asn Arg
            100                 105                 110

Asp Cys Gly Gly Pro Ser Ala Gly Ala Pro Asn His Thr Ala Tyr
        115                 120                 125

Arg Ala Trp Ile Asp Glu Ile Ala Ala Gly Leu Arg Asn Arg Pro Ala
        130                 135                 140

Val Ile Ile Leu Glu Pro Asp Ala Leu Pro Ile Met Thr Asn Cys Met
145                 150                 155                 160

Ser Pro Ser Glu Gln Ala Glu Val Gln Ala Ser Met Ala Tyr Ala Gly
            165                 170                 175

Lys Lys Phe Lys Ala Ala Ser Ser Gln Ala Lys Val Tyr Phe Asp Ala
            180                 185                 190

Gly His Asp Ala Trp Val Pro Ala Asp Glu Met Ala Ser Arg Leu Arg
        195                 200                 205

Gly Ala Asp Ile Ala Asn Ser Ala Asp Gly Ile Ala Leu Asn Val Ser
210                 215                 220

Asn Tyr Arg Tyr Thr Ser Gly Leu Ile Ser Tyr Ala Lys Ser Val Leu
225                 230                 235                 240

Ser Ala Ile Gly Ala Ser His Leu Arg Ala Val Ile Asp Thr Ser Arg
            245                 250                 255

Asn Gly Asn Gly Pro Leu Gly Ser Glu Trp Cys Asp Pro Pro Gly Arg
            260                 265                 270

Ala Thr Gly Thr Trp Ser Thr Thr Asp Thr Gly Asp Pro Ala Ile Asp
            275                 280                 285

Ala Phe Leu Trp Ile Lys Pro Pro Gly Glu Ala Asp Gly Cys Ile Ala
        290                 295                 300

Thr Pro Gly Val Phe Val Pro Asp Arg Ala Tyr Glu Leu Ala Met Asn
305                 310                 315                 320

Ala Ala Pro Pro Thr Tyr Ser Pro Ser Pro Thr Pro Ser Ser Pro Ser
            325                 330                 335

Pro Ser Pro Ser Gln Ser Asp Pro Gly Ser Pro Ser Pro Ser Pro Ser
            340                 345                 350

Gln Pro Pro Ala Gly Lys Ala Cys Glu Ala Thr Tyr Ala Leu Val Asn
        355                 360                 365

Gln Trp Pro Gly Gly Phe Gln Ala Glu Val Thr Val Lys Asn Thr Gly
        370                 375                 380

Ser Ser Pro Ile Asn Gly Trp Thr Val Gln Trp Thr Leu Pro Ser Gly
385                 390                 395                 400

Gln Ser Ile Thr Gln Leu Trp Asn Gly Asp Leu Ser Thr Ser Gly Ser
            405                 410                 415

Asn Val Thr Val Arg Asn Val Ser Trp Asn Gly Asn Val Pro Ala Gly
            420                 425                 430

Gly Ser Thr Ser Phe Gly Phe Leu Gly Ser Gly Thr Gly Gln Leu Ser
        435                 440                 445

Ser Ser Ile Thr Cys Ser Ala Ser
450                 455
```

<210> SEQ ID NO 31
<211> LENGTH: 1260

<212> TYPE: DNA
<213> ORGANISM: Themomonospora curvata

<400> SEQUENCE: 31

```
atggcacccc ctcgcggcgc cccggccccc gtgcgcgccc ggctgcgcgc ctggtcggcc      60
cgctgcgccg cgctcgcgac cgcggcggcc ctcaccgccg cagcggcgcc gcccgcccag     120
gcgcatgccg ccggcaaccc cctgcagggc cgagggcgg cgaaggtccg cttcttcgtc      180
gaacccgaca ccaacgccgg acggcaggcc cgggtgtggg ccgcgcaggg acgcttccac    240
gacgccgccc tcatgcgggc gctgtcgaag atctcccagg cggtctggtt caccgaggga    300
actccccagc aggtgcagcg gcgggtccgc gagaccatgc gccaggcccg ccgccaaggc   360
gccgtccccg tgctggtggc ctactacgtg ccgggacggg actgctcgca gtactcggcc   420
ggcggcgccc ccagcgagcg ggcctaccgg gagtggatca acgccttcgc ccgcggcatc    480
ggcggcggcc gggccgtggt gatcgtcgaa cccgacgggc tggccctgct gtccagcgag    540
ccgtggtgca acgaaggcgg cggcggctcc accggccggc cggaggacat gtcgctggtc    600
gagcagcgct tccgggagat cgaccacgcc atcaccacct tcgccaagct ccccaacacc   660
ggcgtgtacg tggacgccgg ccactcggcc tggcagccgc tcaacgacta cgacgccggc   720
tacggcgagc cgcgcgccca gctcggcatc gtcagccgcc tgctgcgcgg cggcgtcgcc   780
aaggccgacg ggttcgtgct gaacgtctcc aactaccggg ccgacgccga gctgatcgac   840
tacggcgtcc gggtctccaa gtgcctgtgg ctgcgccgca gcaccggcgc gcgcgagtgc    900
accgacgccg acctggccgc cgtgcccgac ggccggcgcg acctgacccc cttcgtcctg    960
gacaccagcc gcaacggccg ggggccgtgg acggcgccgg agggcgcgta ccccgacccc   1020
caggagtggt gcaacccgcc cggccgcggc ctgggcgtcc gccccaccac ccgcaccggc   1080
caccgcctgg tggacgcctt cctgtgggtc aaacggcccg gcgagtccga cggccagtgc   1140
acccgcggca ccgccggacc gcaggacccc gagtacggca tcgtcgaccc gcccgcgggc   1200
cagtggtggc ccgagtacgc cctgggcctg gcccggcggg ccgtgccacc cctcaagtga   1260
```

<210> SEQ ID NO 32
<211> LENGTH: 419
<212> TYPE: PRT
<213> ORGANISM: Themomonospora curvata

<400> SEQUENCE: 32

Met Ala Pro Pro Arg Gly Ala Pro Ala Val Arg Ala Arg Leu Arg
1               5                   10                  15

Ala Trp Ser Ala Arg Cys Ala Ala Leu Ala Thr Ala Ala Leu Thr
                20                  25                  30

Ala Ala Ala Ala Pro Ala Gln Ala His Ala Ala Gly Asn Pro Leu
            35                  40                  45

Gln Gly Pro Arg Ala Ala Lys Val Arg Phe Phe Val Glu Pro Asp Thr
        50                  55                  60

Asn Ala Gly Arg Gln Ala Arg Val Trp Ala Ala Gln Gly Arg Phe His
65                  70                  75                  80

Asp Ala Ala Leu Met Arg Ala Leu Ser Lys Ile Ser Gln Ala Val Trp
                85                  90                  95

Phe Thr Glu Gly Thr Pro Gln Gln Val Gln Arg Arg Val Arg Glu Thr
            100                 105                 110

Met Arg Gln Ala Arg Arg Gln Gly Ala Val Pro Val Leu Val Ala Tyr
        115                 120                 125

Tyr Val Pro Gly Arg Asp Cys Ser Gln Tyr Ser Ala Gly Gly Ala Pro
            130                 135                 140

Ser Glu Arg Ala Tyr Arg Glu Trp Ile Asn Ala Phe Ala Arg Gly Ile
145                 150                 155                 160

Gly Gly Gly Arg Ala Val Val Ile Val Glu Pro Asp Gly Leu Ala Leu
                165                 170                 175

Leu Ser Ser Glu Pro Trp Cys Asn Glu Gly Gly Gly Ser Thr Gly
            180                 185                 190

Arg Pro Glu Asp Met Ser Leu Val Glu Gln Arg Phe Arg Glu Ile Asp
            195                 200                 205

His Ala Ile Thr Thr Phe Ala Lys Leu Pro Asn Thr Gly Val Tyr Val
    210                 215                 220

Asp Ala Gly His Ser Ala Trp Gln Pro Leu Asn Asp Tyr Asp Ala Gly
225                 230                 235                 240

Tyr Gly Glu Pro Arg Ala Gln Leu Gly Ile Val Ser Arg Leu Leu Arg
                245                 250                 255

Gly Gly Val Ala Lys Ala Asp Gly Phe Val Leu Asn Val Ser Asn Tyr
            260                 265                 270

Arg Ala Asp Ala Glu Leu Ile Asp Tyr Gly Val Arg Val Ser Lys Cys
            275                 280                 285

Leu Trp Leu Arg Arg Ser Thr Gly Ala Arg Glu Cys Thr Asp Ala Asp
    290                 295                 300

Leu Ala Ala Val Pro Asp Gly Arg Arg Asp Leu Thr Pro Phe Val Leu
305                 310                 315                 320

Asp Thr Ser Arg Asn Gly Arg Gly Pro Trp Thr Ala Pro Glu Gly Ala
                325                 330                 335

Tyr Pro Asp Pro Gln Glu Trp Cys Asn Pro Pro Gly Arg Gly Leu Gly
            340                 345                 350

Val Arg Pro Thr Thr Arg Thr Gly His Arg Leu Val Asp Ala Phe Leu
            355                 360                 365

Trp Val Lys Arg Pro Gly Glu Ser Asp Gly Gln Cys Thr Arg Gly Thr
    370                 375                 380

Ala Gly Pro Gln Asp Pro Glu Tyr Gly Ile Val Asp Pro Pro Ala Gly
385                 390                 395                 400

Gln Trp Trp Pro Glu Tyr Ala Leu Gly Leu Ala Arg Arg Ala Val Pro
                405                 410                 415

Pro Leu Lys

<210> SEQ ID NO 33
<211> LENGTH: 1152
<212> TYPE: DNA
<213> ORGANISM: Zymomonas mobilis

<400> SEQUENCE: 33
atggcttctt caactttta tattcctttc gtcaacgaaa tgggcgaagg ttcgcttgaa      60
aaagcaatca aggatcttaa cggcagcggc tttaaaaatg ccctgatcgt ttctgatgct     120
ttcatgaaca atccggtgt tgtgaagcag gttgctgacc tgttgaaaac acagggtatt     180
aattctgctg tttatgatgg cgttatgccg aacccgactg ttaccgcagt tctggaaggc     240
cttaagatcc tgaaggataa caattcagac ttcgtcatct ccctcggtgg tggttctccc     300
catgactgcg ccaaagccat cgctctggtc gcaaccaatg gtggtgaagt caaagactac     360
gaaggtatcg acaaatctaa gaaacctgcc ctgccttga tgtcaatcaa cacgacggct      420
ggtacggctt ctgaaatgac gcgtttctgc atcatcactg atgaagtccg tcacgttaag     480

```
atggccattg ttgaccgtca cgttaccccg atggtttccg tcaacgatcc tctgttgatg      540
gttggtatgc caaaaggcct gaccgccgcc accggtatgg atgctctgac ccacgcattt      600
gaagcttatt cttcaacggc agctactccg atcaccgatg cttgcgcttt gaaagcagct      660
tccatgatcg ctaagaatct gaagaccgct tgcgacaacg gtaaggatat gccagctcgt      720
gaagctatgg cttatgccca attcctcgct ggtatggcct tcaacaacgc ttcgcttggt      780
tatgtccatg ctatggctca ccagttgggc ggttactaca acctgccgca tggtgtctgc      840
aacgctgttc tgcttccgca tgttctggct tataacgcct ctgtcgttgc tggtcgtctg      900
aaagacgttg tgttgctat gggtctcgat atcgccaatc tcggcgataa agaaggcgca      960
gaagccacca ttcaggctgt tcgcgatctg gctgcttcca ttggtattcc agcaaatctg     1020
accgagctgg gtgctaagaa agaagatgtg ccgcttcttg ctgaccacgc tctgaaagat     1080
gcttgtgctc tgaccaaccc gcgtcagggt gatcagaaag aagttgaaga actcttcctg     1140
agcgctttct aa                                                         1152
```

<210> SEQ ID NO 34
<211> LENGTH: 383
<212> TYPE: PRT
<213> ORGANISM: Zymomonas mobilis

<400> SEQUENCE: 34

```
Met Ala Ser Ser Thr Phe Tyr Ile Pro Phe Val Asn Glu Met Gly Glu
1               5                   10                  15

Gly Ser Leu Glu Lys Ala Ile Lys Asp Leu Asn Gly Ser Gly Phe Lys
            20                  25                  30

Asn Ala Leu Ile Val Ser Asp Ala Phe Met Asn Lys Ser Gly Val Val
        35                  40                  45

Lys Gln Val Ala Asp Leu Leu Lys Thr Gln Gly Ile Asn Ser Ala Val
    50                  55                  60

Tyr Asp Gly Val Met Pro Asn Pro Thr Val Thr Ala Val Leu Glu Gly
65                  70                  75                  80

Leu Lys Ile Leu Lys Asp Asn Asn Ser Asp Phe Val Ile Ser Leu Gly
                85                  90                  95

Gly Gly Ser Pro His Asp Cys Ala Lys Ala Ile Ala Leu Val Ala Thr
            100                 105                 110

Asn Gly Gly Glu Val Lys Asp Tyr Glu Gly Ile Asp Lys Ser Lys Lys
        115                 120                 125

Pro Ala Leu Pro Leu Met Ser Ile Asn Thr Thr Ala Gly Thr Ala Ser
    130                 135                 140

Glu Met Thr Arg Phe Cys Ile Ile Thr Asp Glu Val Arg His Val Lys
145                 150                 155                 160

Met Ala Ile Val Asp Arg His Val Thr Pro Met Val Ser Val Asn Asp
                165                 170                 175

Pro Leu Leu Met Val Gly Met Pro Lys Gly Leu Thr Ala Ala Thr Gly
            180                 185                 190

Met Asp Ala Leu Thr His Ala Phe Glu Ala Tyr Ser Ser Thr Ala Ala
        195                 200                 205

Thr Pro Ile Thr Asp Ala Cys Ala Leu Lys Ala Ala Ser Met Ile Ala
    210                 215                 220

Lys Asn Leu Lys Thr Ala Cys Asp Asn Gly Lys Asp Met Pro Ala Arg
225                 230                 235                 240

Glu Ala Met Ala Tyr Ala Gln Phe Leu Ala Gly Met Ala Phe Asn Asn
```

```
                    245                 250                 255
Ala Ser Leu Gly Tyr Val His Ala Met Ala His Gln Leu Gly Gly Tyr
                260                 265                 270

Tyr Asn Leu Pro His Gly Val Cys Asn Ala Val Leu Leu Pro His Val
            275                 280                 285

Leu Ala Tyr Asn Ala Ser Val Val Ala Gly Arg Leu Lys Asp Val Gly
        290                 295                 300

Val Ala Met Gly Leu Asp Ile Ala Asn Leu Gly Asp Lys Glu Gly Ala
305                 310                 315                 320

Glu Ala Thr Ile Gln Ala Val Arg Asp Leu Ala Ala Ser Ile Gly Ile
                325                 330                 335

Pro Ala Asn Leu Thr Glu Leu Gly Ala Lys Lys Glu Asp Val Pro Leu
            340                 345                 350

Leu Ala Asp His Ala Leu Lys Asp Ala Cys Ala Leu Thr Asn Pro Arg
        355                 360                 365

Gln Gly Asp Gln Lys Glu Val Glu Glu Leu Phe Leu Ser Ala Phe
    370                 375                 380

<210> SEQ ID NO 35
<211> LENGTH: 1707
<212> TYPE: DNA
<213> ORGANISM: Zymomonas mobilis

<400> SEQUENCE: 35
atgagttata ctgtcggtac ctatttagcg gagcggcttg tccagattgg tctcaagcat      60
cacttcgcag tcgcgggcga ctacaacctc gtccttcttg caacctgct tttgaacaaa      120 aacatggagc aggtttattg ctgtaacgaa ctgaactgcg gtttcagtgc agaaggttat     180
gctcgtgcca aggcgcagc agcagccgtc gttacctaca cgtcggtgc gctttccgca      240 tttgatgcta tcggtggcgc ctatgcagaa aaccttccgg ttatcctgat ctccggtgct     300
ccgaacaaca atgatcacgc tgctggtcac gtgttgcatc acgctcttgg caaaaccgac     360
tatcactatc agttggaaat ggccaagaac atcacggccg ccgctgaagc gatttacacc     420
ccggaagaag ctccggctaa aatcgatcac gtgattaaaa ctgctcttcg tgagaagaag     480
ccggtttatc tcgaaatcgc ttgcaacatt gcttccatgc cctgcgccgc tcctggaccg     540
gcaagcgcat tgttcaatga cgaagccagc gacgaagctt ctttgaatgc agcggttgaa     600
gaaaccctga attcatcgc caaccgcgac aaagttgccg tcctcgtcgg cagcaagctg     660
cgcgcagctg gtgctgaaga gctgctgtc aaatttgctg atgctctcgg tggcgcagtt     720
gctaccatgg ctgctgcaaa aagcttcttc ccagaagaaa acccgcatta tcggcacc      780 tcatggggtg aagtcagcta tccgggcgtt gaaaagacga tgaaagaagc cgatgcggtt     840
atcgctctgg ctcctgtctt caacgactac tccaccactg gttggacgga tattcctgat     900
cctaagaaac tggttctcgc tgaaccgcgt tctgtcgtcg ttaacggcat tgcttcccc      960 agcgtccatc tgaaagacta tctgacccgt ttggctcaga aagtttccaa gaaaaccggt    1020
gctttggact tcttcaaatc cctcaatgca ggtgaactga agaaagccgc tccggctgat    1080
ccgagtgctc cgttggtcaa cgcagaaatc gcccgtcagg tcgaagctct tctgacccg    1140 aacacgacgg ttattgctga aaccggtgac tcttggttca atgctcagcg catgaagctc    1200
ccgaacggtg ctcgcgttga atatgaaatg cagtggggtc acattggttg gtctgttcct    1260
gccgccttcg ttatgccgt cggtgctccg gaacgtcgca acatcctcat ggttggtgat    1320
ggttccttcc agctgacggc tcaggaagtc gctcagatgg ttcgcctgaa actgccggtt    1380
```

```
atcatcttct tgatcaataa ctatggttac accattgaag ttatgatcca tgatggtccg    1440
tacaacaaca tcaagaactg ggattatgcc ggtctgatgg aagtgttcaa cggtaacggt    1500
ggttatgaca gcggtgctgg taaaggcctg aaggctaaaa ccggtggcga actggcagaa    1560
gctatcaagg ttgctctggc aaacaccgac ggcccaaccc tgatcgaatg cttcatcggt    1620
cgtgaagact gcactgaaga attggtcaaa tggggtaagc gcgttgctgc cgccaacagc    1680
cgtaagcctg ttaacaagct cctctag                                        1707

<210> SEQ ID NO 36
<211> LENGTH: 568
<212> TYPE: PRT
<213> ORGANISM: Zymomonas mobilis

<400> SEQUENCE: 36

Met Ser Tyr Thr Val Gly Thr Tyr Leu Ala Glu Arg Leu Val Gln Ile
1               5                   10                  15

Gly Leu Lys His His Phe Ala Val Ala Gly Asp Tyr Asn Leu Val Leu
            20                  25                  30

Leu Asp Asn Leu Leu Leu Asn Lys Asn Met Glu Gln Val Tyr Cys Cys
        35                  40                  45

Asn Glu Leu Asn Cys Gly Phe Ser Ala Glu Gly Tyr Ala Arg Ala Lys
    50                  55                  60

Gly Ala Ala Ala Ala Val Val Thr Tyr Ser Val Gly Ala Leu Ser Ala
65                  70                  75                  80

Phe Asp Ala Ile Gly Gly Ala Tyr Ala Glu Asn Leu Pro Val Ile Leu
                85                  90                  95

Ile Ser Gly Ala Pro Asn Asn Asn Asp His Ala Ala Gly His Val Leu
            100                 105                 110

His His Ala Leu Gly Lys Thr Asp Tyr His Tyr Gln Leu Glu Met Ala
        115                 120                 125

Lys Asn Ile Thr Ala Ala Ala Glu Ala Ile Tyr Thr Pro Glu Glu Ala
    130                 135                 140

Pro Ala Lys Ile Asp His Val Ile Lys Thr Ala Leu Arg Glu Lys Lys
145                 150                 155                 160

Pro Val Tyr Leu Glu Ile Ala Cys Asn Ile Ala Ser Met Pro Cys Ala
                165                 170                 175

Ala Pro Gly Pro Ala Ser Ala Leu Phe Asn Asp Glu Ala Ser Asp Glu
            180                 185                 190

Ala Ser Leu Asn Ala Ala Val Glu Glu Thr Leu Lys Phe Ile Ala Asn
        195                 200                 205

Arg Asp Lys Val Ala Val Leu Val Gly Ser Lys Leu Arg Ala Ala Gly
    210                 215                 220

Ala Glu Glu Ala Ala Val Lys Phe Ala Asp Ala Leu Gly Gly Ala Val
225                 230                 235                 240

Ala Thr Met Ala Ala Ala Lys Ser Phe Phe Pro Glu Glu Asn Pro His
                245                 250                 255

Tyr Ile Gly Thr Ser Trp Gly Glu Val Ser Tyr Pro Gly Val Glu Lys
            260                 265                 270

Thr Met Lys Glu Ala Asp Ala Val Ile Ala Leu Ala Pro Val Phe Asn
        275                 280                 285

Asp Tyr Ser Thr Thr Gly Trp Thr Asp Ile Pro Asp Pro Lys Lys Leu
    290                 295                 300

Val Leu Ala Glu Pro Arg Ser Val Val Val Asn Gly Ile Arg Phe Pro
```

```
                305                 310                 315                 320
        Ser Val His Leu Lys Asp Tyr Leu Thr Arg Leu Ala Gln Lys Val Ser
                        325                 330                 335

Lys Lys Thr Gly Ala Leu Asp Phe Phe Lys Ser Leu Asn Ala Gly Glu
                        340                 345                 350

Leu Lys Lys Ala Ala Pro Ala Asp Pro Ser Ala Pro Leu Val Asn Ala
                        355                 360                 365

Glu Ile Ala Arg Gln Val Glu Ala Leu Leu Thr Pro Asn Thr Thr Val
                370                 375                 380

Ile Ala Glu Thr Gly Asp Ser Trp Phe Asn Ala Gln Arg Met Lys Leu
        385                 390                 395                 400

Pro Asn Gly Ala Arg Val Glu Tyr Glu Met Gln Trp Gly His Ile Gly
                        405                 410                 415

Trp Ser Val Pro Ala Ala Phe Gly Tyr Ala Val Gly Ala Pro Glu Arg
                        420                 425                 430

Arg Asn Ile Leu Met Val Gly Asp Gly Ser Phe Gln Leu Thr Ala Gln
                        435                 440                 445

Glu Val Ala Gln Met Val Arg Leu Lys Leu Pro Val Ile Ile Phe Leu
                450                 455                 460

Ile Asn Asn Tyr Gly Tyr Thr Ile Glu Val Met Ile His Asp Gly Pro
        465                 470                 475                 480

Tyr Asn Asn Ile Lys Asn Trp Asp Tyr Ala Gly Leu Met Glu Val Phe
                        485                 490                 495

Asn Gly Asn Gly Gly Tyr Asp Ser Gly Ala Gly Lys Gly Leu Lys Ala
                        500                 505                 510

Lys Thr Gly Gly Glu Leu Ala Glu Ala Ile Lys Val Ala Leu Ala Asn
                        515                 520                 525

Thr Asp Gly Pro Thr Leu Ile Glu Cys Phe Ile Gly Arg Glu Asp Cys
                530                 535                 540

Thr Glu Glu Leu Val Lys Trp Gly Lys Arg Val Ala Ala Ala Asn Ser
        545                 550                 555                 560

Arg Lys Pro Val Asn Lys Leu Leu
                        565

<210> SEQ ID NO 37
<211> LENGTH: 1659
<212> TYPE: DNA
<213> ORGANISM: Sarcina ventriculi

<400> SEQUENCE: 37
atgaaaataa caattgcaga atacttatta aaaagattaa agaagtaaaa tgtagagcat      60
atgtttggag ttcctggaga ttataactta ggattttttag attatgttga agattctaaa    120
gatattgaat gggttggaag ctgtaatgaa cttaatgcag atatgcagc agatggatat     180 gcaagactta gaggatttgg tgtaatactt acaacttatg gagttggttc acttagtgca    240
ataaatgcta caacaggttc atttgcagaa atgttccag tattacatat atcaggtgta     300
ccatcagctt tagttcaaca aaacagaaag ctagttcacc attcaactgc tagaggagaa    360
ttcgacactt tgaaagaat gtttagaaa ataacagaat tcaatcaat cataagcgaa      420 tataatgcag ctgaagaaat cgatagagtt atagaatcaa tatataaata tcaattacca    480
ggttatatag aattaccagt tgatatagtt tcaaaagaaa tagaaatcga cgaaatgaaa    540
ccgctaaact taactatgag aagcaacgag aaaactttag agaaattcgt aaatgatgta    600
aaagaaatgg ttgcaagctc aaaaggacaa catattttag ctgattatga agtattaaga    660
```

```
gctaaagctg aaaaagaatt agaaggattt ataaatgaag caaaaatccc agtaaacact    720
ttaagtatag gaaagacagc agtatcagaa agcaatccat actttgctgg attattctca    780
ggagaaacta gttcagattt agttaaagaa ctttgcaaag cttctgatat agttttacta    840
tttggagtta aattcataga tactacaaca gctggattta gatatataaa taaagatgtt    900
aaaatgatag aaattggttt aactgattgt agaattggag aaactattta tactggactt    960
tacattaaag atgttataaa agctttaaca gatgctaaaa taaaattcca taacgatgta   1020
aaagtagaaa gagaagcagt agaaaaattt gttccaacag atgctaaatt aactcaagat   1080
agatatttca aacaaatgga agcgttctta aaacctaatg atgtattagt tggtgaaaca   1140
ggaacatcat atagtggagc atgtaatatg agattcccag aaggatcaag ctttgtaggt   1200
caaggatctt ggatgtcaat tggatatgct actcctgcag ttttaggaac tcatttagct   1260
gataagagca gaagaaacat tcttttaagt ggtgatggtt cattccaatt aacagttcaa   1320
gaagtttcaa caatgataag acaaaaatta aatacagtat tatttgtagt taacaatgat   1380
ggatatacaa ttgaaagatt aatccacgga cctgaaagag aatataacca tattcaaatg   1440
tggcaatatg cagaacttgt aaaaacatta gctactgaaa gagatataca accaacttgt   1500
ttcaaagtta caactgaaaa agaattagca gctgcaatgg aagaaataaa caaaggaaca   1560
gaaggtattg cttttgttga agtagtaatg gataaaatgg atgctccaaa atcattaaga   1620
caagaagcaa gtctatttag ttctcaaaat aactactaa                          1659

<210> SEQ ID NO 38
<211> LENGTH: 552
<212> TYPE: PRT
<213> ORGANISM: Sarcina ventriculi

<400> SEQUENCE: 38

Met Lys Ile Thr Ile Ala Glu Tyr Leu Leu Lys Arg Leu Lys Glu Val
1               5                   10                  15

Asn Val Glu His Met Phe Gly Val Pro Gly Asp Tyr Asn Leu Gly Phe
                20                  25                  30

Leu Asp Tyr Val Glu Asp Ser Lys Asp Ile Glu Trp Val Gly Ser Cys
            35                  40                  45

Asn Glu Leu Asn Ala Gly Tyr Ala Ala Asp Gly Tyr Ala Arg Leu Arg
        50                  55                  60

Gly Phe Gly Val Ile Leu Thr Thr Tyr Gly Val Gly Ser Leu Ser Ala
65                  70                  75                  80

Ile Asn Ala Thr Thr Gly Ser Phe Ala Glu Asn Val Pro Val Leu His
                85                  90                  95

Ile Ser Gly Val Pro Ser Ala Leu Val Gln Gln Asn Arg Lys Leu Val
                100                 105                 110

His His Ser Thr Ala Arg Gly Glu Phe Asp Thr Phe Glu Arg Met Phe
            115                 120                 125

Arg Glu Ile Thr Glu Phe Gln Ser Ile Ser Glu Tyr Asn Ala Ala
        130                 135                 140

Glu Glu Ile Asp Arg Val Ile Glu Ser Ile Tyr Lys Tyr Gln Leu Pro
145                 150                 155                 160

Gly Tyr Ile Glu Leu Pro Val Asp Ile Val Ser Lys Glu Ile Glu Ile
                165                 170                 175

Asp Glu Met Lys Pro Leu Asn Leu Thr Met Arg Ser Asn Glu Lys Thr
                180                 185                 190
```

```
Leu Glu Lys Phe Val Asn Asp Val Lys Glu Met Val Ala Ser Ser Lys
            195                 200                 205

Gly Gln His Ile Leu Ala Asp Tyr Glu Val Leu Arg Ala Lys Ala Glu
        210                 215                 220

Lys Glu Leu Glu Gly Phe Ile Asn Glu Ala Lys Ile Pro Val Asn Thr
225                 230                 235                 240

Leu Ser Ile Gly Lys Thr Ala Val Ser Glu Ser Asn Pro Tyr Phe Ala
                245                 250                 255

Gly Leu Phe Ser Gly Glu Thr Ser Ser Asp Leu Val Lys Glu Leu Cys
            260                 265                 270

Lys Ala Ser Asp Ile Val Leu Leu Phe Gly Val Lys Phe Ile Asp Thr
        275                 280                 285

Thr Thr Ala Gly Phe Arg Tyr Ile Asn Lys Asp Val Lys Met Ile Glu
    290                 295                 300

Ile Gly Leu Thr Asp Cys Arg Ile Gly Glu Thr Ile Tyr Thr Gly Leu
305                 310                 315                 320

Tyr Ile Lys Asp Val Ile Lys Ala Leu Thr Asp Ala Lys Ile Lys Phe
                325                 330                 335

His Asn Asp Val Lys Val Glu Arg Glu Ala Val Glu Lys Phe Val Pro
            340                 345                 350

Thr Asp Ala Lys Leu Thr Gln Asp Arg Tyr Phe Lys Gln Met Glu Ala
        355                 360                 365

Phe Leu Lys Pro Asn Asp Val Leu Val Gly Glu Thr Gly Thr Ser Tyr
    370                 375                 380

Ser Gly Ala Cys Asn Met Arg Phe Pro Glu Gly Ser Ser Phe Val Gly
385                 390                 395                 400

Gln Gly Ser Trp Met Ser Ile Gly Tyr Ala Thr Pro Ala Val Leu Gly
                405                 410                 415

Thr His Leu Ala Asp Lys Ser Arg Arg Asn Ile Leu Leu Ser Gly Asp
            420                 425                 430

Gly Ser Phe Gln Leu Thr Val Gln Glu Val Ser Thr Met Ile Arg Gln
        435                 440                 445

Lys Leu Asn Thr Val Leu Phe Val Val Asn Asn Asp Gly Tyr Thr Ile
450                 455                 460

Glu Arg Leu Ile His Gly Pro Glu Arg Glu Tyr Asn His Ile Gln Met
465                 470                 475                 480

Trp Gln Tyr Ala Glu Leu Val Lys Thr Leu Ala Thr Glu Arg Asp Ile
                485                 490                 495

Gln Pro Thr Cys Phe Lys Val Thr Thr Glu Lys Glu Leu Ala Ala Ala
            500                 505                 510

Met Glu Glu Ile Asn Lys Gly Thr Gly Ile Ala Phe Val Glu Val
        515                 520                 525

Val Met Asp Lys Met Asp Ala Pro Lys Ser Leu Arg Gln Glu Ala Ser
    530                 535                 540

Leu Phe Ser Ser Gln Asn Asn Tyr
545                 550

<210> SEQ ID NO 39
<211> LENGTH: 1152
<212> TYPE: DNA
<213> ORGANISM: Artificial Sequence
<220> FEATURE:
<223> OTHER INFORMATION: Synthetic optimized Alcohol dehydrogenase DNA
      sequence

<400> SEQUENCE: 39
```

```
atggcgtcat caactttta catcccgttc gtgaatgaaa tgggtgaagg cagtttggaa      60
aaggcgatta aggacttgaa tggctcaggt tttaaaaatg ctttaattgt gtcagatgcc     120
ttcatgaaca aaagtggtgt tgtcaagcaa gttgctgact tattgaagac gcagggcatt    180
aatagtgccg tttatgatgg tgtcatgcca aacccgaccg tgacagcggt tttagaaggt    240
ttgaaaatct tgaaggataa taacagtgac tttgttatct cattgggtgg cggtagtcca    300
catgattgtg ctaaagccat tgcgttagtt gcgacgaatg gcggtgaagt caaagattac    360
gaaggcattg acaagtcaaa aaagccagca ttaccgttga tgagtatcaa cacgactgcg    420
ggtactgcat cagaaatgac ccggttttgc attatcacag atgaagtccg tcatgtgaaa    480
atggctattg tggaccgcca cgttacgcca atggtcagtg tgaatgatcc gttattgatg    540
gttggcatgc caaagggttt gacggctgcc actggtatgg acgccttaac acacgctttc    600
gaagcctata gttcaaccgc ggcaacaccg attacggatg catgtgcttt gaaagctgcc    660
tcaatgatcg cgaaaaattt aaagactgca tgcgataacg gcaaggacat gccagctcgc    720
gaagctatgg cttatgcaca attttggcg gcatggcat tcaataacgc cagtttaggt     780
tacgttcatg ctatggccca ccagttgggc ggttattaca atttaccgca tggcgtctgt    840
aacgcggtgt tattgccaca cgtcttggct tacaatgcct cagtggttgc aggtcgatta    900
aaagatgttg gcgtcgctat gggtttggat attgccaact taggcgacaa ggaaggtgct    960
gaagcaacta tccaagctgt ccgggattta gcggcaagta ttggcatccc ggcgaatttg   1020
accgaattag gtgcaaaaaa ggaagatgtg ccgttattgg cggatcatgc attgaaggac   1080
gcttgcgcct taaccaatcc acggcagggc gaccagaagg aagttgaaga attattttta   1140
tcagcatttt aa                                                        1152
```

<210> SEQ ID NO 40
<211> LENGTH: 1707
<212> TYPE: DNA
<213> ORGANISM: Artificial Sequence
<220> FEATURE:
<223> OTHER INFORMATION: Synthetic optimized Pyruvate decarboxylase DNA
      sequence

<400> SEQUENCE: 40

```
atgagttaca cggtcggcac ttacttggca gaacgattgg tccagattgg tttgaagcat      60
cactttgcgg tggcgggcga ttacaacttg gttttattgg acaatttatt gttgaacaag    120
aacatggaac aggtctactg ttgcaacgaa ttaaattgtg gcttcagtgc ggaaggttat    180
gcccgagcaa agggtgctgc tgctgcagtt gtcacgtaca gtgttggtgc tttgtcagcc    240
tttgatgcga ttggtggcgc gtatgcagaa aacttgccgg tcattttaat ctcaggtgca    300
ccaaataaca atgatcatgc tgccggccac gtgttgcatc acgctttagg caagaccgac    360
taccattacc aattggaaat ggcaaagaac atcaccgcgg cagctgaagc tatctataca    420
ccggaagaag ctccagccaa aattgatcac gtgatcaaga cagcattgcg tgaaaagaaa    480
ccggtttact tagaaattgc atgtaacatc gctagtatgc catgtgctgc tccaggtcca    540
gcttcagcat tatttaacga tgaagccagt gacgaagcgt cattgaatgc agctgttgaa    600
gaaaccttaa aattcattgc aaatcgcgac aaggtggctg ttttggtcgg cagtaaatta    660
cgagccgcgg gtgccgaaga agcagctgtt aagtttgctg atgccttagg tggcgcggtt    720
gcaactatgc ccgctgcaaa atcattttc ccggaagaaa atccacatta tattggcacg    780
agttggggtg aagtctcata cccgggtgtg gaaaaaacta tgaaggaagc tgatgccgtt    840
```

```
attgcgttag caccagtctt caacgactat agtacgactg gttggacgga tatcccagac    900
ccgaaaaagt tggttttagc cgaaccgcgc agtgtggttg tcaatggtat tcgatttcca    960
tcagtccact tgaaagatta cttgacccgg ttagcccaga aagttagtaa aaagacaggc   1020
gcgttagact ttttcaagtc attgaacgct ggtgaattaa aaaaggctgc cccagcagat   1080
ccgagtgctc cattggtgaa cgcagaaatt gctcgtcaag ttgaagcgtt gttaacgcca   1140
aataccacag ttattgctga aactggtgat tcatggttta acgcccagcg gatgaagtta   1200
ccaaatggtg cgcgtgtcga atatgaaatg caatggggcc atattggttg gagtgttcca   1260
gctgcatttg gttatgctgt gggtgctcca gaacggcgta atattttgat ggttggtgat   1320
ggctcattcc aattaaccgc ccaggaagtg gcgcaaatgg ttcgcttgaa actgccggtg   1380
atcatctttt taatcaacaa ctacggctac acaattgaag ttatgatcca cgatggtcca   1440
tataacaata tcaagaattg ggactacgct ggcttaatgg aagtctttaa cggtaatggt   1500
ggctatgata gtggtgccgg caaaggtttg aaagcgaaga cgggtggcga attagctgaa   1560
gccattaagg tggcgttggc aaatacggat ggcccaactt taattgaatg ttttatcggt   1620
cgagaagact gcactgaaga attagtcaag tggggcaaac gggtcgcagc ggcaaatagt   1680
cggaaaccag tcaataagtt gttgtaa                                      1707
```